United States Patent
Bourke, Jr. et al.

(10) Patent No.: US 11,077,316 B2
(45) Date of Patent: Aug. 3, 2021

(54) INSERTION DEVICES AND SYSTEMS FOR PRODUCTION OF EMITTED LIGHT INTERNAL TO A MEDIUM AND METHODS FOR THEIR USE

(71) Applicant: Immunolight, LLC, Detroit, MI (US)

(72) Inventors: Frederic A. Bourke, Jr., Aspen, CO (US); Harold Walder, Belville, NC (US); Zakaryae Fathi, Raleigh, NC (US); Wayne F. Beyer, Jr., Bahama, NC (US)

(73) Assignee: Immunolight, LLC, Detroit, MI (US)

( * ) Notice: Subject to any disclaimer, the term of this patent is extended or adjusted under 35 U.S.C. 154(b) by 196 days.

(21) Appl. No.: 16/096,174

(22) PCT Filed: Apr. 25, 2017

(86) PCT No.: PCT/US2017/029300
§ 371 (c)(1),
(2) Date: Oct. 24, 2018

(87) PCT Pub. No.: WO2017/189506
PCT Pub. Date: Nov. 2, 2017

(65) Prior Publication Data
US 2019/0134419 A1 May 9, 2019

Related U.S. Application Data

(60) Provisional application No. 62/327,121, filed on Apr. 25, 2016.

(51) Int. Cl.
*A61K 31/015* (2006.01)
*A61N 5/06* (2006.01)
(Continued)

(52) U.S. Cl.
CPC .......... *A61N 5/0601* (2013.01); *A61K 31/015* (2013.01); *A61K 31/37* (2013.01);
(Continued)

(58) Field of Classification Search
CPC ........ A61N 5/0601; A61N 5/06; A61N 5/062; A61N 5/02; A61N 5/045; A61N 5/0624;
(Continued)

(56) References Cited

U.S. PATENT DOCUMENTS 6,443,978 B1 9/2002 Zharov
8,951,561 B2 2/2015 Vo-Dinh et al.
(Continued)

FOREIGN PATENT DOCUMENTS

JP 2002-511323 4/2002
JP 2006-149688 6/2006
(Continued)

OTHER PUBLICATIONS

International Search Report dated Aug. 28, 2017 in PCT/US2017/029300 filed Apr. 25, 2017.
(Continued)

*Primary Examiner* — Ankit D Tejani
*Assistant Examiner* — Joshua Brendon Solomon
(74) *Attorney, Agent, or Firm* — Oblon, McClelland, Maier & Neustadt, L.L.P.

(57) ABSTRACT

A system and method for emitting a wavelength of energy internal to a medium or internal to a human or animal subject, and methods for using the system in the treatment of a condition, disorder, or disease. The system includes 1) a source configured to produce an initiation signal penetrating at least a part of the medium or the human or animal subject and 2) an insertion device having an electronics assembly unit. The assembly unit includes 1) an emitter configured to emit the wavelength of energy of a predeter-
(Continued)

mined type to treat a disease or disorder in the human or animal subject or to produce a change in the medium and 2) a receiver that receives the signal.

28 Claims, 18 Drawing Sheets

(51) Int. Cl.
*A61K 31/37* (2006.01)
*A61K 31/519* (2006.01)
*A61K 41/00* (2020.01)
*A61M 31/00* (2006.01)
*A61N 1/40* (2006.01)
*A61N 5/02* (2006.01)
*A61K 38/00* (2006.01)
*A61N 1/372* (2006.01)
*A61N 5/04* (2006.01)

(52) U.S. Cl.
CPC ........ *A61K 31/519* (2013.01); *A61K 41/0057* (2013.01); *A61M 31/002* (2013.01); *A61N 1/40* (2013.01); *A61N 5/06* (2013.01); *A61N 5/062* (2013.01); *A61K 38/00* (2013.01); *A61M 2205/10* (2013.01); *A61N 1/37205* (2013.01); *A61N 5/02* (2013.01); *A61N 5/045* (2013.01); *A61N 5/0624* (2013.01); *A61N 2005/0602* (2013.01); *A61N 2005/0651* (2013.01); *A61N 2005/0656* (2013.01); *A61N 2005/0665* (2013.01)

(58) Field of Classification Search
CPC ................. A61N 1/40; A61N 1/37205; A61N 2005/0602; A61N 2005/0651; A61N 2005/0656; A61N 2005/0665; A61K 31/015; A61K 31/37; A61K 31/519; A61K 41/0057; A61K 38/00; A61M 31/002; A61M 2205/10

See application file for complete search history.

(56) References Cited

U.S. PATENT DOCUMENTS

| | | |
|---|---|---|
| 2004/0106849 A1 | 6/2004 | Cho et al. |
| 2005/0130240 A1 | 6/2005 | Lin et al. |
| 2007/0218049 A1 | 9/2007 | Chen et al. |
| 2008/0248001 A1 | 10/2008 | Bourke |
| 2009/0143761 A1 | 6/2009 | Cantor et al. |
| 2010/0016783 A1 | 1/2010 | Bourke, Jr. et al. |
| 2014/0180056 A1 | 6/2014 | Hoseit |
| 2014/0242035 A1 | 8/2014 | Bourke, Jr. |
| 2014/0272030 A1* | 9/2014 | Bourke, Jr. ......... A61M 1/3683 426/240 |
| 2014/0341845 A1 | 11/2014 | Bourke, Jr. |
| 2015/0360050 A1* | 12/2015 | Kaplitt ................. A61N 5/0622 607/88 |
| 2016/0066789 A1* | 3/2016 | Rogers .................... A61N 1/05 604/20 |
| 2017/0258908 A1 | 9/2017 | Bourke, Jr. |
| 2019/0336605 A1 | 11/2019 | Bourke, Jr. |

FOREIGN PATENT DOCUMENTS

| | | |
|---|---|---|
| JP | 2008-109954 | 5/2008 |
| JP | 2011-518650 | 6/2011 |
| JP | 2013-524864 | 6/2013 |
| JP | 2014-514039 | 6/2014 |
| WO | WO 2012/123939 A1 | 9/2012 |

OTHER PUBLICATIONS

Extended European Search Report dated Mar. 9, 2020, in Patent Application No. 17790229.3, 11 pages.
Office Action dated Apr. 5, 2021 in Japanese Patent Application No. 2019-507073, filed Apr. 25, 2017 w/English translation.

* cited by examiner

Top View

Partial section a-1 a-2 a-3 a-4

INSERTION DEVICES AND SYSTEMS FOR PRODUCTION OF EMITTED LIGHT INTERNAL TO A MEDIUM AND METHODS FOR THEIR USE

CROSS REFERENCE TO RELATED APPLICATIONS

This application claims priority to U.S. Provisional Patent Application 62/327,121, filed Apr. 25, 2016, entitled "INSERTION DEVICES AND SYSTEMS FOR PRODUCTION OF EMITTED LIGHT INTERNAL TO A MEDIUM", the entire contents of which are hereby incorporated by reference. This application is related to U.S. provisional Ser. No. 61/982,585, filed Apr. 22, 2014, entitled "INTERIOR ENERGY-ACTIVATION OF PHOTO-REACTIVE SPECIES INSIDE A MEDIUM OR BODY USING AN X-RAY SOURCE EMITTING LOW ENERGY X-RAYS AS INITIATION ENERGY SOURCE", the entire contents of which are hereby incorporated by reference. This application is related to provisional Ser. No. 62/096,773, filed: Dec. 24, 2014, entitled "INTERIOR ENERGY-ACTIVATION OF PHOTO-REACTIVE SPECIES INSIDE A MEDIUM OR BODY USING AN X-RAY SOURCE EMITTING LOW ENERGY X-RAYS AS INITIATION ENERGY SOURCE," the entire contents of which are incorporated herein by reference. This application is related to U.S. provisional Ser. No. 62/132,270, filed Mar. 12, 2015, entitled "TUMOR IMAGING WITH X-RAYS AND OTHER HIGH ENERGY SOURCES USING AS CONTRAST AGENTS PHOTON-EMITTING PHOSPHORS HAVING THERAPEUTIC PROPERTIES", the entire contents of which are hereby incorporated by reference. This application is related to U.S. provisional Ser. No. 62/147,390, filed Apr. 14, 2015, entitled "TUMOR IMAGING WITH X-RAYS AND OTHER HIGH ENERGY SOURCES USING AS CONTRAST AGENTS PHOTON-EMITTING PHOSPHORS HAVING THERAPEUTIC PROPERTIES", the entire contents of which are hereby incorporated by reference.

This application is related to provisional U.S. Ser. No. 12/401,478 (now U.S. Pat. No. 8,376,013) entitled "PLASMONIC ASSISTED SYSTEMS AND METHODS FOR INTERIOR ENERGY-ACTIVATION FROM AN EXTERIOR SOURCE, filed Mar. 10, 2009, the entire contents of which are incorporated herein by reference. This application is related to U.S. Ser. No. 13/102,277 entitled "ADHESIVE BONDING COMPOSITION AND METHOD OF USE," filed May 6, 2011, the entire contents of which are incorporated herein by reference. This application is related to provisional Ser. No. 61/035,559, filed Mar. 11, 2008, entitled "SYSTEMS AND METHODS FOR INTERIOR ENERGY-ACTIVATION FROM AN EXTERIOR SOURCE," the entire contents of which are hereby incorporated herein by reference. This application is related to provisional Ser. No. 61/030,437, filed Feb. 21, 2008, entitled "METHODS AND SYSTEMS FOR TREATING CELL PROLIFERATION DISORDERS USING PLASMONICS ENHANCED PHOTOSPECTRAL THERAPY (PEPST) AND EXCITON-PLASMON ENHANCED PHOTOTHERAPY (EPEP)," the entire contents of which are hereby incorporated herein by reference. This application is related to non-provisional Ser. No. 12/389,946, filed Feb. 20, 2009, entitled "METHODS AND SYSTEMS FOR TREATING CELL PROLIFERATION DISORDERS USING PLASMONICS ENHANCED PHOTOSPECTRAL THERAPY (PEPST) AND EXCITON-PLASMON ENHANCED PHOTOTHERAPY (EPEP)," the entire contents of which are hereby incorporated herein by reference. This application is related to non-provisional Ser. No. 11/935,655, filed Nov. 6, 2007, entitled "METHODS AND SYSTEMS FOR TREATING CELL PROLIFERATION RELATED DISORDERS," and to provisional Ser. No. 60/910,663, filed Apr. 8, 2007, entitled "METHOD OF TREATING CELL PROLIFERATION DISORDERS," the contents of each of which are hereby incorporated by reference in their entireties. This application is related to provisional Ser. No. 61/035,559, filed Mar. 11, 2008, entitled "SYSTEMS AND METHODS FOR INTERIOR ENERGY-ACTIVATION FROM AN EXTERIOR SOURCE," the entire contents of which are hereby incorporated herein by reference. This application is related to U.S. patent application Ser. No. 12/764,184, filed Apr. 21, 2010, the entire disclosure of which is hereby incorporated by reference. This application is also related to provisional Ser. No. 61/792,125, filed Mar. 15, 2013, entitled "INTERIOR ENERGY-ACTIVATION OF PHOTO-REACTIVE SPECIES INSIDE A MEDIUM OR BODY," the entire contents of which are hereby incorporated herein by reference. This application is further related to provisional Ser. No. 61/505,849 filed Jul. 8, 2011, the entire contents of which are hereby incorporated herein by reference. This application is related to U.S. provisional patent application 61/443,019, filed Feb. 15, 2011, the entire disclosure of which is hereby incorporated by reference. This application is related to U.S. application Ser. No. 14/131,564, filed Jan. 8, 2014, each entitled "PHOSPHORS AND SCINTILLATORS FOR LIGHT STIMULATION WITHIN A MEDIUM," the entire contents of each of which is incorporated herein by reference. This application is related to and U.S. application Ser. No. 14/206,337, filed Mar. 12, 2014, entitled "INTERIOR ENERGY-ACTIVATION OF PHOTO-REACTIVE SPECIES INSIDE A MEDIUM OR BODY," the entire contents of which are hereby incorporated herein by reference. This application is related to PCT application PCT/2015/027058 filed Apr. 22, 2015 entitled "TUMOR IMAGING WITH X-RAYS AND OTHER HIGH ENERGY SOURCES USING AS CONTRAST AGENTS PHOTON-EMITTING PHOSPHORS HAVING THERAPEUTIC PROPERTIES," the entire contents of which are hereby incorporated by reference. This application is related to PCT application PCT/2015/027060 filed Apr. 22, 2015 entitled "INTERIOR ENERGY-ACTIVATION OF PHOTO-REACTIVE SPECIES INSIDE A MEDIUM OR BODY USING AN X-RAY SOURCE EMITTING LOW ENERGY X-RAYS AS INITIATION ENERGY SOURCE," the entire contents of which are hereby incorporated by reference. This application is related to U.S. patent application 62/103,409 entitled "NON-INVASIVE SYSTEMS AND METHODS FOR TREATMENT OF A HOST CARRYING A VIRUS WITH PHOTOACTIVATABLE DRUGS," filed Jan. 14, 2015, 2015, the entire contents of which are hereby incorporated by reference. This application is related to U.S. patent application 62/246,360 entitled "METHODS FOR RADIOTHERAPY TO TRIGGER LIGHT ACTIVATION DRUGS," filed Oct. 26, 2015, the entire contents of which are hereby incorporated by reference. This application is related to U.S. patent application 62/290,203 entitled "PHOSPHOR-CONTAINING DRUG ACTIVATOR, SUSPENSION THEREOF, SYSTEM CONTAINING THE SUSPENSION, AND METHODS FOR USE," filed Feb. 2, 2016, the entire contents of which are hereby incorporated by reference.

BACKGROUND OF THE INVENTION

Field of Invention

The invention relates to methods and systems for producing light inside a medium that is nominally opaque to light in the UV and VIS regime.

Discussion of the Background

Presently, light (i.e., electromagnetic radiation from the radio frequency through the visible to the X-ray wavelength range) is used in a number of Industrial, Scientific and Medical (ISM) bands in addition to other communication, electronic, and pharmaceutical processes. Light in the infra-red and visible range is typically generated from an electrical energy source which for example either heats a material to extremely high temperatures where black body emission occurs (as in an incandescent lamp). Light in the visible and ultraviolet range is typically generated by heating a gas to an electrical discharge where transitions from one electronic state of the gas atom or molecule occur with the emission of light. There are also semiconductor based light sources (as in light emitting diodes and semiconducting lasers) where electrons/holes in a material recombine to produce light emission.

Visible light is defined as the electromagnetic radiation with wavelengths between 380 nm and 750 nm. In general, electromagnetic radiation including light is generated by the acceleration and deceleration or changes in movement (vibration) of electrically charged particles, such as parts of molecules (or adjacent atoms) with high thermal energy, or electrons in atoms (or molecules). Both processes play a role in the glowing filament of incandescent lamps, whereas the latter process (electrons within atoms) occurs in fluorescent lamps.

For reference purposes, infra-red (IR) radiation just beyond the red end of the visible region; and, ultra-violet (UV) radiation has a shorter wavelength than violet light. The UV portion of the spectrum is divided into three regions: UVA (315-400 nm), UVB (280-315 nm) and UVC (100-280 nm).

Industrial lamps used in lighting applications cover the visible range of wavelengths for proper white perception. Thermal sources like heated filaments can be made of different type conductors, including W-filaments, halogen-protected W-filaments, and electrically induced high temperature plasmas (arc lamps).

The power (energy emitted per second) of a radiant source is frequently expressed in watts (W), but light can also be expressed in lumens (lm) to account for the varying sensitivity of the eye to different wavelengths of light. The derived relevant units are the radiance (luminance) of a source in $W/m^2$ ($lm/m^2$) in a certain direction per steradian (unit of solid angle) and the irradiance (illuminance) of a surface in $W/m^2$ ($lm/m^2$ or lux).

With the development of ultraviolet sources, ultraviolet radiation has become increasingly utilized for industrial, chemical, and pharmaceutical purposes. For example, UV light is known to sterilize media and is known to drive a number of photo-activated chemical processes such as the cross-linking of polymers in adhesives or coatings. Typically, ultraviolet sources use gas discharge lamps to generate emitted light in the ultraviolet range. The emitted light is then optically filtered to remove many of not all of the non-ultraviolet frequencies. Ultraviolet light can also be produced in semiconductor phosphors from the excitation of these phosphors from high energy sources such as, for example, X-ray irradiation.

UV radiation suffers from a lack of depth of penetration in matter especially biological media, polymers and most solids). For this reason, UV based photo-initiation is limited by direct line of site which prevents many volumetric applications. UV has been typically limited to reactions taking place on the outer surfaces of materials may they be solids or liquids; organic or inorganic; biological organs, living tissues and composites thereof, structural composites, materials residing inside chemical tanks/reactors for food processing or hydrocarbon chains fractionation (to name a few examples).

SUMMARY OF THE INVENTION

In one embodiment, there is provided a system for production of emitted light internal to a medium or internal to a human or animal subject. The system includes 1) a source configured to produce an initiation signal penetrating at least a part of the medium or the human or animal subject and 2) an insertion device having an electronics assembly unit. The assembly unit includes 1) an emitter configured to emit light of a predetermined type to treat a disease or disorder in the human or animal subject or to produce a change in the medium and 2) a receiver that receives the signal and optionally 3) a receiving and transmitting device. The assembly unit is configured, upon receiving the signal, to power the emitter thereby emitting the light interior the human or animal subject or interior the medium.

In one embodiment, there is provided a medical catheter including an insertion device having an electronics assembly unit. The assembly unit includes 1) an emitter, and 2) a receiver that receives an initiation signal. The assembly unit is configured, upon receiving the initiation signal, to power the emitter to thereby emit light interior of the human or animal subject to treat the human or animal subject. The medical catheter includes an insertion sleeve having, at a distal end thereof, for insertion into a patient.

In one embodiment there is provided an insertion device including an electronics assembly unit. The electronics assembly unit includes an emitter and a receiver that receives an initiation signal, and an internal controller having a memory programmed with instructions which when executed cause the controller to recognize the initiation signal and to power the emitter to thereby emit the light interior of the human or animal subject to treat the human or animal subject or thereby emit the light interior to the medium to produce a change in the medium.

In one embodiment, there is provided a system for production of emitted light internal to a medium or internal to a human or animal subject. The system includes an emitter configured to emit light of a predetermined type to treat a disease or disorder in the human or animal subject or to produce a change in the medium. The system includes a controller which 1) controls an initiation signal penetrating at least a part of the medium or the human or animal subject to activate the emitter and 2) provides a control signal moderating an amount of said light being emitted in the human or animal subject.

In one embodiment, there is provided a system for emitting a wavelength of energy internal to a medium or internal to a human or animal subject. The system includes an embedded insertion device embedded within a region of a human or animal subject, a computerized control controlling an external source of electro-magnetic transmissions outside the human or animal subject, and a relay embedded within the region of a human or animal subject and disposed between the embedded insertion device and the outside world. The relay passes along the electro-magnetic transmissions to the embedded insertion device.

In one embodiment, there is provided a system for treating a patient or a subject with a photoactivatable drug. The system includes a source of a wavelength of energy which is capable of activating the photoactivatable drug and a blood supply displacement system which temporarily displaces blood from a diseased site or organ to be treated with a biocompatible fluid which is less absorptive of the wavelength of energy than blood.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1A:
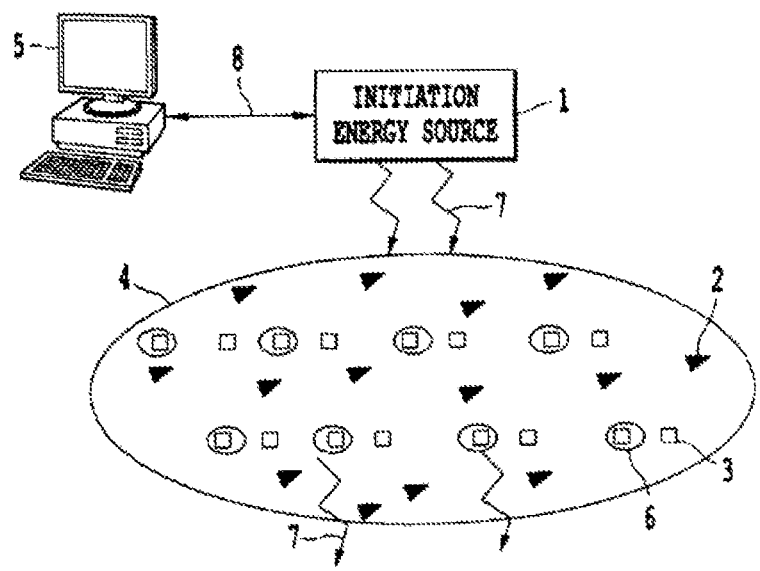
FIG. 1A is a schematic depicting a system according to another embodiment of the invention in which the initiation energy source is directed to a medium having insertion devices dispersed within the medium.

The invention is directed to methods and systems for producing light from an insertion device, where the insertion device is activatable once inserted inside a biological or non-biological medium. The medium may be nominally opaque to light in the UV and VIS regime. In various embodiments of the invention, the light produced is produced within a human or animal subject for treating the human or animal subject or to produce a change in the medium.

The following discussions describe the conventional understanding of 1) psoralens and their photo-reactivity and 2) alkylating agents and their photo-reactivity and other such photoactivatable drugs. In various embodiments, the present invention can utilize those and other pathways to cause reactions of the photoactivatable drugs with target cells by way of the insertion devices described herein.

All of the following documents noted herein have their entire contents incorporated herein by reference.

Psoralens and Related Compounds Activatable by the Insertion Devices of the Invention U.S. Pat. No. 6,235,508 describes that psoralens are naturally occurring compounds which have been used therapeutically for millennia in Asia and Africa. The action of psoralens and light has been used to treat vitiligo and psoriasis (PUVA therapy; Psoralen Ultra Violet A). Psoralen is capable of binding to nucleic acid double helices by intercalation between base pairs; adenine, guanine, cytosine and thymine (DNA) or uracil (RNA). Upon sequential absorption of two UV-A photons, psoralen in its excited state reacts with a thymine or uracil double bond and covalently attaches to both strands of a nucleic acid helix. The cross-linking reaction appears to be specific for a thymine (DNA) or a uracil (RNA) base. Binding may proceed when psoralen is intercalated in a site containing thymine or uracil, but an initial photoadduct must absorb a second UVA photon to react with a second thymine or uracil on the opposing strand of the double helix in order to crosslink each of the two strands of the double helix, as shown below. This is a sequential absorption of two single photons as shown, as opposed to simultaneous absorption of two or more photons.

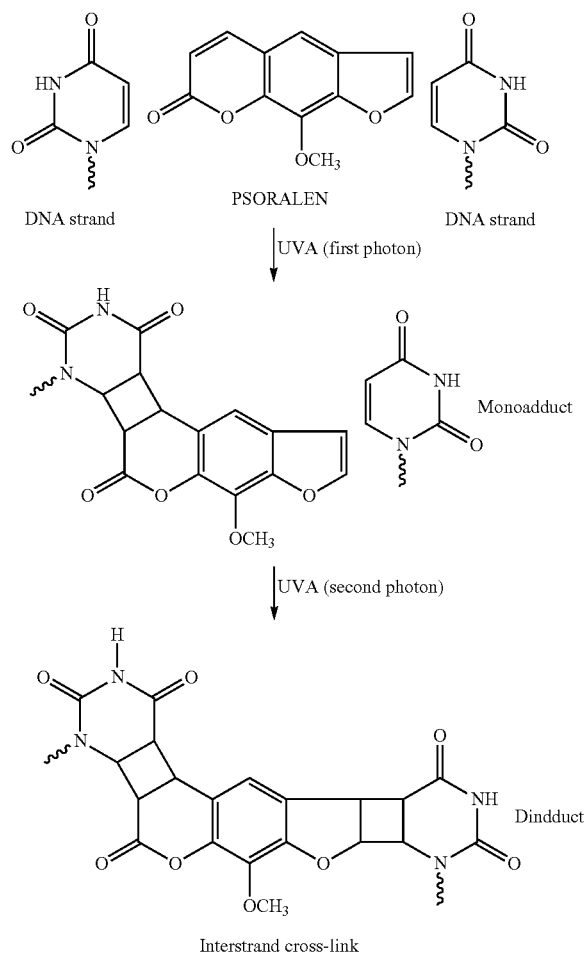

U.S. Pat. No. 4,748,120 to Wiesehan is an example of the use of certain substituted psoralens by a photochemical decontamination process for the treatment of blood or blood products.

Additives, such as antioxidants are sometimes used with psoralens, such as 8-MOP, AMT and I-IMT, to scavenge singlet oxygen and other highly reactive oxygen species formed during photoactivation of the psoralens. It is well known that UV activation creates such reactive oxygen species, which are capable of seriously damaging otherwise healthy cells. Much of the viral deactivation may be the result of these reactive oxygen species rather than any effect of photoactivation of psoralens.

Some of the best known photoactivatable compounds are derivatives of psoralen or coumarin, which are nucleic acid intercalators. For psoralens and coumarins, this chemical pathway is likely to lead to the formation of a variety of ring-opened species, such as shown below for coumarin:

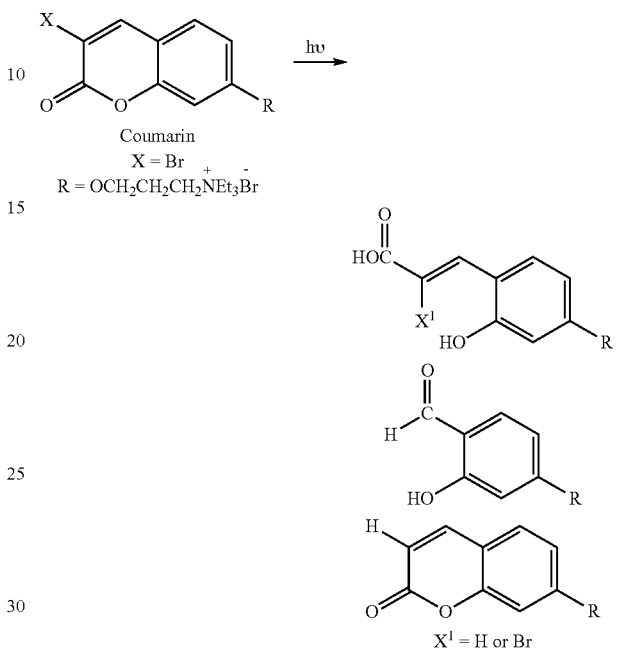

Midden (W. R. Midden, Psoralen DNA photobiology, Vol II (ed. F. P. Gaspalloco) CRC press, pp. 1. (1988) has presented evidence that psoralens photoreact with unsaturated lipids and photoreact with molecular oxygen to produce active oxygen species such as superoxide and singlet oxygen that cause lethal damage to membranes.

U.S. Pat. No. 6,235,508 describes that 8-MOP and AMT are unacceptable photosensitizers, because each indiscriminately damages both cells and viruses. Studies of the effects of cationic side chains on furocoumarins as photosensitizers are reviewed in Psoralen DNA Photobiology, Vol. I, ed. F. Gaspano, CRC Press, Inc., Boca Raton, Fla., Chapter 2. U.S. Pat. No. 6,235,508 gleans the following from this review: most of the amino compounds had a much lower ability to both bind and form crosslinks to DNA compared to 8-MOP, suggesting that the primary amino functionality is the preferred ionic species for both photobinding and crosslinking.

U.S. Pat. No. 5,216,176 describes a large number of psoralens and coumarins that have some effectiveness as photoactivated inhibitors of epidermal growth factor. Halogens and amines are included among the vast functionalities that could be included in the psoralen/coumarin backbone.

U.S. Pat. No. 5,984,887 describes using extracorporeal photopheresis with 8-MOP to treat blood infected with CMV. The treated cells as well as killed and/or attenuated virus, peptides, native subunits of the virus itself (which are released upon cell break-up and/or shed into the blood) and/or pathogenic noninfectious viruses are then used to generate an immune response against the virus, which was not present prior to the treatment.

Other Photoactive Compounds Activatable by the Insertion Devices of the Invention Other photoactive or photoactivatable compounds are known in the art. Of these, an article by Warfield et al entitled "*Ebola* Virus Inactivation with Preservation of Antigenic and Structural Integrity by a Photoinduable Alkylating Agent," J. Infect. Dis. 2007 Nov. 15; 196 Suppl 2:S276-83 describes the treatment of the Zaire *Ebola* virus (ZEBOV) ex situ by extraction of infected blood from a mouse and exposure of the extracted blood to UV light (310 to 360 nm) with the blood containing an alkylating agent, in this case iodonophthylazide (INA) to inactivate the ZEBOV. Mice treated with the inactivated *Ebola* virus were resistant to exposure to the *Ebola* virus. These authors reported that INA is hydrophobic compound that preferentially partitions into lipid bilayers of the *Ebola* virus. These authors reported that the "INA treatment renders ZEBOV completely noninfectious without structural perturbation" and that "INA-inactivated ZEBOV was immunogenic and protected mice from lethal challenge."

U.S. Pat. No. 7,049,110 entitled "Inactivation of West Nile virus and malaria using photosensitizers" describes the inactivation of microorganisms in fluids or on surfaces, preferably the fluids that contain blood or blood products and biologically active proteins. An effective, non-toxic amount of a photosensitizer was added to the fluid, and the fluid was exposed to photoradiation sufficient to activate the photosensitizer whereby microorganisms were inactivated.

The '110 patent describes a 7,8-dimethyl-10-ribityl isoalloxazine photosensitizers and other photosensitizers including endogenous alloxazine or isoalloxazine photosensitizers. The '110 patent describes the treatment of a host carrying various microorganisms including viruses (both extracellular and intracellular), bacteria, bacteriophages, fungi, blood-transmitted parasites such as malaria, and protozoa. Exemplary viruses include acquired immunodeficiency (HIV) virus, hepatitis A, B and C viruses, sinbis virus, cytomegaloviris, vesicular stomatitis virus, herpes simplex viruses, e.g. types I and II, human T-lymphotropic retroviruses, HTLV-III, lymphadenopathy virus LAV/IDAV, parvovirus, transfusion-transmitted (TT) virus, Epstein-Barr virus, West Nile virus and others known to the art. Bacteriophages include ΦX174, Φ6, λ, R17, T4, and T2. Exemplary bacteria include *P. aeruginosa, S. aureus, S. epidermis, L. monocytogenes, E. coli, K. pneumonia* and *S. marcescens*. One particular class of microorganisms is non-screened microorganisms—those microorganisms that are not screened by current blood banking processes. Some non-screened microorganisms include malaria and West Nile virus. One class of microorganisms includes those transmitted by mosquitoes, including malaria and West Nile virus.

The '110 patent describes that the preferable use endogenous photosensitizers, including endogenous photosensitizers which function by interfering with nucleic acid replication. In 7,8-dimethyl-10-ribityl isoalloxazine, the chemistry believed to occur between 7,8-dimethyl-10-ribityl isoalloxazine and nucleic acids does not proceed via singlet oxygen-dependent processes (i.e. Type II mechanism), but rather by direct sensitizer-substrate interactions (Type I mechanisms). In addition, 7,8-dimethyl-10-ribityl isoalloxazine appears not to produce large quantities of singlet oxygen upon exposure to UV light, but rather exerts its effects through direct interactions with substrate (e.g., nucleic acids) through electron transfer reactions with excited state sensitizer species.

An article by Sharma et al. entitled "Safety and protective efficacy of INA-inactivated Venezuelan equine encephalitis virus: Implication in vaccine development," in Vaccine, volume 29, issue 5, 29 Jan. 2011, pages 953-959, described that that hydrophobic alkylating compound, 1,5-iodonaphthyl-azide (INA) can efficiently inactivate the virulent strain of Venezuelan equine encephalitis virus (VEEV), upon exposure of the INA to "full light conditions." Sharma et al. further demonstrated the protective efficacy of INA-inactivated V3000 and V3526 to not cause disease in suckling mice and to induce an anti-VEEV antibody response which protected mice from a virulent VEEV challenge. Sharma et al. reported that none of the mice which received INA-inactivated V3526 showed any clinical symptoms of disease such as, hunched posture, stunted growth, lethargic or paralysis and grew similar to that of the control mice.

An article by Heilman et al. entitled "Light-Triggered Eradication of *Acinetobacter baumannii* by Means of NO Delivery from a Porous Material with an Entrapped Metal Nitrosyl" in J. Am. Chem. Soc., 2012, 134 (28), pp 11573-11582 (May 11, 2012) describes photoactive manganese nitrosyl, namely [Mn(PaPy3)(NO)](ClO4) ({Mn—NO}), loaded into the columnar pores of an MCM-41 host. Heliman et al. report that, when suspensions of the loaded materials in saline solution were exposed to low-power (10-100 mW) visible light, rapid release of NO was observed. The released nitric oxide effectively cleared the bacteria from the treated areas of the plates, showing that the nitric oxide easily penetrated through the agar layer. The amount of light used to activate the compound was 100 milliWatts per square centimeter.

U.S. Pat. No. 8,268,602 entitled "CELLULAR AND VIRAL INACTIVATION" describes procedures for providing compositions of inactivated viruses, bacteria, fungi, parasites and tumor cells that can be used as vaccines, as well as methods for making such inactivated viruses, bacteria, fungi, parasites and tumor cells are also provided. More specifically, the '602 patent describes methods for inactivating an infective agent or cancer cell that involve exposing the agent or cell to a hydrophobic photoactivatable compound, for example, 1,5-iodonaphthylazide (INA) activated by ultraviolet light.

Insertion Devices and Methods of Use

One system of the invention includes 1) an initiation source configured to produce an initiation signal penetrating at least a part of the medium or the human or animal subject (or a medium to be changed by photoactivation of a reagent therein) and 2) an insertion device including an emitter associated with a microelectronics assembly unit. The assembly unit in one embodiment includes 1) for the emitter, a light emitting device (such as for example a light emitting diode or LED or electroluminescent device) configured to emit light of a predetermined wavelength to treat disease or disorder in the human or animal subject or to produce a change in the medium, 2) an optional battery that powers the light emitting device, and 3) a receiver (e.g. an RF antenna) that picks up the initiation signal and/or couples power into the emitter. The assembly unit is configured, upon receiving the initiation signal, to power the light emitting device thereby emitting light of the predetermined wavelength into the interior of the human or animal subject or into the interior of the medium.

In one embodiment of the invention, the insertion device is a microdevice or an array of insertion devices. The term "microdevice" refers to a device having features of 100s of microns or submicron dimensions. The insertion devices with these preferable dimensions can be used in any number of medical, physical, and/or chemical processes involving the irradiation of internal structures at prescribed optical wavelengths to directly or indirectly produce a change in the medium. For example, the insertion devices in various embodiments can include channels or microchannels for injection of an activatable agent into the medium.

Some of these channels can be used for blood separation functions for the purpose of increasing the efficacy of drug activation. The channels or microchannels in various non-limiting embodiments can be on the order of 1 µm to 200 µm in diameter, typically 10 µm to 75 µm in diameter, and approximately 0.1 to 50 cm in length. The channels or microchannels can be connected to or themselves form microvoids having for example a volume of about 1 nl to about 100 µl, typically about 10 nl to 20 µl. However, the insertion devices of the present invention can be larger or smaller in scale.

Reference will now be made in detail to the accompanying drawings, in which like reference characters refer to corresponding elements.

As shown in FIG. 1A, an exemplary system according to one embodiment of the invention may have an initiation energy source 1 directed at medium 4. The medium 4 can be an artificial medium or a biological medium. Activatable agents 2 can be dispersed throughout the medium 4 or can be administered locally from the insertion devices 3 which has shown have been inserted into the medium to be treated. The initiation energy source 1 may be connected via a network 8 to a computer system 5 capable of directing the delivery of the initiation energy. In various embodiments, the insertion device(s) 3 receive microwave radiation or radiofrequency radiation signals and generate emitted light of one or more predetermined wavelengths in the infrared, visible, or ultraviolet range to treat a disease or disorder in the human or animal subject or to produce physical and/or biological changes in the medium.

As used herein, the term "change in the medium" includes but is not limited to the inducement of a photoactivated reaction such as for example drug activation, cell or bacteria or virus or yeast kill, radical generation, sterilization, polymerization, hardening, curing, localized heating from the emitted light, etc. One example of a biological change includes the thermal activation or the photo-activation of a therapeutic agent that in turn triggers a response in the cell viability in the medium. Other changes in a biological medium such as those induced by photoactivation of drugs, photodynamic therapy, photobiomodulation, and photostimulation are discussed in detail below.

In various embodiments, the insertion device(s) 3 are encapsulated in silica or a polymer for biocompatibility. The silica or polymer in these embodiments is capable of transmitting the infrared, visible, or ultraviolet light into the medium 4 surrounding the insertion device(s) 3. As shown in FIG. 1A, initiation energy 7 (e.g. in the form of radiation from the initiation energy source 1) permeates throughout the medium 4. In some cases, the initiation energy 7 from the initiation energy source 1 may only permeate partially through the medium.

In various embodiments, the initiation energy source 1 can be a radio frequency or microwave source or infrared source emitting electromagnetic waves at a frequency which permeates at least a part of the medium and which triggers from the insertion device light emission. In various embodiments, the emitted light can interact with energy modulation elements 6 in the medium surrounding insertion device(s) 3. As discussed below in more detail, the activatable agents 2 or the energy modulation elements 6 can have plasmonics agents which enhance the effect of light emitted from the insertion device(s) 3. A computer or processor or computing device 5 controls the initiation energy source and provides wireless signals for control of the insertion device(s) 3. Communication from computer 5 to the imitation energy source occurs over a wired, fiber optic, or wireless communication network 8.

Figure 1B:
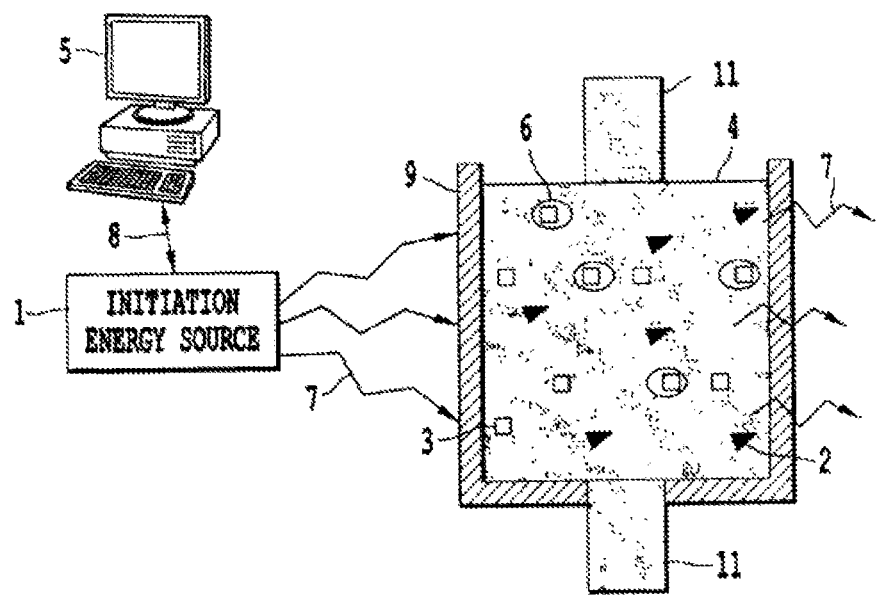
FIG. 1B is a schematic depicting a system according to another embodiment of the invention in which the initiation energy source is directed to a container enclosing a medium having insertion devices dispersed within the medium.

FIG. 1B is a schematic depicting another system according to another embodiment of the invention in which the initiation energy source 1 of FIG. 1A is directed to the insertion device(s) 3 which in turn irradiate energy modulation elements 6 placed in the vicinity of medium 4 (e.g., a liquid or other fluid-like medium) and held inside a container 9. As shown in FIG. 1B, the insertion device(s) 3 by their positioning in the medium have the medium surrounding the insertion device(s) 3. The insertion device(s) 3 in this embodiment are inside the medium and are therefore intimately in a vicinity of the medium to be activated.

The container 9 is made of a material that is "transparent" to the initiation energy 7. For example, plastic, quartz, glass, or aluminum containers would be sufficiently transparent to X-rays, while plastic or quartz or glass containers would be transparent to microwave or radio frequency radiation. The insertion device(s) 3 or encapsulated insertion devices 6 can be dispersed uniformly throughout the medium or may be segregated in distinct parts of the medium or further separated physically from the medium by encapsulation structures 10, as described below. A supply 11 provides the medium 4 to the container 9.

Accordingly, as used herein, "in a vicinity of" refers to the insertion device(s) 3 or the encapsulated insertion devices 6 being disposed completely inside a medium, partly inside or partly outside a medium, adjacent a medium, or completely outside a medium where light from the insertion devices 3 irradiates a part or the whole of the medium.

Figure 1C:
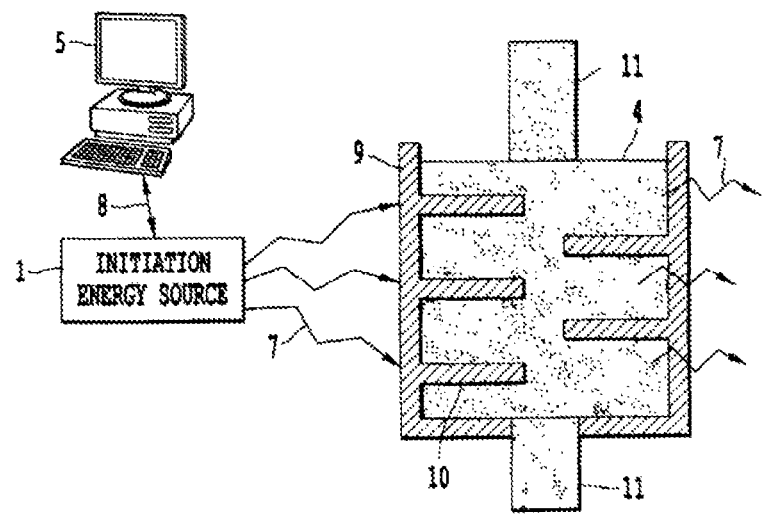
FIG. 1C is a schematic depicting a system according to another embodiment of the invention in which the initiation energy source is directed to a container enclosing a medium having insertion devices segregated within the medium by way of intruding encapsulated structures holding UV or visible light emitters.

FIG. 1C is a schematic depicting a system according to another embodiment of the invention in which the initiation energy source is directed to a container enclosing a medium having insertion devices segregated within the medium by way of intruding encapsulated structures holding UV or visible light emitters. In FIG. 1C, encapsulated structures 10 (containing the UV or visible light emitters) are aligned with an orientation in line with the external initiation energy source 1. In this configuration, each of the encapsulated structures 10 has itself a "line-of-sight" to the external initiation energy source 1 without being occluded by other of the encapsulated structures 10. In other embodiments, the encapsulated structures 10 are not so aligned in that direction, but could be aligned perpendicular to the direction, or could be randomly placed.

Figure 1D:
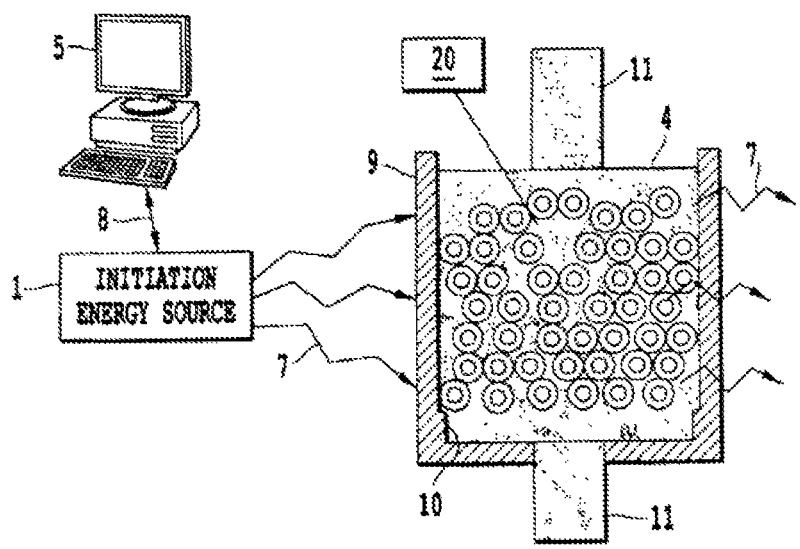
FIG. 1D is a schematic depicting a system according to another embodiment of the invention in which the initiation energy source is directed to a container enclosing a medium having insertion devices segregated within the medium in a fluidized bed configuration.

FIG. 1D is a schematic depicting a system according to another embodiment of the invention in which the initiation energy source is directed a container enclosing a medium having insertion device(s) 3 segregated within the medium in a fluidized bed 20 configuration. The fluidized bed 20 includes the insertion device(s) 3 inside encapsulated structures 10 in a configuration where a fluid to be treated is passed between the encapsulated structures 10. The encapsulated structures 10 can include also energy modulation agents and/or other luminescent materials and/or plasmonics agents as described herein.

In the either configuration of FIGS. 1C and 1D, the medium to be treated in one embodiment would flow by the encapsulated structures 10, and the separation distance between the encapsulated structures 10 would be set a distance smaller than the UV penetration depth in the medium. Thus, as shown in FIGS. 1C and 1D, the medium being treated does need not to be stationary in order for the encapsulated structures 10 to be in a vicinity of the medium to be treated. In other embodiments, the medium to be treated could be stationary.

In one embodiment of the invention described here, the concentration of insertion device(s) 3 in the medium or the spacing between the encapsulated structures 10 is set such that the insertion device(s) 3 are separated from each other in the medium by less than a UV depth of penetration into the medium. Higher concentrations are certainly usable and will generate higher UV fluxes should the energy source have enough intensity to "light" all the luminescent particles.

For a relatively unclouded aqueous medium, UV-B irradiance decreases to 1% after penetration into the water samples between 0.2 m and 1 m, whereas UV-A penetrates on the order of several meters. For such mediums, the concentration of light emitter is more determined by the time needed for the intended UV flux to produce deactivation or activation of an agent in the medium, rather than having to be set based on a concentration of light emitter where the medium itself does not occlude the UV stimulated emission from penetrating throughout the medium. The placement of the light emitter in the vicinity of the medium is not restricted by the optical density of the medium.

The insertion device(s) 3 described in this invention can include many of the electrical and housing components described in U.S. Pat. No. 5,358,514. In the '514 patent, electrodes were attached to a nerve or muscle without suturing permitting the microdevice of the '514 patent (and suitable here in the present invention) to stimulate the nerve or muscle, or sense signals associated with the nerve or muscle, using a minimal amount of energy.

Figure 2A:
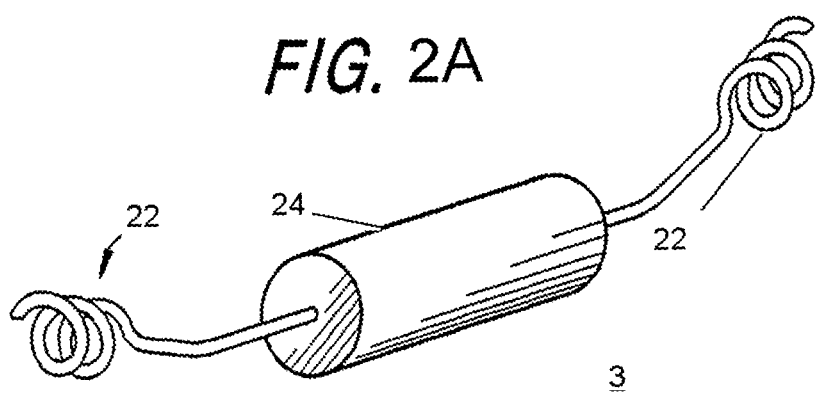
FIG. 2A is a schematic of one embodiment of an insertion device of the invention with opposing electrodes for self attachment to a component of the medium to be treated.

FIG. 2A is a schematic of an insertion device 3 of the present invention with opposing active or inactive electrodes 22 for self attachment to a muscle or nerve or organ. As shown in FIG. 2A, the opposing electrodes are attached to a device housing 24. The main function of electrodes 24 in this invention is for attachment of device 3 to a muscle or nerve or target organ to be treated, although the electrodes 24 can supply electrical pulses to the muscle or nerve or target organ if needed as part of the treatment. Inside the housing 24 resides electronic control circuitry, a coil for receiving an initiation signal, and a battery to charge or power the electronic control circuitry, the light emitter, or the fluid injectors. In one embodiment, the insertion device 3 includes a hermetically-sealed housing which is inert to body fluids and tissue or other components of the medium in which the insertion device is placed.

Figure 2B:
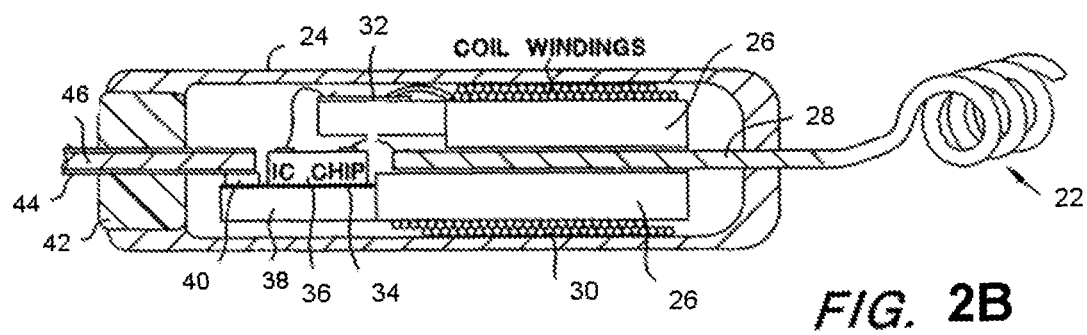
FIG. 2B is a sectional schematic of one embodiment of the microdevice of the invention.
Figure 2C:
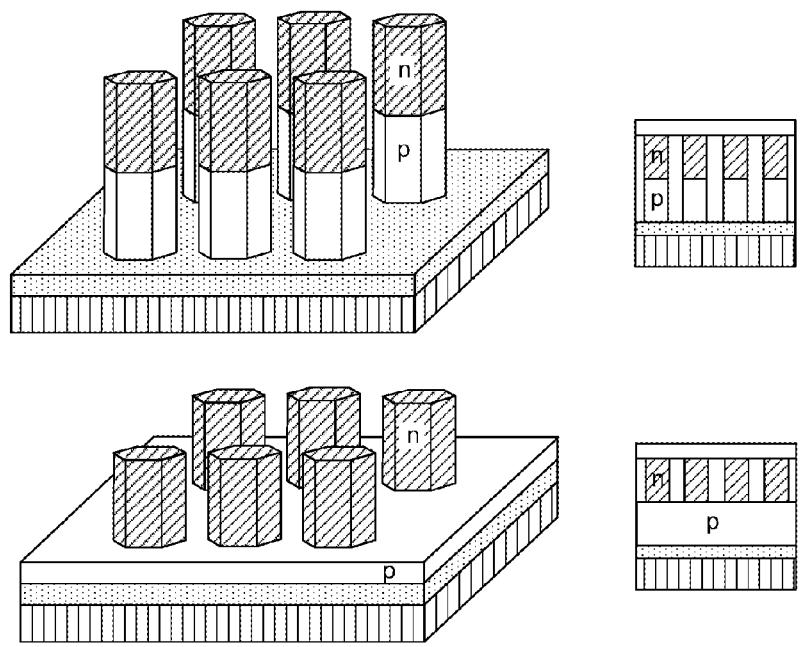
FIG. 2C are schematic views of two types of inorganic LED device designs incorporating nanoscale crystalline hetero-structures.

FIG. 2B is a sectional schematic of one embodiment of the insertion device 3 of the present invention. This embodiment shows for the sake of simplicity two attachment electrodes 22, although more attachment electrodes (or no attachment electrodes) could be used depending on how the device(s) 3 are to be used. The electrode is connected to the interior of housing 24 by attachment section 28 sealed to the housing 24. As illustrated in FIG. 2B, at least one emitter, e.g., light emitting source 26 is contained inside housing 24. The light emitting source 26 can include one or more light emitting diodes for emission of the same or different wavelengths of light. The light emitting source 26 emits light which is transmitted through wall 24 into the medium surrounding device 3. The light emitting source is shown in FIG. 2B placed under the coil windings 30, but can be placed elsewhere inside housing 24. In one embodiment, conduit channel 46 inside conduit 44 can include an optical channel for transmitting the light from device 3 along with fluids (e.g., light activatable agents) from fluid reservoir 38. In one embodiment, conduit channel 46 is a double wall clad design with the interior space of the double wall clad channeling light while the outer wall carries the fluid or vice versa.

Coil windings 30 acting as a receiver can receive signals from the initiation energy source. The received signals can contain control instructions. These signals can also be rectified to provide power and recharge battery 32 inside housing 24. The battery 32 supplies power to IC chip 36 and to the light emitting source or emitter 26. In one embodiment, the coil windings 30 are configured to receive signals for power, and the coil 22 is configured to receive the control signals, which are supplied to IC chip 36. Emitter 26 in other embodiments could emit sonic or infrared or RF signals or other energy of a predetermined kind as discussed below.

In one embodiment, IC chip 36 can be an iCode Philips chip. The iCode Philips chip is a compliant transponder that has fast access and read/write times. The higher frequency operation allows communication rates up to 53 kbaud. The iCode Philips chip has flexible memory structure and requires for only a few turns of wire or printed foil tracks for the antenna. The iCode Philips chip has its memory organized as 4-byte blocks with the first two blocks containing a factory programmed 8-byte unique serial number (UID). The other blocks can store programming instructions for operation of the insertion device.

In one embodiment, IC chip 36 serving as an internal controller is mounted on surface 34 of a fluid reservoir 38. Fluid reservoir 38 can hold for example a photoactivatable substance such as a photoactivatable drug or a photoactivatable adhesive. A pump/valve 40 can supply/pump the photoactivatable substance(s) (or other substances such as energy modulation agents and plasmonic agents or optical coupling fluids) from the fluid reservoir 38 to fluid conduit channel 46 inside conduit 44 extending through wall 24 to the outside of device 3. Conduit 44 is shown in FIG. 2B secured to wall 24 of the microdevice by way of wall insert 42, which permits access to and assembly of the interior components of device 3.

In accordance with one embodiment of the invention, insertion device 3 is of a size and weight that permits implantation through an incision in the patient's skin. In some embodiments, such incision may be as small as the puncture hole of a hypodermic needle, with device 3 being implanted through the lumen of such needle. In other embodiments, the incision may be made in conventional manner, but is still preferably (but not necessarily) of relatively small dimensions, e.g., having linear dimensions of no more than about 5 to 10 mm. In accordance with one embodiment of the invention, the fluid reservoir 38 can itself be refilled by way of a surgical connection to the conduit 44.

The insertion device 3 can be implanted by a surgeon having a fiber optic probe with saline flowing therethrough. The fiber optic probe would permit the surgeon to view the nerve or muscle or organ by looking through the fiber optic probe; and when properly positioned, the surgeon can position the electrode(s) 22 around the muscle or nerve or organ.

According to various embodiments of the invention, any type of self-attaching electrode can be used with the insertion device of the present invention. Self-attaching electrodes are described, e.g., in U.S. Pat. No. 4,920,979 (helical electrodes); 4,934,368 (cuff electrodes); or 4,573,481 (helical electrode arrays). Additionally, sutured electrodes or electrode arrays affixed to substrates that are sutured may also be used, such as is shown in U.S. Pat. No. 4,026,300 (woven sheet material coupling) or 4,590,946 (electrodes helically wound and secured to a sutured substrate); although using a sutured electrode configuration defeats one of the advantages of using self-attaching electrodes—ease of implantation.

In yet another embodiment, insertion device 3 can include a sensor (e.g., included in for example in IC Chip 36 which can sense a desired biomedical parameter, e.g., voltage, body position, pressure, magnetic field, chemical parameters such as pH, oxygen, salinity, glucose concentration, or the like, converts such sensed parameter to an electrical signal (if not already an electrical signal), and telemeters such sensed signal to a location outside the body.

In one embodiment, insertion device 3 includes coil 30 which, depending on the particular application, has approximately a number of turns (e.g., 200 turns or more), to provide the necessary induction for the coupling of a magnetic flux associated with an alternating magnetic field so as to couple power to the insertion device from an external source. In one embodiment, the insertion device 3 does not include a coil and relies only on battery 32 for power.

The device housing 24 can be filled with an inert gas. Prior to sealing the housing 24, the inert gas may be introduced into the insertion device, or the insertion device may be assembled in an inert gas atmosphere. The inert gas can be helium, argon, krypton, nitrogen, or a mixture thereof including for example a 10% helium and 90% argon or krypton mixture, or other commonly-used, suitable, biologically-compatible gas. Sealing can be accomplished by way of an epoxy seal/cure.

The insertion device 3 in one embodiment of the invention can be fabricated to include the pump and valve components described in U.S. Pat. No. 5,271,724. The '724 patent describes a microvalve (and process of making) for the administration of medicaments. Of use as the pump/valve 40 here, the '724 patent describes a wafer of silicon or any other material capable of being etched by photolithographic technology bonded to a glass wafer, which in the present invention would serve as fluid reservoir 38. This silicon wafer is machined so as to form an inlet valve, a pump chamber, and an outlet valve (which forms a regulating valve). A glass sealing wafer is bonded to the wafer of silicon above the inlet valve, a piezoelectric disc is formed to the wall of the pump chamber. The inlet valve in the '724 patent and suitable here comprises a membrane of substantially circular form with near its center an orifice and, adjacent to the side of an inlet channel, an annular sealing ring. When this valve is open, the inlet channel is in communication with the pump chamber by the orifice and another orifice. In the '724 patent and suitable here, the outlet valve is equipped with a position detector.

The micropump in one embodiment of the present invention would function as follows. At rest, the inlet and outlet valves are in the closed position. When an electrical voltage is applied, the wall of the pump chamber deforms and the pressure increases therein until the outlet valve opens. The fluid contained in the pump chamber is then driven towards the outlet channel, in this case toward fluid conduit channel 46. During this phase the inlet valve is held closed by the pressure prevailing in the pump chamber. When, however, the electrical potential is removed or reversed, the pressure therein diminishes. This causes closure of the outlet valve and opening of the entry valve. Fluid is thereby drawn into the pump chamber from the fluid reservoir 38.

Alternatively, insertion device(s) 3 of this invention can utilize the micropumping devices and communication devices described in U.S. Pat. No. 6,454,759. The '759 patent describes a microfabricated, fully integrated drug delivery system capable of secreting controlled dosages of multiple drugs over long periods of time (up to a year). The 759 patent device includes a long and narrow shaped implant with a sharp leading edge for implantation under the skin of a human in a manner analogous to a sliver. The implant in the '759 patent (and suitable here for the pump/valve 40) includes: 1) one or more micromachined, integrated, zero power, high and constant pressure generating osmotic engine; 2) low power addressable one-shot shape memory polymer (SMP) valves for switching on the osmotic engine, and for opening drug outlet ports; 3) microfabricated polymer pistons for isolating the pressure source from drug-filled microchannels. The device in the '759 patent (and suitable here as part of or in addition to IC Chip 30) includes an externally mounted controller for controlling on-board electronics which activates the SMP microvalves, etc. of the implant.

Alternatively, insertion device(s) 3 of this invention can utilize the structured LED devices and component structures described in U.S. Pat. Appl. Publ. No. 2011/0168976 for the light emitting elements of insertion device(s) 3. The '976 publication describes use of micro- or nano-structured features that reduce lattice strain and improve p-doping in inorganic LEDs, and facilitate carrier injection and recombination of OLEDs. Here, insertion device(s) 3 of this invention can utilize nano-heteroepitaxy techniques in the '976 publication to produce nanometer (i.e., 5 to <1000 nm, particularly 50-500 nm, e.g., 100 nm feature size emitters. In the present invention, these micro- and nano-emitters would form the basis for light emitting source 26.

In one embodiment, an external controller (e.g. computer 5) communicates to the circuitry in the insertion device 3 by way of broadcast from the initiation energy source 1. For example, the initiation energy source 1 can include an oscillator for broadcasting control information to the microsensor 3. The signal received by the microsensor 3 can be demodulated by a demodulator circuit in IC Chip 36, with a resultant data signal being directed to control the microdevice 3.

The IC Chip 36 serves as an internal controller having a memory programmed with instructions which when executed cause the controller to recognize the initiation signal and to power the LED thereby emitting ultraviolet light interior of the human or animal subject to treat the human or animal subject or emitting ultraviolet light interior to the medium to produce a change in the medium. The IC Chip 36 can already be programmed with instructions or can be programmed by the initiation signal. Such instructions would control the insertion device to at least one of:

1) select which of the light emitting sources 26 in the microdevice 3 to power, thereby providing wavelength specific irradiation, 2) set a power level, duration, and/or duty cycle for LED operation, 3) operate the pump/valve 40 to inject one or more fluids from the insertion device, 4) receive transponder information from the initiation energy source 1 and/other external sources to derive a spatial location of the microdevice 3 within the subject or medium being treated, 5) broadcast spatial information back to computer 5, 6) measure temperature of the insertion device 3 and broadcast temperature information back to computer 5, 7) recognize an initiation signal and power emitter 26 to thereby emit energy of a predetermined type interior of the human or animal subject to treat the human or animal subject or thereby emit the energy of the predetermined type interior to the medium to produce a change in the medium, and/or 8) recognize an initiation signal broadcast into the subject or medium to be treated or recognize an initiation signal programmed into the IC Chip 36 to activate the emitter 26 upon a time, spatial coordinate, or temperature trigger.

Figure 2D:
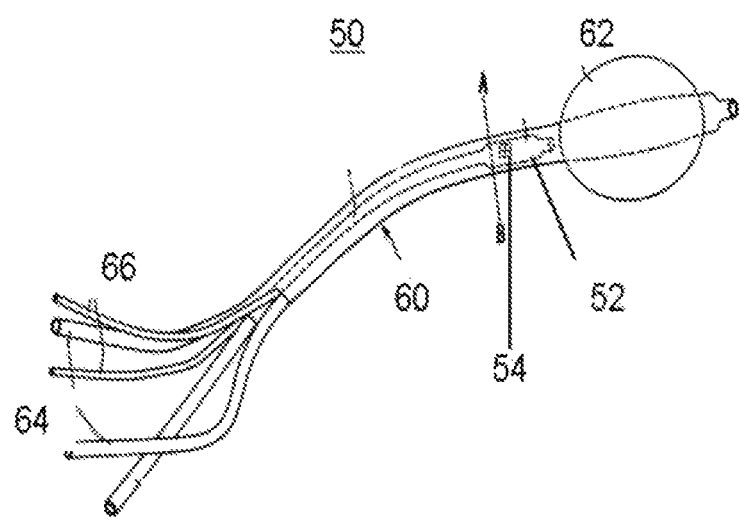
FIG. 2D is a schematic of one embodiment of an insertion device of the invention attached to a catheter.

In one embodiment of the invention, one or more of the insertion device(s) 3 can be attached to a catheter. FIG. 2D is a schematic of one embodiment of an insertion device 3 of the invention attached to catheter 50. Catheter 50 includes an emitter capsule 52 having a microelectronics assembly unit 54. The microelectronics assembly unit 54 includes a UV or visible light emitter, a receiver that receives an initiation signal, and the corresponding circuitry, as described above with regard to FIG. 2B, IC Chip 36, and emitter 26, for example. The microelectronics assembly unit 54 is configured, upon receiving the initiation signal, to power the emitter to thereby emit the energy of the predetermined type into the interior of the human or animal subject to treat the human or animal subject or to effect a change in a biological or non-biological medium. Catheter 50 includes an insertion sleeve 60 having, at a distal end thereof, emitter capsule 52 including one or more of the insertion device(s) 3 of the invention for insertion into a patient.

At the end of the catheter which is inserted first, there can be disposed an inflatable balloon 62 which is shown in the inflated state in FIG. 2D. Cooling water tubes 64 and sensor lines 66 can also be also disposed in the catheter 50.

In one embodiment of the invention, multiple insertion device(s) 3 can be attached to a target tumor site. In one embodiment of the invention, the insertion device 3 provides UV (or visible) light to trigger desirable reactions. As detailed below, UV and visible light emitting diodes and UV and visible light emitting electroluminescent devices are known in the art, and would be useable in the present invention as the emitters 26 for example. Photo-initiation is a known mechanism used in various medicinal, pharmaceutical and chemical reactions. In one embodiment of the invention, the photo initiation can be performed at 360 nm (+/−50 nm) to trigger for example psoralen (and psoralen derivatives with bio-therapeutic functionality) inside a diseased cell or nucleus of the target tumor site.

Photoactivation Treatments of the Invention

Although not intending to be bound by any particular theory or be otherwise limited in any way, the following theoretical discussion of scientific principles and definitions are provided to help the reader gain an understanding and appreciation of the invention.

As used herein, the term "subject" is not intended to be limited to humans, but may also include animals, plants, or any suitable biological organism.

As used herein, the phrase "cell proliferation disorder" refers to any condition where the growth rate of a population of cells is less than or greater than a desired rate under a given physiological state and conditions. Although, preferably, the proliferation rate that would be of interest for treatment purposes is faster than a desired rate, slower than desired rate conditions may also be treated by methods of the invention. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Particularly preferred cell proliferation disorders for treatment using the present methods are cancer, *staphylococcus aureus* (particularly antibiotic resistant strains such as methicillin resistant *staphylococcus aureus* or MRSA), and autoimmune disorders.

As used herein, an "activatable agent" is an agent that normally exists in an inactive state in the absence of an activation signal (e.g., one or more photons). When the agent is activated by an activation signal under activating conditions, the agent is capable of producing a desired pharmacological, cellular, chemical, electrical, or mechanical effect in a medium (i.e. a predetermined change in the medium).

Signals that may be used to activate a corresponding agent may include, but are not limited to, photons of specific wavelengths (e.g. x-rays, ultraviolet, or visible light). For example, an activatable agent, such as a photosensitizer, may be activated by UV-A radiation (e.g., by UV-A radiation generated internally in the medium). For example, an activatable agent, such as a photosensitizer, may be activated by UV-B or UV-C radiation. Once activated, the agent in its active-state may then directly proceed to produce a predetermined change.

When activated, the activatable agent may effect changes that include, but are not limited to an increase in organism activity, a decrease in organism activity, apoptosis, and/or a redirection of metabolic pathways.

As used herein, an "activatable pharmaceutical agent" (alternatively called a "photoactive agent" or PA) is an agent that normally exists in an inactive state in the absence of an activation signal. When the agent is activated, it is capable of affecting the desired pharmacological effect on a target cell (i.e. preferably a predetermined cellular change).

A photoactive compound that achieves its pharmaceutical effect by binding (with mono adducts formation or cross links formation) to certain cellular structure in its active state may require physical proximity to the target cellular structure when the activation signal is delivered. Some examples of activating conditions may include, but are not limited to, temperature, pH, location, state of the cell, presence or absence of co-factors. Selection of an activatable pharmaceutical agent greatly depends on a number of factors such as the desired cellular change, the desired form of activation, as well as the physical and biochemical constraints that may apply.

When activated for example by UV light (or visible light) from the insertion devices, the activatable pharmaceutical agent may affect cellular changes that include, but are not limited to, apoptosis, lysis, redirection of metabolic pathways, up-regulation of certain genes, down-regulation of certain genes, secretion of cytokines, alteration of cytokine receptor responses, production or modulation of reactive oxygen species or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include modulation of or releasing metabolites upon activation to interfere with normal metabolic pathways, releasing chemical signals (e.g. agonists or antagonists) upon activation to alter the targeted cellular response, and other suitable biochemical or metabolic alterations.

In one preferred embodiment, the activatable pharmaceutical agent is capable of chemically binding to the DNA or mitochondriat at a therapeutically effective amount. In this embodiment, the activatable pharmaceutical agent, preferably a photoactivatable agent, is exposed in situ to light internally generated for example by CR and/or an energy modulation agent.

An activatable agent may be a small molecule; a biological molecule such as a protein, a nucleic acid or lipid; a supramolecular assembly; a nanoparticle; a nanostructure, or combinations thereof; or any other molecular entity having a pharmaceutical activity once activated.

Additional photoactive agents include, but are not limited to, carbene precursors, nitrene precursors, thio derivatives, benzophenones, and halogenated pyrimidines. Such photochemistries are routinely employed to achieve protein-DNA photocross-links but none has been achieved using an indirect method as presented herein, for example where X-Ray radiation is converted to UV radiation to activate the species and achieve DNA photocross-links.

Endogenously-based derivatives include synthetically derived analogs and homologs of endogenous photoactivated molecules, which may have or lack lower (1 to 5 carbons) alkyl or halogen substituents of the photosensitizers from which they are derived, and which preserve the function and substantial non-toxicity. Endogenous molecules are inherently non-toxic and may not yield toxic photoproducts after photoradiation.

The nature of the predetermined cellular change will depend on the desired pharmaceutical outcome. Exemplary cellular changes may include, but are not limited to, morphologic changes, apoptosis, necrosis, up-regulation of certain genes, down-regulation of certain genes, modulation of or secretion of cytokines, alteration of cytokine receptor responses, or a combination thereof.

When activated for example by UV light (or visible light) from the insertion devices, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, production of reactive oxygen species or combinations thereof.

A preferred method of treating a cell proliferation disorder of the invention administers a photoactivatable agent to a patient, stimulates the photoactivatable agent by UV light (or visible light) from the insertion devices to induce cell damage (or kill), and generates an auto vaccine effect.

Additionally, energy modulation agents may be included in the medium to be treated. The energy modulation agents could be used to supplement the internally generated UV light by down-conversion of the UV light into UV light at a different wavelength or into visible or infrared light.

As used here, an "energy modulation agent" refers to an agent that is capable of receiving an energy input from a source and then re-emitting a different energy to a receiving target. Energy transfer among molecules may occur in a number of ways. The form of energy may be electronic, thermal, electromagnetic, kinetic, or chemical in nature. Energy may be transferred from one molecule to another (intermolecular transfer) or from one part of a molecule to another part of the same molecule (intramolecular transfer). For example, a modulation agent may receive electromagnetic energy and re-emit the energy in the form of thermal energy which otherwise contributes to heating the environment in vicinity of the light emission. Some modulation agents may have a very short energy retention time (on the order of fs, e.g. fluorescent molecules) whereas others may have a very long half-life (on the order of minutes to hours, e.g. luminescent or phosphorescent molecules). The energy modulation agent materials can preferably include any materials that can absorb X-Ray and/or UV light and emit light at a different wavelength in order to excite the PA molecule.

Quantum dots, semiconductor nanostructures and various materials related to quantum dots, semiconductor materials, etc. can be used as energy modulation agents. Scintillator materials can be used as energy modulation agents. Various scintillator materials can be used as energy modulation agents emitting luminescence emission, which can be used to excite the PA system.

Suitable energy modulation agents include, but are not limited to, a phosphor, a scintillator, a biocompatible fluorescing metal nanoparticle, fluorescing dye molecule, gold nanoparticle, quantum dots, such as a water soluble quantum dot encapsulated by polyamidoamine dendrimers, a luciferase, a biocompatible phosphorescent molecule, a combined electromagnetic energy harvester molecule, a lanthanide chelate capable of intense luminescence, metals (gold, silver, etc); semiconductor materials; organic solids, metal complexes, inorganic solids, crystals, rare earth materials (lanthanides), polymers, and materials that exhibit excitonic properties.

In a preferred embodiment, the energy modulation agents include down converters (such as for example phosphors which can convert UV light from the insertion device(s) 3 into light at a different wavelength including for example visible light. These down converters when used in combination can activate a variety of UV-stimulated photoreactions as well as activate any visible light activated reactions.

Examples of luminescing particles (down converters) can include gold particles (such as for example the nanoparticles of gold), BaFBr:Eu particles, CdSe particles, $Y_2O_3:Eu^{3+}$ particles, and/or other known stimulated luminescent materials such as for example $ZnS:Mn^{2+}$; $ZnS:Mn^{2+}$, $Yb^{3+}$, $Y_2O_3$: $Eu^{3+}$; $BaFBr:Tb^{3+}$; and $YF_3:Tb^{3}+$. More specific examples of the downconverters include, but are not limited to: $BaFCl:Eu^{2+}$, $BaSO_4^-:Eu^{2+}$, $LaOBr:Tm^{3+}$, $YTaO_4$, $YTaO_4:Nb$ (*), $CaWO_4$, $LaOBr:Tb^{3+}$, $Y_2O_2S:Tb^{3+}$, ZnS:Ag, (Zn,Cd)S:Ag, $Gd_2O_2S:Tb^{3+}$, $La_2O_2S:Tb^{3+}$.

In one aspect of the invention, a downconverting energy modulation agent can comprise inorganic particulates selected from the group consisting of: metal oxides; metal sulfides; doped metal oxides; and mixed metal chalcogenides. In one aspect of the invention, the downconverting material can comprise at least one of $Y_2O_3$, $Y_2O_2S$, $NaYF_4$, $NaYbF_4$, YAG, YAP, $Nd_2O_3$, $LaF_3$, $LaCl_3$, $La_2O_3$, $TiO_2$, $LuPO_4$, $YVO_4$, $YbF_3$, $YF_3$, Na-doped $YbF_3$, ZnS; ZnSe; MgS; CaS; $CaWO_4$, $CaSiO_2:Pb$, and alkali lead silicate including compositions of $SiO_2$, $B_2O_3$, $Na_2O$, $K_2O$, PbO, MgO, or Ag, and combinations or alloys or layers thereof. In one aspect of the invention, the downconverting material can include a dopant including at least one of Er, Eu, Yb, Tm, Nd, Mn Tb, Ce, Y, U, Pr, La, Gd and other rare-earth species or a combination thereof. The dopant can be included at a concentration of 0.01%-50% by mol concentration.

In one aspect of the invention, the downconverting energy modulation agent can comprise materials such as ZnSeS:Cu, Ag, Ce, Tb; CaS:Ce,Sm; $La_2O_2S:Tb$; $Y_2O_2S:Tb$; $Gd_2O_2S$: Pr, Ce, F; $LaPO_4$. In other aspects of the invention, the downconverting material can comprise phosphors such as ZnS:Ag and ZnS:Cu, Pb. In other aspects of the invention, the downconverting material can be alloys of the ZnSeS family doped with other metals. For example, suitable materials include $ZnSe_xS_y$:Cu, Ag, Ce, Tb, where the following x, y values and intermediate values are acceptable:

x:y; respectively 0:1; 0.1:0.9; 0.2:0.8; 0.3:0.7; 0.4:0.6; 0.5:0.5; 0.6:0.4; 0.7:0.3; 0.8:0.2; 0.9:0.1; and 1.0:0.0.

In other aspects of the invention, the downconverting energy modulation agent can be materials such as sodium yttrium fluoride (NaYF$_4$), lanthanum fluoride (LaF$_3$), lanthanum oxysulfide (La$_2$O$_2$S), yttrium oxysulfide (Y$_2$O$_2$S), yttrium fluoride (YF$_3$), yttrium gallate, yttrium aluminum garnet (YAG), gadolinium fluoride (GdF$_3$), barium yttrium fluoride (BaYF$_5$, BaY$_2$F$_8$), gadolinium oxysulfide (Gd$_2$O$_2$S), calcium tungstate (CaWO$_4$), yttrium oxide:terbium (Yt$_2$O$_3$Tb), gadolinium oxysulphide:europium (Gd$_2$O$_2$S:Eu), lanthanum oxysulphide:europium (La$_2$O$_2$S:Eu), and gadolinium oxysulphide:promethium, cerium, fluorine (Gd$_2$O$_2$S:Pr,Ce,F), YPO$_4$:Nd, LaPO$_4$:Pr, (Ca,Mg)SO$_4$:Pb, YBO$_3$:Pr, Y$_2$SiO$_5$:Pr, Y$_2$Si$_2$O$_7$:Pr, SrLi$_2$SiO$_4$:Pr,Na, and CaLi$_2$SiO$_4$:Pr.

In other aspects of the invention, the downconverting energy modulation agent can be near-infrared (NIR) downconversion (DC) phosphors such as KSrPO$_4$:Eu$^{2+}$, Pr$^{3+}$, or NaGdF$_4$:Eu or Zn$_2$SiO$_4$:Tb$^{3+}$, Yb$^{3+}$ or β-NaGdF$_4$ co-doped with Ce$^{3+}$ and Tb$^{3+}$ ions or Gd$_2$O$_2$S:Tm or BaYF$_5$:Eu$^{3+}$ or other down converters which emit NIR from visible or UV light exposure (as in a cascade from UV to NIR).

In one embodiment of the invention, some of the phosphors noted above can absorb in the 390 to 410 nm range and then in turn down convert the UV radiation into red shifted emissions for activation in the visible. As an example, the excitation wavelength can be between 300 nm and 450 nm, and the emission can be centered around 650 nm as is the case for 6MgO. As$_2$O$_5$:Mn$^{4+}$ and for 3.5MgO 0.5MgF$_2$ GeO$_2$:Mn$^{2+}$.

In various embodiments of the invention, the following luminescent polymers are also suitable as energy modulation agents: poly(phenylene ethynylene), poly(phenylene vinylene), poly(p-phenylene), poly(thiophene), poly(pyridyl vinylene), poly(pyrrole), poly(acetylene), poly(vinyl carbazole), poly(fluorenes), and the like, as well as copolymers and/or derivatives thereof.

While many of the energy modulation agents of the invention are down conversion agents (i.e. where higher energy excitation produces lower energy emission), U.S. Pat. No. 7,008,559 (the entire contents of which are incorporated herein by reference) describes the upconversion performance of ZnS where excitation at 767 nm produces emission in the visible range. The materials described in U.S. Pat. No. 7,008,559 including the ZnS as well as Er$^{3+}$ doped BaTiO$_3$ nanoparticles and Yb$^{3+}$ doped CsMnCl$_3$ are suitable in various embodiments of the invention. Here, the up converters can permit further tailoring of an energy cascade producing a targeted wavelength of interest by way of UV down conversion followed by up conversion of the down-converted visible or infrared wavelengths.

Accordingly, in various embodiments of the invention, the up converters can be used in combination with the down converters (or mixtures of down converters) or in combination with various up converters. Various up converters suitable for this invention include CdTe, CdSe, ZnO, CdS, Y$_2$O$_3$, MgS, CaS, SrS and BaS. Such up conversion materials may be any semiconductor and more specifically, but not by way of limitation, sulfide, telluride, selenide, and oxide semiconductors and their nanoparticles, such as Zn$_{1-x}$Mn$_x$S$_y$, Zn$_{1-x}$Mn$_x$Se$_y$, Zn$_{1-x}$Mn$_x$Te$_y$, Cd$_{1-x}$MnS$_y$, Cd$_{1-x}$Mn$_x$Se$_y$, Cd$_{1-x}$Mn$_x$Te$_y$, Pb$_{1-x}$Mn$_x$S$_y$, Pb$_{1-x}$Mn$_x$Se$_y$, Pb$_{1-x}$Mn$_x$Te$_y$, Mg$_{1-x}$MnS$_y$, Ca$_{1-x}$Mn$_x$S$_y$, Ba$_{1-x}$Mn$_x$S$_y$ and Sr$_{1-x}$, etc. (wherein, 0<x≤1, and 0<y≤1). Complex compounds of the above-described semiconductors are also contemplated for use in the invention—e.g. (M$_{1-z}$N$_z$)$_{1-x}$Mn$_x$A$_{1-y}$B$_y$ (M=Zn, Cd, Pb, Ca, Ba, Sr, Mg; N=Zn, Cd, Pb, Ca, Ba, Sr, Mg; A=S, Se, Te, O; B=S, Se, Te, O; 0<x≤1, 0<y≤1, 0<z≤1). Two examples of such complex compounds are Zn$_{0.4}$Cd$_{0.4}$Mn$_{0.2}$S and Zn$_{0.9}$Mn$_{0.1}$S$_{0.8}$Se$_{0.2}$. Additional conversion materials include insulating and nonconducting materials such as BaF$_2$, BaFBr, and BaTiO$_3$, to name but a few exemplary compounds. Transition and rare earth ion co-doped semiconductors suitable for the invention include sulfide, telluride, selenide and oxide semiconductors and their nanoparticles, such as ZnS; Mn; Er; ZnSe; Mn, Er; MgS; Mn, Er; CaS; Mn, Er; ZnS; Mn, Yb; ZnSe; Mn,Yb; MgS; Mn, Yb; CaS; Mn,Yb etc., and their complex compounds: (M$_{1-z}$N$_z$)$_{1-x}$(Mn$_q$R$_{1-q}$)$_x$A$_{1-y}$B$_y$ (M=Zn, Cd, Pb, Ca, Ba, Sr, Mg; N=Zn, Cd, Pb, Ca, Ba, Sr, Mg; A=S, Se, Te, O; B=S, . . . 0<z≤1, o<q≤1).

Indeed, some nanoparticles such as ZnS:Tb$^{3+}$, Er$^{3+}$; ZnS:Tb$^{3+}$; Y$_2$O$_3$:Tb$^{3+}$; Y$_2$O$_3$:Tb$^{3+}$, Er3+; ZnS:Mn$^{2+}$; ZnS:Mn, Er$^{3+}$ are known in the art to have two functions, capable of functioning for both down-conversion luminescence and upconversion luminescence.

To reduce the toxicity, the generation of free radical species or to make these nanoparticles or the insertion device(s) bio-inert or biocompatible, one embodiment of the invention described here coats the nanoparticles and/or or the insertion device(s) with silica. Silica is used as a coating material in a wide range of industrial colloid products from paints and magnetic fluids to high-quality paper coatings. Further, silica is both chemically and biologically inert and also is optically transparent. Other coatings suitable for this invention include a polymethyl methacrylate (PMMA) coating and an ethyl-cellulose coating. Once coated or encapsulated, the insertion device(s) are preferably sterilized and packaged in a sterile environment and suitable for insertion in a patient or subject. Other coating such as Diamond Like Coating such as those derived from Physical Vapor Deposition reactors can be used. Coatings derived from Chemical Vapor Deposition (like nano-crystalline diamonds) are possible. Other coatings such as those derived from Sol-Gel Processes (like a silicate coating) are desirable. Various coating methods can be used to coat the microdevices prior to insertion inside the body.

Additionally, the energy modulation agent can be used alone or as a series of two or more energy modulation agents wherein the energy modulation agents provide an energy cascade from the light of the phosphors or scintillators. Thus, the first energy modulation agent in the cascade will absorb the UV light, convert it to a different energy which is then absorbed by the second energy modulation in the cascade, and so forth until the end of the cascade is reached with the final energy modulation agent in the cascade emitting the energy necessary to activate the activatable pharmaceutical agent.

In one embodiment of the invention, a chemical reaction cascade can be triggered. The UV or visible light from the insertion device(s) 3 can activate a chemical which in turn can activate a bio-therapeutic in parallel to or independent of a photonic pathway.

The energy modulation agents or the photoactivatable agent may further be coupled to a carrier for cellular targeting purposes. For example, a UV or visible light emitting insertion device may be concentrated in the tumor site by physical insertion.

In general, photoactivatable agents may be stimulated by light from UV or visible from the insertion device(s) 3 of the present invention, leading to subsequent irradiation, resonance energy transfer, exciton migration, electron injection, or chemical reaction, to an activated energy state that is capable of effecting the predetermined cellular change desired. In a one embodiment, the photoactivatable agent, upon activation, binds to DNA or RNA or other structures in a cell. The activated energy state of the agent is capable of causing damage to cells, inducing apoptosis. The mechanism of apoptosis is associated with an enhanced immune response that reduces the growth rate of cell proliferation disorders and may shrink solid tumors, depending on the state of the patient's immune system, concentration of the agent in the tumor, sensitivity of the agent to stimulation, and length of stimulation.

When drug molecules absorb excitation light, electrons undergo transitions from the ground state to an excited electronic state. The electronic excitation energy subsequently relaxes via radiative emission (luminescence) and radiationless decay channels. When a molecule absorbs excitation energy, it is elevated from $S_o$ to some vibrational level of one of the excited singlet states, $S_n$, in the manifold $S_1, \ldots, S_n$. In condensed media (tissue), the molecules in the $S_n$ state deactivate rapidly, within $10^{-13}$ to $10^{-11}$ s via vibrational relaxation (VR) processes, ensuring that they are in the lowest vibrational levels of $S_n$ possible. Since the VR process is faster than electronic transitions, any excess vibrational energy is rapidly lost as the molecules are deactivated to lower vibronic levels of the corresponding excited electronic state. This excess VR energy is released as thermal energy to the surrounding medium. From the $S_n$ state, the molecule deactivates rapidly to the isoenergetic vibrational level of a lower electronic state such as $S_{n-1}$ vian internal conversion (IC) process. IC processes are transitions between states of the same multiplicity. The molecule subsequently deactivates to the lowest vibronic levels of $S_{n-1}$ via VR process. By a succession of IC processes immediately followed by VR processes, the molecule deactivates rapidly to the ground state $S_1$. This process results in excess VR and IC energy released as thermal energy to the surrounding medium leading to the overheating of the local environment surrounding the light absorbing drug molecules. The heat produced results in local cell or tissue destruction. The light absorbing species include natural chromophores in tissue or exogenous dye compounds such as indocyanine green, naphthalocyanines, and porphyrins coordinated with transition metals and metallic nanoparticles and nanoshells of metals. Natural chromophores, however, suffer from very low absorption. The choice of the exogenous photothermal agents is made on the basis of their strong absorption cross sections and highly efficient light-to-heat conversion. This feature greatly minimizes the amount of energy needed to induce local damage of the diseased cells, making therapy method less invasive.

Photodynamic Therapy (PDT) with the Insertion Devices of this Invention

PDT is a relatively new light-based treatment, which has recently been approved by the United States Food & Drug Administration (FDA) for the treatment of both early and late-stage lung cancer. Other countries have approved PDT for treatment of various cancers as well. Unlike chemotherapy, radiation, and surgery, PDT is useful in treating all cell types, whether small cell or non-small cell carcinoma. PDT involves treatment of diseases such as cancer using light action on a special photoactive class of drugs, by photodynamic action in vivo to destroy or modify tissue [Dougherty T. J. and Levy J. G., "Photodynamic Therapy and Clinical Applications", in *Biomedical Photonics Handbook*, Vo-Dinh T., Ed., CRC Press, Boca Raton Fla. (2003)]. PDT, which was originally developed for treatment of various cancers, has now been used to include treatment of pre-cancerous conditions, e.g. actinic keratoses, high-grade dysplasia in Barrett's esophagus, and non-cancerous conditions, e.g. various eye diseases, e.g. age related macular degeneration (AMD). Photodynamic therapy (PDT) is approved for commercialization worldwide both for various cancers (lung, esophagus) and for AMD. In one embodiment of the present invention, the insertion devices described above can directly activate the PA drug or directly excite endogenous oxygen. For example, in one embodiment, the insertion devices emit visible light which interacts with a photosensitizer (see discussion below) which in turn generates singlet oxygen or other radical species in the vicinity of the diseased site. In another embodiment, the insertion devices emit ultraviolet or visible light which generates (from the endogenous oxygen) singlet oxygen or other radical species in the vicinity of the diseased site.

The PDT process requires three elements: (1) a PA drug (i.e., photosensitizer), (2) light that can excite the photosensitizer and (3) endogenous oxygen. The putative cytotoxic agent is singlet oxygen, an electronically excited state of ground state triplet oxygen formed according to the Type II photochemical process, as follows.

$PA + h\nu \rightarrow {}^1PA^*(S)$ Excitation ${}^1PA^*(S) \rightarrow {}^3PA^*(T)$ Intersystem crossing for singlet to triplet state ${}^3PA^*(T) + O_2 \rightarrow {}^1O^*_2 + PA$ Energy transfer from the drug to singlet oxygen where PA=photo-active drug at the ground state; ${}^1PA^*(S)$=excited singlet state; ${}^3PA^*(T)$=excited triplet state; ${}^1O^*_2$=singlet excited state of oxygen Because the triplet state has a relatively long lifetime (μsec to seconds) only photosensitizers that undergo efficient intersystem crossing to the excited triplet state will have sufficient time for collision with oxygen in order to produce singlet oxygen. The energy difference between ground state and singlet oxygen is 94.2 kJ/mol and corresponds to a transition in the near-infrared at 1270 nm. Most PA photosensitizers in clinical use have triplet quantum yields in the range of 40-60% with the singlet oxygen yield being slightly lower. Competing processes include loss of energy by deactivation to ground state by fluorescence or internal conversion (loss of energy to the environment or surrounding medium).

However, while a high yield of singlet oxygen is desirable it is by no means sufficient for a treatment to be clinically useful. Pharmacokinetics, pharmacodynamics, stability in vivo and acceptable toxicity play critical roles as well [Henderson B W, Gollnick S O, "*Mechanistic Principles of Photodynamic Therapy*", in *Biomedical Photonics Handbook*, Vo-Dinh T., Ed., CRC Press, Boca Raton Fla. (2003)]. For example, it is desirable to have relatively selective uptake in the tumor or other tissue being treated relative to the normal tissue that necessarily will be exposed to the exciting light as well. Pharmacodynamic issues such as the subcellular localization of the photosensitizer may be important as certain organelles appear to be more sensitive to PDT damage than others (e.g. the mitochondria). An important mechanism associated with PDT drug activity involves apoptosis in cells. Upon absorption of light, the photosensitiser (PS) or the UV light initiates chemical reactions that lead to the direct or indirect production of cytotoxic species such as radicals and singlet oxygen. The reaction of the cytotoxic species with subcellular organelles and macromolecules (proteins, DNA, etc) can lead to apoptosis and/or necrosis of the cells hosting the PDT drug. The preferential accumulation of PDT drug molecules in cancer cells combined with the localized delivery of light to the tumor possible with the insertion device(s) 3 of the present invention, may result in the selective destruction of a cancerous lesion. Compared to other traditional anticancer therapies, PDT does not involve generalized destruction of healthy cells. In addition to direct cell killing, PDT can also act on the vasculature, reducing blood flow to the tumor causing its necrosis. In particular cases, it can be used as a less invasive alternative to surgery.

There are several chemical species used for PDT including porphyrin-based sensitizers. A purified hematoporphyrin derivative, Photofrin®, has received approval of the US Food and Drug Administration. Porphyrins are generally used for tumors on or just under the skin or on the lining of internal organs or cavities because theses drug molecules absorbs light shorter than 640 nm in wavelength. For tumors occurring deep in tissue, second generation sensitizers, which have absorbance in the NIR region, such as porphyrin-based systems [R. K. Pandey, "*Synthetic Strategies in designing Porphyrin-Based* Photosensitizers', in *Biomedical Photonics Handbook*, Vo-Dinh T., Ed., CRC Press, Boca Raton Fla. (2003)], chlorines, phthalocyanine, and naphtalocyanine have been investigated. Conventional PDT is known to retain several photosensitizers in tumors for a longer time than in normal tissues, thus offering for the present invention potential improvement in treatment selectivity. See Corner C., "Determination of [3H]- and [14C] hematoporphyrin derivative distribution in malignant and normal tissue," Cancer Res 1979, 3 9: 146-151; Young S W, et al., "Lutetium texaphyrin (PCI-0123) a near-infrared, water-soluble photosensitizer," Photochem Photobiol 1996, 63:892-897; and Berenbaum M C, et al., "Meso-Tetra(hydroxyphenyl)porphyrins, a new class of potent tumor photosensitisers with favourable selectivity," Br J Cancer 1986, 54:717-725. Photodynamic therapy uses light of a specific wavelength to activate the photosensitizing agent. Various light sources have been developed for PDT, which include dye lasers and diode lasers. Light generated by lasers can be coupled to optical fibers that allow the light to be transmitted to the desired site. See Pass 1-11, "Photodynamic therapy in oncology: mechanisms and clinical use," J Natl Cancer Inst 1993, 85:443-456. According to researchers, the cytotoxic effect of PDT is the result of photooxidation reactions, as disclosed in Foote C S, "Mechanisms of photooxygenation," Proa Clin Biol Res 1984, 170:3-18. Light causes excitation of the photosensitizer, in the presence of oxygen, to produce various toxic species, such as singlet oxygen and hydroxyl radicals.

Photoactivation Treatments with the Insertion Devices of the Invention

For the treatment of cell proliferation disorders, an initiation energy source can provide an initiation energy that the light emitting insertion device(s) 3 receive, instructing these devices to emit light or to emit some form of energy which activates an activatable pharmaceutical agent to treat target cells within a subject. In one embodiment, the emitted light or energy is applied indirectly to the activatable pharmaceutical agent, preferably in proximity to the target cells. Within the context of the present invention, the phrase "applied indirectly" (or variants of this phrase, such as "applying indirectly", "indirectly applies", "indirectly applied", "indirectly applying", etc.), when referring to the application of the initiation energy, means the penetration by the initiation energy into the subject beneath the surface of the subject and to the insertion device(s) 3 within a subject.

Although not intending to be bound by any particular theory or be otherwise limited in any way, the following theoretical discussion of scientific principles and definitions are provided to help one gain an understanding and appreciation of the present invention.

As used herein, the term "subject" is not intended to be limited to humans, but may also include animals, plants, or any suitable biological organism.

As used herein, the phrase "cell proliferation disorder" refers to any condition where the growth rate of a population of cells is less than or greater than a desired rate under a given physiological state and conditions. Although, preferably, the proliferation rate that would be of interest for treatment purposes is faster than a desired rate, slower than desired rate conditions may also be treated by methods of the present invention. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Particularly preferred cell proliferation disorders for treatment using the present methods are cancer, *staphylococcus aureus* (particularly antibiotic resistant strains such as methicillin resistant *staphylococcus aureus* or MRSA), and autoimmune disorders.

Activation of the agent may be as simple as delivering the signal to the agent or may further premise on a set of activation conditions. For example, in the former case, an activatable pharmaceutical agent, such as a photosensitizer, may be activated by UV-A radiation (e.g., UV-A light from the insertion device(s) 3 of the invention). Once activated, the agent in its active-state may then directly proceed to effect a cellular change.

Where activation may further premise upon other conditions, mere delivery of the activation signal may not be sufficient to bring about the desired cellular change. For example, a photoactive compound that achieves its pharmaceutical effect by binding to certain cellular structure in its active state may require physical proximity to the target cellular structure when the activation signal is delivered. For such activatable agents, delivery of the activation signal under non-activating conditions will not result in the desired pharmacologic effect. Some examples of activating conditions may include, but are not limited to, temperature, pH, location, state of the cell, presence or absence of co-factors. Selection of an activatable pharmaceutical agent greatly depends on a number of factors such as the desired cellular change, the desired form of activation, as well as the physical and biochemical constraints that may apply.

When activated, the activatable pharmaceutical agent may affect cellular changes that include, but are not limited to, apoptosis, redirection of metabolic pathways, up-regulation of certain genes, down-regulation of certain genes, secretion of cytokines, alteration of cytokine receptor responses, production of reactive oxygen species or combinations thereof.

The mechanisms by which an activatable pharmaceutical agent may achieve its desired effect are not particularly limited. Such mechanisms may include direct action on a predetermined target as well as indirect actions via alterations to the biochemical pathways.

A preferred direct action mechanism is by binding the photoactivatable agent (e.g., psoralen or an alkylating agent to be discuss in detail later) to a critical cellular structure such as nuclear DNA, mRNA, rRNA, ribosome, mitochondrial DNA, or any other functionally important structures. Indirect mechanisms may include releasing metabolites upon activation to interfere with normal metabolic pathways, releasing chemical signals (e.g. agonists or antagonists) upon activation to alter the targeted cellular response, and other suitable biochemical or metabolic alterations.

The treatment can be by those methods described in U.S. application Ser. No. 11/935,655, filed Nov. 6, 2007 (incorporated by reference), or by a modified version of a conventional treatment such as PDT, but using a plasmonics-active agent to enhance the treatment by modifying or enhancing the energy emitted from insertion device(s) 3.

In one embodiment, the activatable pharmaceutical agent is capable of chemically binding to the DNA or mitochondriat a therapeutically effective amount. In this embodiment, the activatable pharmaceutical agent, preferably a photoactivatable agent, is exposed in situ to an activating energy emitted from insertion device(s) 3.

The activatable agent may be derived from a natural or synthetic origin. Any such molecular entity that may be activated by a suitable activation signal source to effect a predetermined cellular change may be advantageously employed in the present invention. Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substituents of the photosensitizers from which they are derived, and which preserve the function and substantial non-toxicity. Endogenous molecules are inherently non-toxic and may not yield toxic photoproducts after photoradiation.

Table 1 below lists some photoactivatable molecules capable of being photoactivated to induce an auto vaccine effect.

| SSET and TTET rate constants for bichromophoric peptides | | | | | | | | | | |
|---|---|---|---|---|---|---|---|---|---|---|
| Compound | $\lambda_{ex}$ (nm) | $E_{SSET}$ | $k_s$ of donor ($s^{-1}$) | $k_{SSET}$ ($s^{-1}$) | $k_{SSET}(s^{-1})$ (Average) | $R_0$ (Å) | $R$ (Å) | $R_{model}$(Å) (Average) | $E_{TTET}$ | $k_{TTET}$ ($s^{-1}$) |
| 1B | 224 | 96.3 | $9.5 \times 10^5$ | $2.44 \times 10^6$ | $1.87 \times 10^6$ | 14.7 | 9 | 9.5 | | |
|  | 266 | 95 | | $1.8 \times 10^6$ | | | | | 2.5 | $5 \times 10^2$ |
|  | 280 | 94 | | $1.36 \times 10^6$ | | | | | | |
| 1A | 224 | 80 | $9.5 \times 10^5$ | $3.8 \times 10^7$ | $3.67 \times 10^7$ | 14.7 | 11.8 | 14.1 | | |
|  | 266 | 79 | | $3.6 \times 10^7$ | | | | | 2 | $3.6 \times 10^2$ |
|  | 280 | 79 | | $3.6 \times 10^7$ | | | | | | |
| 2B | 224 | 77 | $9.5 \times 10^5$ | $3.1 \times 10^7$ | $3.9 \times 10^7$ | 14.7 | 11.9 | 6.5 | | |
|  | 266 | 81 | | $3.9 \times 10^7$ | | | | | 32 | $9.4 \times 10^3$ |
|  | 280 | 83 | | $4.7 \times 10^7$ | | | | | | |
| 2A | 224 | 69 | $9.5 \times 10^5$ | $2.1 \times 10^7$ | $3 \times 10^7$ | 14.7 | 12.2 | 8.1 | 74.3 | $5.7 \times 10^4$ |
|  | 266 | 80 | | $3.7 \times 10^7$ | | | | | | |
|  | 280 | 77 | | $3.2 \times 10^7$ | | | | | | |

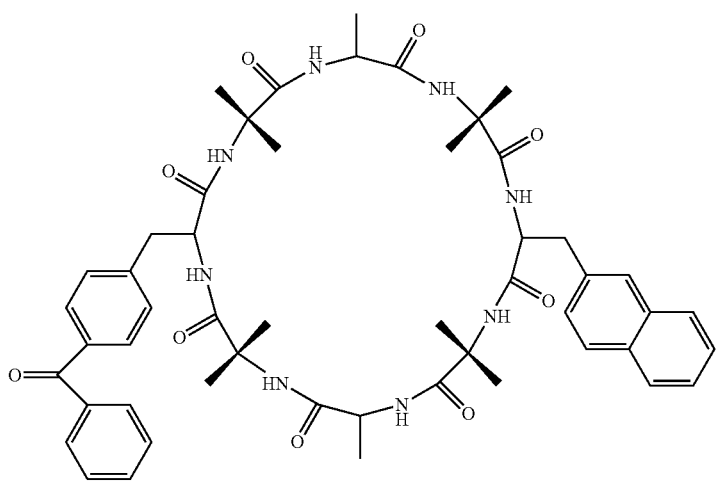

1A

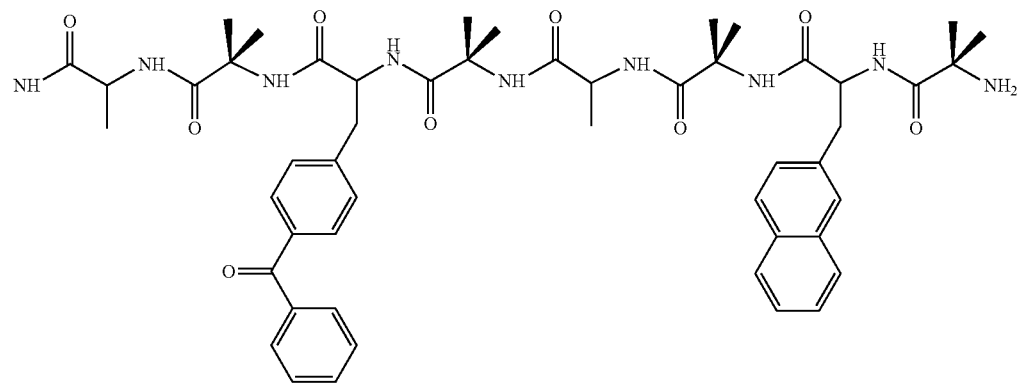
1B
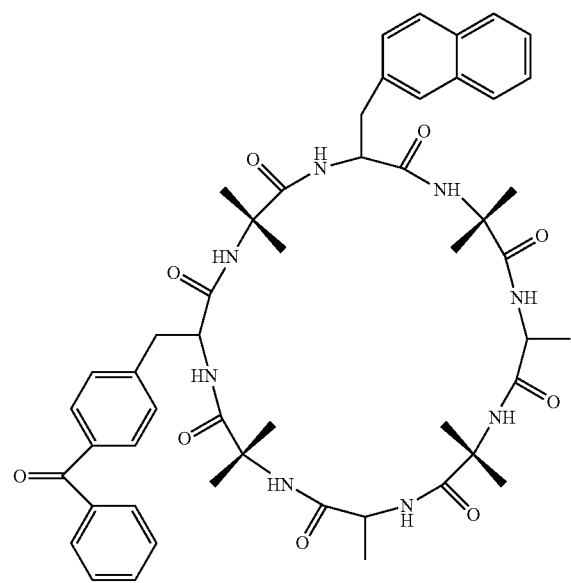
1C
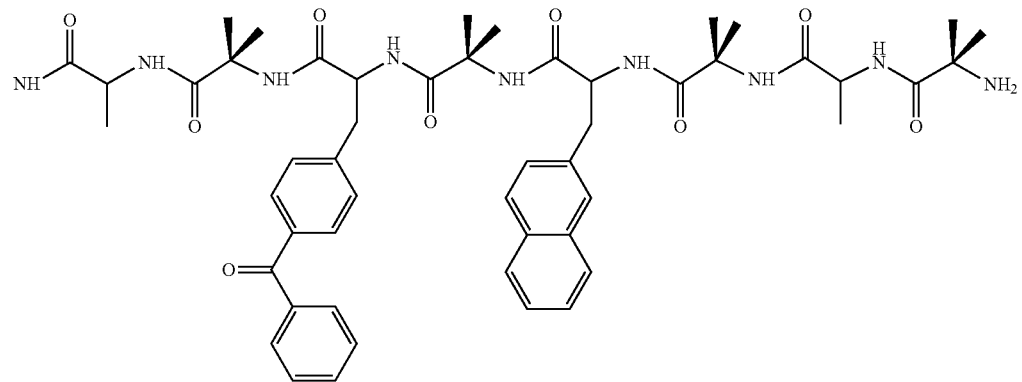
2B

Table 2 below lists some additional endogenous photo-activatable molecules.

Biocompatible, Endogenous Fluorophore Emitters.

| Endogenous Fluorophores | Excitation Max. (nm) | Emission Max. (nm) |
|---|---|---|
| Amino acids: | | |
| Tryptophan | 280 | 350 |
| Tyrosine | 275 | 300 |
| Phenylalanine | 260 | 280 |
| Structural Proteins: | | |
| Collagen | 325, 360 | 400, 405 |
| Elastin | 290, 325 | 340, 400 |
| Enzymes and Coenzymes: | | |
| flavin adenine dinucleotide | 450 | 535 |
| reduced nicotinamide dinucelotide | 290, 351 | 440, 460 |
| reduced nicotinamide dinucelotide phosphate | 336 | 464 |
| Vitamins: | | |
| Vitamins A | 327 | 510 |
| Vitamins K | 335 | 480 |
| Vitamins D | 390 | 480 |
| Vitamins $B_6$ compounds: | | |
| Pyridoxine | 332, 340 | 400 |
| Pyridoxamine | 335 | 400 |
| Pyridoxal | 330 | 385 |
| Pyridoxic acid | 315 | 425 |
| Pyridoxal phosphate | 5'-330 | 400 |
| Vitamin $B_{12}$ | 275 | 305 |
| Lipids: | | |
| Phospholipids | 436 | 540, 560 |
| Lipofuscin | 340-395 | 540, 430-460 |
| Ceroid | 340-395 | 430-460, 540 |
| Porphyrins | 400-450 | 630, 690 |

The nature of the predetermined cellular change will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, or a combination thereof.

Energy from light emitted from insertion device(s) 3 of the invention may be transferred from one molecule to another (intermolecular transfer) or from one part of a molecule to another part of the same molecule (intramolecular transfer). For example, the received electromagnetic energy may be converted into thermal energy. Energy transfer processes are also referred to as molecular excitation.

Additionally, energy modulation agents may be included in the medium to be treated. The energy modulation agents may upon receiving of light from insertion device(s) 3 of the invention re-emit a light specific to a desired photo-driven reaction. Energy modulation agents can have a very short energy retention time (on the order of fs-ns, e.g. fluorescent molecules) whereas others may have a very long half-life (on the order of seconds to hours, e.g. luminescent inorganic molecules or phosphorescent molecules). Various exemplary uses of these are described below in preferred embodiments.

The modulation agents may further be coupled to a carrier for cellular targeting purposes. For example, a biocompatible molecule, such as a fluorescing metal nanoparticle or fluorescing dye molecule that emits in the UV-A band, may be selected as the energy modulation agent.

Light from insertion device(s) 3 of the invention may be preferably directed to the desired site (e.g. a tumor) by systemic administration to a subject.

In general, photoactivatable agents may be stimulated by light from insertion device(s) 3 of the invention, leading to subsequent irradiation, resonance energy transfer, exciton migration, electron injection, or chemical reaction, to an activated energy state that is capable of effecting the predetermined cellular change desired. In a one embodiment, the photoactivatable agent, upon activation, binds to DNA or RNA or other structures in a cell. The activated energy state of the agent is capable of causing damage to cells, inducing apoptosis. The mechanism of apoptosis is associated with an enhanced immune response that reduces the growth rate of cell proliferation disorders and may shrink solid tumors, depending on the state of the patient's immune system, concentration of the agent in the tumor, sensitivity of the agent to stimulation, and length of stimulation.

A preferred method of treating a cell proliferation disorder of the invention administers a photoactivatable agent to a patient, stimulates the photoactivatable agent by light from insertion device(s) 3 of the invention to induce cell damage, and generates an auto vaccine effect. In one further preferred embodiment, the photoactivatable agent is stimulated via resonance energy transfer (described below in more detail).

One advantage is that multiple wavelengths of emitted radiation from insertion device(s) 3 of the invention may be used to selectively stimulate one or more photoactivatable agents or energy modulation agents capable of stimulating the one or more photoactivatable agents. The energy modulation agent is preferably stimulated at a wavelength and energy that causes little or no damage to healthy cells, with the energy from one or more energy modulation agents being transferred, such as by Foerster Resonance Energy Transfer, to the photoactivatable agents that damage the cell and cause the onset of the desired cellular change, such as apoptosis of the cells.

Another advantage is that side effects can be greatly reduced by limiting the production of free radicals, singlet oxygen, hydroxides and other highly reactive groups that are known to damage healthy cells. Furthermore, additional additives, such as antioxidants, may be used to further reduce undesired effects of irradiation.

Various Light-Activated Pharmaceuticals Activatable with the Insertion Devices of the Invention Another object of the invention is to treat a condition, disorder or disease in a subject using an activatable pharmaceutical agent activated using the above-described light emitting insertion device(s) 3 of the invention.

It has been reported that ferritin could be internalized by some tumor tissues, and the internalization was associated with the membrane-specific receptors [S. Fargion, P. Arosio, A. L. Fracanzoni, V. Cislaghi, S. Levi, A. Cozzi, A Piperno and A. G. Firelli, *Blood*, 1988, 71, 753-757; P. C. Adams, L. W. Powell and J. W. Halliday, *Hepatology*, 1988, 8, 719-721]. Previous studies have shown that ferritin-binding sites and the endocytosis of ferritin have been identified in neoplastic cells [M. S. Bretscher and J. N. Thomson, *EMBO J.*, 1983, 2, 599-603]. Ferritin receptors have the potential for use in the delivery of anticancer drugs into the brain [S. W. Hulet, S. Powers and J. R. Connor, *J. Neurol. Sci.*, 1999, 165, 48-55]. In one embodiment, the invention uses ferritin or apoferritin to both encapsulate PA and energy modulation agent-PA systems and also target tumor cells selectively for enhanced drug delivery and subsequent phototherapy. In this case, no additional bioreactors are needed.

The photoactive drug molecules can be given to a patient by oral ingestion, skin application, or by intravenous injection. The photoactive drug molecules drugs travel through the blood stream inside the body towards the targeted tumor (either via passive or active targeting strategies). The invention treatment may also be used for inducing an auto vaccine effect for malignant cells, including those in solid tumors. To the extent that any rapidly dividing cells or stem cells may be damaged by a systemic treatment, then it may be preferable to direct the stimulating energy directly toward the tumor, preventing damage to most normal, healthy cells or stem cells by avoiding photoactivation or resonant energy transfer of the photoactivatable agent.

Alternatively, a treatment may be applied that slows or pauses mitosis. Such a treatment is capable of slowing the division of rapidly dividing healthy cells or stem cells during the treatment, without pausing mitosis of cancerous cells. Alternatively, a blocking agent is administered preferentially to malignant cells prior to administering the treatment that slows mitosis.

In one embodiment, an aggressive cell proliferation disorder has a much higher rate of mitosis, which leads to selective destruction of a disproportionate share of the malignant cells during even a systemically administered treatment. Stem cells and healthy cells may be spared from wholesale programmed cell death, even if exposed to photoactivated agents, provided that such photoactivated agents degenerate from the excited state to a lower energy state prior to binding, mitosis or other mechanisms for creating damage to the cells of a substantial fraction of the healthy stem cells. Thus, an auto-immune response may not be induced.

Alternatively, a blocking agent may be used that prevents or reduces damage to stem cells or healthy cells, selectively, which would otherwise be impaired. The blocking agent is selected or is administered such that the blocking agent does not impart a similar benefit to malignant cells, for example.

In one embodiment, stem cells are targeted, specifically, for destruction with the intention of replacing the stem cells with a donor cell line or previously stored, healthy cells of the patient. In this case, no blocking agent is used. Instead, a carrier or photosensitizer is used that specifically targets the stem cells.

Work in the area of photodynamic therapy has shown that the amount of singlet oxygen required to cause cell lysis, and thus cell death, is $0.32 \times 10^{-3}$ mol/liter or more, or $10^9$ singlet oxygen molecules/cell or more. However, in one embodiment of the invention, it is preferable to avoid production of an amount of singlet oxygen that would cause cell lysis, due to its indiscriminate nature of attack, lysing both target cells and healthy cells. Accordingly, in one embodiment of the invention it is preferred in the invention that the level of singlet oxygen production caused by the initiation energy used or activatable pharmaceutical agent upon activation be less than level needed to cause cell lysis.

In a further embodiment, methods in accordance with the invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV light is used as the activating energy, and antioxidants are added to reduce the unwanted side-effects of irradiation.

The activatable pharmaceutical agent and derivatives thereof as well as the energy modulation agents and plasmonics compounds and structures, can be incorporated into pharmaceutical compositions suitable for administration. Such compositions typically comprise the activatable pharmaceutical agent and a pharmaceutically acceptable carrier. The pharmaceutical composition also comprises at least one additive having a complementary therapeutic or diagnostic effect, wherein the additive is one selected from an antioxidant, an adjuvant, or a combination thereof.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such mediand agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the compound of the present invention to affect solubility or clearance of the compound. These molecules may also be synthesized with D-amino acids to increase resistance to enzymatic degradation. If necessary, the activatable pharmaceutical agent can be co-administered with a solubilizing agent, such as cyclodextran.

A pharmaceutical composition of the invention (including the drug or photoactivatable agent or energy modulation agent) is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteriand fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. These oral compositions can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, kit or dispenser together with instructions for administration.

Methods of administering agents are not limited to the conventional means such as injection or oral infusion, but include more advanced and complex forms of energy transfer. For example, genetically engineered cells that carry and express energy modulation agents may be used. Cells from the host may be transfected with genetically engineered vectors that express bioluminescent agents. Transfection may be accomplished via in situ gene therapy techniques such as injection of viral vectors or gene guns, or may be performed ex vivo by removing a sample of the host's cells and then returning to the host upon successful transfection. Such transfected cells may be inserted or otherwise targeted at the site where diseased cells are located.

It will also be understood that the order of administering the different agents is not particularly limited. It will be appreciated that different combinations of ordering may be advantageously employed depending on factors such as the absorption rate of the agents, the localization and molecular trafficking properties of the agents, and other pharmacokinetics or pharmacodynamics considerations.

An advantage of the methods of this approach is that by specifically targeting cells affected by a cell proliferation disorder, such as rapidly dividing cells, and triggering a cellular change, such as apoptosis, in these cells in situ, the immune system of the host may be stimulated to have an immune response against the diseased cells. Once the host's own immune system is stimulated to have such a response, other diseased cells that are not treated by the activatable pharmaceutical agent may be recognized and be destroyed by the host's own immune system. Such autovaccine effects may be obtained, for example, in treatments using psoralen and UV light, where the UV light comes from the light emitting insertion device(s) 3 of the invention.

The methods described here can be used alone or in combination with other therapies for treatment of cell proliferation disorders. Additionally, the methods described can be used, if desired, in conjunction with recent advances in chronomedicine, such as that detailed in Giacchetti et al, *Journal of Clinical Oncology*, Vol 24, No 22 (August 1), 2006: pp. 3562-3569, the entire contents of which are incorporated herein by reference.

In chronomedicine, it has been found that cells suffering from certain types of disorders, such as cancer, respond better at certain times of the day than at others. Thus, chronomedicine could be used in conjunction with the present methods in order to augment the effect of the treatments of the invention.

Photo-Treatment with the Insertion Devices of the Invention

Another object of the invention is to treat a condition, disorder or disease in a subject using an activatable pharmaceutical agent activated using the above-described light emitting insertion device(s) 3 of the invention. Exemplary conditions, disorders or diseases may include, but are not limited to, cancer, autoimmune diseases, cardiac ablasion (e.g., cardiac arrhythmiand atrial fibrillation), photoangioplastic conditions (e.g., de novo atherosclerosis, restinosis), intimal hyperplasia, arteriovenous fistula, macular degeneration, psoriasis, acne, hopeciareata, portwine spots, hair removal, rheumatoid and inflammatory arthrisis, joint conditions, lymph node conditions, and cognitive and behavioral conditions.

Accordingly, the invention in one embodiment provides methods utilizing the principle of energy transfer to and among molecular agents to control delivery and activation of pharmaceutically active agents such that delivery of the desired pharmacological effect is more focused, precise, and effective than the conventional techniques. Here, the energy transfer can include energy transfer from light from the light emitting insertion device(s) 3 of the invention.

Although not intending to be bound by any particular theory or be otherwise limited in any way, the following theoretical discussion of scientific principles and definitions are provided to help the reader gain an understanding and appreciation of the present invention.

As used here, the term "subject" is not intended to be limited to humans, but may also include animals, plants, or any suitable biological organism.

As used herein, the phrase "a disease or condition" refers to a condition, disorder or disease that may include, but are not limited to, cancer, soft and bone tissue injury, chronic pain, wound healing, nerve regeneration, viral and bacterial infections, fat deposits (liposuction), varicose veins, enlarged prostate, retinal injuries and other ocular diseases, Parkinson's disease, and behavioral, perceptional and cognitive disorders. Exemplary conditions also may include nerve (brain) imaging and stimulation, a direct control of brain cell activity with light, control of cell death (apoptosis), and alteration of cell growth and division. Yet other exemplary a condition, disorder or disease may include, but are not limited to, cardiac ablasion (e.g., cardiac arrhythmi- and atrial fibrillation), photoangioplastic conditions (e.g., de novo atherosclerosis, restinosis), intimal hyperplasia, arteriovenous fistula, macular degeneration, psoriasis, acne, hopeciareata, portwine spots, hair removal, rheumatoid and inflammatory arthritis, joint conditions, and lymph node conditions.

As used here, the term "target structure" refers to an eukaryotic cell, prokaryotic cell, a subcellular structure, such as a cell membrane, a nuclear membrane, cell nucleus, nucleic acid, mitochondria, ribosome, or other cellular organelle or component, an extracellular structure, virus or prion, and combinations thereof.

The nature of the predetermined cellular change will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, regulation of cytochrome c oxidase and flavoproteins, activation of mitochondria, stimulation antioxidant protective pathway, modulation of cell growth and division, alteration of firing pattern of nerves, alteration of redox properties, generation of reactive oxygen species, modulation of the activity, quantity, or number of intracellular components in a cell, modulation of the activity, quantity, or number of extracellular components produced by, excreted by, or associated with a cell, or a combination thereof. Predetermined cellular changes may or may not result in destruction or inactivation of the target structure.

Energy or light from the light emitting insertion device(s) 3 of the invention is provided at an energy at a level sufficient to cause cellular changes directly or via a modulation agent which is capable of causing the predetermined cellular changes. Also, the energy or light from the insertion device(s) 3 of the invention can be any energy source capable of providing energy at a level sufficient activate the activatable agent directly, or to provide the energy to a modulation agent with the input needed to emit the activation energy for the activatable agent (indirect activation).

An additional embodiment of the invention is to provide a method for treatment of a condition, disease or disorder by the in-situ generation of energy by way of the insertion device(s) 3 of the invention in a subject in need thereof, where the energy generated can be used directly to effect a change thereby treating the condition, disease or disorder, or the energy can be used to activate an activatable pharmaceutical agent, which upon activation effects a change thereby treating the condition, disease or disorder. The energy can be generated in-situ by any desired method, including, but not limited to, chemical reaction such as chemiluminescence, or by conversion of an energy applied to from the insertion device(s) 3, which can be converted in-situ to a different energy (of lower or higher energy than that applied), through the use of one or more energy modulation agents.

A further embodiment of the invention combines the treatment of a condition, disease or disorder with the generation of heat in the affected target structure in order to enhance the effect of the treatment. For example, in the treatment of a cell proliferation disorder using a photoactivatable pharmaceutical agent (such as a psoralen or derivative thereof), one can activate the photoactivatable pharmaceutical agent by applying light or other energy from the light emitting insertion device(s) 3 of the invention which, directly or indirectly, activate the pharmaceutical agent. As noted elsewhere in this application, this emitted energy from the insertion device(s) 3 of the invention can be of any type, so long as it is suitable for or can be converted to an energy suitable for activating the pharmaceutical compound. In addition to applying this energy from the insertion device(s) 3 of the invention, in this embodiment of the present invention, additional energy is applied that causes heating of the target structure. In the case of a cell proliferation disorder such as cancer, the heating would increase the proliferation rate of the cancer cells. While this may seem counterintuitive at first, when the cell proliferation disorder is being treated using a DNA intercalation agent, such as psoralen or a derivative thereof, this increase in cell proliferation can actually assist the psoralen in causing apoptosis. In particular, when psoralen becomes intercalated into DNA, apoptosis occurs when the cell goes through its next division cycle. By increasing the rate at which the cells divide, one can use the present invention methods to enhance the onset of apoptosis.

In one embodiment, heat can be generated by any desired manner. Preferably, the heat can be generated using the application of Radio Frequencies, microwaves, terahertz or NIR energy to the target structure or by the use of use of nanoparticles of metal or having metal shells. Heat can also be generated by the absorption of light from the light emitting insertion devices of the invention. Alternatively, as is done in tumor thermotherapy, magnetic metal nanoparticles can be targeted to cancer cells using conventional techniques, then used to generate heat by application of a magnetic field to the subject under controlled conditions. (DeNardo S J, DeNardo G L, Natarajan A et al.: Thermal dosimetry predictive of efficacy of 111In-ChL6 NPAMF-induced thermoablative therapy for human breast cancer in mice. J. Nucl. Med. 48(3), 437-444 (2007).)

In an additional embodiment, the photoactivatable agent can be a photocaged complex having an active agent contained within a photocage. The active agent is bulked up with other molecules that prevent it from binding to specific targets, thus masking its activity. When the photocage complex is photoactivated, the bulk falls off, exposing the active agent. In such a photocage complex, the photocage molecules can be photoactive (i.e. when photoactivated, they are caused to dissociate from the photocage complex, thus exposing the active agent within), or the active agent can be the photoactivatable agent (which when photoactivated causes the photocage to fall off), or both the photocage and the active agent are photoactivated, with the same or different wavelengths. For example, a toxic chemotherapeutic agent can be photocaged, which will reduce the systemic toxicity when delivered. Once the agent is concentrated in the tumor, the agent is irradiated with an activation energy. This causes the "cage" to fall off, leaving a cytotoxic agent in the tumor cell. Suitable photocages include those disclosed by Young and Deiters in "Photochemical Control of Biological Processes", *Org. Biomol. Chem.*, 5, pp. 999-1005 (2007) and "Photochemical Hammerhead Ribozyme Activation", *Bioorganic & Medicinal Chemistry Letters*, 16(10), pp. 2658-2661 (2006), the contents of which are hereby incorporated by reference. In one embodiment, the use of light (e.g. or other energy) from the light emitting insertion device(s) 3 of the invention for uncaging a compound or agent.

In one embodiment, the use of light (e.g. or other energy) from the light emitting insertion device(s) 3 of the invention for uncaging a compound or agent is used for elucidation of neuron functions and imaging, for example, two-photon glutamine uncaging (Harvey C D, et al., Nature, 450:1195-1202 (2007); Eder M, et al., Rev. Neurosci., 15:167-183 (2004)). Other signaling molecules can be released by UV light stimulation, e.g., GABA, secondary messengers (e.g., $Ca^{2+}$ and $Mg^{2+}$), carbachol, capsaicin, and ATP (Zhang F., et al., 2006). Chemical modifications of ion channels and receptors may be carried out to render them light-responsive. $Ca^{2+}$ is involved in controlling fertilization, differentiation, proliferation, apoptosis, synaptic plasticity, memory, and developing axons. In yet another preferred embodiment, $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

Genetic targeting allows morphologically and electrophysipologically characterization of genetically defined cell populations. Accordingly, in an additional embodiment, a light-sensitive protein is introduced into cells or live subjects via number of techniques including electroporation, DNA microinjection, viral delivery, liposomal transfection, creation of transgenic lines and calcium-phosphate precipitation. For example, lentiviral technology provides a convenient combination a conventional combination of stable long-term expression, ease of high-titer vector production and low immunogenicity. The light-sensitive protein may be, for example, channelrhodopsin-2 (ChR2) and chloride pump halorhodopsin (NpHR). The light protein encoding gene(s) along with a cell-specific promoter can be incorporated into the lentiviral vector or other vector providing delivery of the light-sensitive protein encoding gene into a target cell. ChR2 containing a light sensor and a cation channel, provides electrical stimulation of appropriate speed and magnitude to activate neuronal spike firing, when the cells harboring Ch2R are pulsed with light.

In one embodiment, a lanthanide chelate capable of intense luminescence can be used. For example, a lanthanide chelator may be covalently joined to a coumarin or coumarin derivative or a quinolone or quinolone-derivative sensitizer. Sensitizers may be a 2- or 4-quinolone, a 2- or 4-coumarin, or derivatives or combinations of these examples. A carbostyril 124 (7-amino-4-methyl-2-quinolone), a coumarin 120 (7-amino-4-methyl-2-coumarin), a coumarin 124 (7-amino-4-(trifluoromethyl)-2-coumarin), aminoinethyltrimethylpsoralen or other similar sensitizer may be used. Chelates may be selected to form high affinity complexes with lanthanides, such as terbium or europium, through chelator groups, such as DTPA. Such chelates may be coupled to any of a wide variety of well known probes or carriers, and may be used for resonance energy transfer to a psoralen or psoralen-derivative, such as 8-MOP, or other photoactive molecules capable of binding DNA. In one alternative example, the lanthanide chelate is localized at the site of the disease using an appropriate carrier molecule, particle or polymer, and a source of electromagnetic energy is introduced by minimally invasive procedures (e.g., the gas containing upconverters of the invention) to irradiate the target structure, after exposure to the lanthanide chelate and a photoactive molecule.

In another embodiment, a biocompatible, endogenous fluorophore emitter can be selected to stimulate resonance energy transfer to a photoactivatable molecule. A biocompatible emitter (e.g. light from the light emitting insertion device(s) 3 of the invention) with an emission maxima within the absorption range of the biocompatible, endogenous fluorophore emitter may be selected to stimulate an excited state in fluorophore emitter. One or more halogen atoms may be added to any cyclic ring structure capable of intercalation between the stacked nucleotide bases in a nucleic acid (either DNA or RNA) to confer new photoactive properties to the intercalator. Any intercalating molecule (psoralens, coumarins, or other polycyclic ring structures) may be selectively modified by halogenation or addition of non-hydrogen bonding ionic substituents to impart advantages in its reaction photochemistry and its competitive binding affinity for nucleic acids over cell membranes or charged proteins, as is known in the art.

Skin photosensitivity is a major toxicity of photosensitizers. Severe sunburn occurs if skin is exposed to direct sunlight for even a few minutes. Early murine research hinted at a vigorous and long term stimulation of immune response; however, actual clinical testing has failed to achieve the early promises of photodynamic therapies. The early photosensitizers for photodynamic therapies targeted type II responses, which created singlet oxygen when photoactivated in the presence of oxygen. The singlet oxygen caused cellular necrosis and was associated with inflammation and an immune response. Some additional photosensitizers have been developed to induce type I responses, directly damaging cellular structures.

Porfimer sodium (Photofrin; QLT Therapeutics, Vancouver, BC, Canada), is a partially purified preparation of hematoporphyrin derivative (HpD). Photofrin has been approved by the US Food and Drug Administration for the treatment of obstructing esophageal cancer, microinvasive endobronchial non-small cell lung cancer, and obstructing endobronchial non-small cell lung cancer. Photofrin is activated with 630 nm, which has a tissue penetration of approximately 2 to 5 mm. Photofrin has a relatively long duration of skin photosensitivity (approximately 4 to 6 weeks).

Tetra (m-hydroxyphenyl) chlorin (Foscan; Scotia Pharmaceuticals, Stirling, UK), is a synthetic chlorine compound that is activated by 652 nm light. Clinical studies have demonstrated a tissue effect of up to 10 mm with Foscan and 652 nm light. Foscan is more selectively a photosensitizer in tumors than normal tissues, and requires a comparatively short light activation time. A recommended dose of 0.1 mg/kg is comparatively low and comparatively low doses of light may be used. Nevertheless, duration of skin photosensitivity is reasonable (approximately 2 weeks). However, Foscan induces a comparatively high yield of singlet oxygen, which may be the primary mechanism of DNA damage for this molecule.

Motexafin lutetium (Lutetium texaphryin) is activated by light in the near infrared region (732 nm). Absorption at this wavelength has the advantage of potentially deeper penetration into tissues, compared with the amount of light used to activate other photosensitizers. Lutetium texaphyrin also has one of the greatest reported selectivities for tumors compared to selectivities of normal tissues. Young S W, et al.: Lutetium texaphyrin (PCI-0123) a near-infrared, water-soluble photosensitizer. Photochem Photobiol 1996, 63:892-897. In addition, its clinical use is associated with a shorter duration of skin photosensitivity (24 to 48 hours). Lutetium texaphryin has been evaluated for metastatic skin cancers. It is currently under investigation for treatment of recurrent breast cancer and for locally recurrent prostate cancer. The high selectivity for tumors promises improved results in clinical trials.

In general, the approach may be used with any source for the excitation an activatable molecule. The process may be a photopheresis process or may be similar to photophoresis. While photophoresis is generally thought to be limited to photonic excitation, such as by UV-light, other forms of radiation may be used as a part of a system to activate an activatable molecule. Light emission from the insertion device(s) 3 can stimulate the activation of an activatable molecule, such as 8-MOP. In one example, light or other energy emission from the insertion device(s) 3 of the invention is directed at a solid tumor and stimulates, directly or indirectly, activation of 8-MOP.

In yet another embodiment, the activatable pharmaceutical agent, preferably a photoactive agent, is directed to a receptor site by a carrier having a strong affinity for the receptor site. The carrier may be a polypeptide and may form a covalent bond with a photo active agent, for example. The polypeptide may be an insulin, interleukin, thymopoietin or transferrin, for example. Alternatively, a photoactive pharmaceutical agent may have a strong affinity for the target cell without a binding to a carrier.

For example, a treatment may be applied that acts to slow or pause mitosis. Such a treatment is capable of slowing the division of rapidly dividing healthy cells or stem cells without pausing mitosis of cancerous cells. Thus, the difference in growth rate between the non-target cells and target cells are further differentiated to enhance the effectiveness of the methods of the invention.

In a further embodiment, methods in accordance with the invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

In another aspect, the invention also provides methods for producing an autovaccine, including: (1) providing a population of targeted cells; (2) treating the cells ex vivo with a psoralen or a derivative thereof; (3) activating the psoralen ex-vivo or in vivo to induce a predetermined change in a target structure in the population of the target cells by inducing an autovaccine effect against the targeted cell, wherein the treated cells cause an autovaccine effect.

Photobiomodulation

Photobiomodulation also known as low level laser therapy (LLLT), cold laser therapy, and laser biostimulation, is an emerging medical and veterinary technique in which exposure to low-level laser light can stimulate or inhibit cellular function leading to beneficial clinical effects. The "best" combination of wavelength, intensity, duration, and treatment interval is complex and sometimes controversial with different diseases, injuries and dysfunctions needing different treatment parameters and techniques.

In one embodiment of this invention, the light emitting insertion device(s) 3 of the invention provide the light for producing photobiomodulation. Certain wavelengths of light emitted from the light emitting insertion devices of the invention at certain intensities will, for example, aid tissue regeneration, resolve inflammation, relieve pain and boost the immune system. Observed biological and physiological effects to be expected include changes in cell membrane permeability, and up-regulation and down-regulation of adenosine triphosphate and nitric oxide.

All light-induced biological effects depend on the parameters of the irradiation (wavelength, dose, intensity, irradiation time, depth of a target cell, and continuous wave or pulsed mode, pulse parameters). (See, e.g., Karu I T, Low-Power Laser Therapy", in Biomedical Photonics Handbook, Vo-Dinh T. Ed., CRC Press, Boca Raton, Fla., pp. 48-1 to 48-25, (2003)). The light emitting insertion device(s) 3 of the invention can be programmed or instructed to deliver light comparable to that of known photobiomodulation treatments. For example, the light emitting insertion device(s) 3 of the invention can be programmed or instructed to deliver light with an average power typically in the range of 1-500 mW; or with peak power and short pulse width in the range of 1-100 W with 200 ns pulse widths. In this example, the average beam irradiance would typically be 10 mW/cm$^2$-5 W/cm$^2$. The light emitting insertion device(s) 3 of the invention can be programmed or instructed to or configured to deliver light at a wavelength typically in the range 600-1000 nm. For example, down converting phosphors could be coated on the light emitting surface of the insertion devices to convert UV or visible light to these or other appropriate wavelengths. For example, the light emission source in the insertion devices could itself directly produce these or other appropriate wavelengths. The red-to-near infrared (NIR) region is preferred for photobiomodulation. Other wavelengths may be also used, e.g., UV light for neurons and green light for prostate tissue. Maximum biological responses have been seen to occur from prior work when the tissues were irradiated at 620, 680, 760, and 820-830 nm (Karu T I, et al., (1998).

The phenomenon of ultra weak emission from cellular systems has been a topic of various inquiries since the 1900s. This topic can be traced back to the early investigations of the Russian biologist Gurwitsch Alexander G. Gurwitsch more than seventy years ago, who speculated that ultraweak photon emission transmit information in cells [A. G. Gurwitsch, S. S. Grabje, and S. Salkind, "Die Natur des spezifischen Erregers der Zellteilung," Arch. Entwicklungsmech. Org. 100, 11-40, 1923].

UV excitation is known to enhance the ultra-weak emission and a method for detecting UV-A-laser-induced ultraweak photon emission was used to evaluate differences between cancer and normal cells. [H. J. Niggli et al, Laser-ultraviolet-A-induced ultraweak photon emission in mammalian cells, *Journal of Biomedical Optics* 10(2), 024006 (2005)].

Accordingly, in one embodiment of the present invention, upon applying light or energy from the insertion device(s) 3 of the invention to a target structure in a subject in need of treatment, the initiation energy contacts the target structure and induces a predetermined change in said target structure in situ, wherein the predetermined change is the enhancement of energy emission from the target, which then mediates, initiates or enhances a biological activity of other target structures in the subject, or of a second type of target structure (e.g., a different cell type).

While not bound to the particular following theory, a photoacceptor first absorbs the light used for the irradiation. After promotion of electronically excited states, primary molecule processes from these states can lead to a measurable biological effect (via secondary biochemical reaction, or photosignal transduction cascade, or cellular signaling) at the cellular level. A photoacceptor for eukaryotic cells in red-to-NIR region is believed to be the terminal enzyme of the respiratory chain cytochrome c oxidase located in cell mitochondrion. In the violet-to blue spectra region, flavoprotein (e.g., NADHdehydrogenase in the beginning of the respiratory chain) is also among the photoacceptors. The light emitting insertion devices of the invention can be programmed or instructed to or configured to deliver light at these wavelengths.

Clinical applications of photobiomodulation include, for example, treating soft tissue and bone injuries, chronic pain, wound healing and nerve and sensory regeneration/restoration, and possibly even resolving viral and bacterial infections, treating neurological and phychiatric diseases (e.g., epilepsy and Parkinson's disease) (e.g., Zhang F., et al., Nature, 446:617-9 (Apr. 5, 2007; Han X., et al., PloS ONE, 2(3):e299 (Mar. 21, 2007); Arany P R, et al., Wound Repair Regen., 15(6):866-74 (2007); Lopes C B, et al., Photomed. Laser Surg., 25(2):96-101 (2007)). One clinical application showing great promise is the treatment of inflammation, where the anti-inflammatory effect of location-and-dose-specific laser irradiation produces similar outcomes as NSAIDs, but without the potentially harmful side-effects (Bjordal J M, Couppé C, Chow R T, Tuner J, Ljunggren E A (2003). "A systematic review of low level laser therapy with location-specific doses for pain from chronic joint disorders". The Australian journal of physiotherapy 49(2): 107-16). The light emitting insertion devices of the invention can be programmed or instructed to or configured to deliver light at the wavelengths and illuminations reported in this work.

An NIR light treatment can prevent cell death (apoptosis) in cultured neurons (brain) cells (Wong-Reiley M T, et al., JBC, 280(6):4761-71 (2005)). Specific wavelengths of light can promote cellular proliferation to the activation of mitochondria, the energy-producing organelles within the cell via cytochrome c oxidase. An NIR treatment can augment mitochondrial function and stimulate antioxidant protective pathways. The evidence that the NIR treatment can augment mitochondrial function and stimulate antioxidant protective pathways comes from photobiomodulation experiments carried out using a laboratory model of Parkinson's disease (PD) (cultures of human dopaminergic neuronal cells) (Whelan H., et. al., SPIE, Newsroom, pages 1-3 (2008)). The light emitting insertion device(s) 3 of the invention can be constructed and programmed or instructed to and/or configured to deliver light at these NIR wavelengths.

It has also been shown that light has both inductive and inhibitory effect on cell growth and division in a red tide flagellate, Chattonellantique (Nemote Y., Plant and Cell Physiol., 26(4):669-674 (1985)). The light emitting insertion device(s) 3 of the invention can be constructed and programmed or instructed to or configured to deliver light at these wavelengths.

When the excitable cells (e.g., neurons, cardiomyocites) are irradiated with monochromatic visible light, the photoacceptors are also believed to be components of respiratory chain. It is clear from experimental data (Karu, T. I., (2002). Low-power laser therapy. In: CRC Biomedical Photonics Handbook, T. Vo-Dinh, Editor-in-Chief, CRC Press, Boca Raton (USA)) that irradiation can cause physiological and morphological changes in nonpigmental excitable cells viabsorption in mitochondria. Later, similar irradiation experiments were performed with neurons in connection with low-power laser therapy. It was shown in 80's that He—Ne laser radiation alters the firing pattern of nerves; it was also found that transcutaneous irradiation with HeNe laser mimicked the effect of peripheral stimulation of a behavioral reflex. These findings were found to be connected with pain therapy (Karu T I, et al., (2002)). The light emitting insertion device(s) 3 of the invention can be programmed or instructed to or configured to deliver light at these wavelengths.

When photoacceptors absorb photons, electronic excitation followed by photochemical reactions occurring from lower excitation states (first singlet and triplet) takes place. It is also known that electronic excitation of absorbing centers alters their redox properties. Five primary reactions have been discussed in literature (Karu T I, et al., (2002)). Two of them are connected with alteration of redox properties and two mechanisms involve generation of reactive oxygen species (ROE). Also, induction of local transient (very short time) heating of absorbing chromophores is possible. Details of these mechanisms can be found in (Karu T I, et. al., (2002); Karu T I, et al., (1998). The Science of Low Power Laser Therapy. Gordon and Breach Sci. Publ., London). The insertion device(s) 3 of the invention can be constructed and programmed or instructed to or configured to deliver light at these wavelengths.

Photobiological action via activation of respiratory chain is believed to be a general mechanism occurring in cells. Crucial events of this type of cell metabolism activation are occurring due to a shift of cellular redox potential into more oxidized direction as well as due to ATP extrasynthesis. Susceptibility to irradiation and capability for activation depend on physiological status of irradiated cells: the cells, which overall redox potential is shifted to more reduced state (example: some pathological conditions) are more sensitive to the irradiation. The specificity of final photobiological response is determined not at the level of primary reactions in the respiratory chain but at the transcription level during cellular signaling cascades. In some cells, only partial activation of cell metabolism happens by this mechanism (example: redox priming of lymphocytes). The insertion device(s) 3 of the invention can be constructed and programmed or instructed to or configured to deliver light at these wavelengths.

Far red and NIR radiation have been shown to promote wound healing, e.g., infected, ischemic, and hypoxic wounds (Wong-Reley, WTT, JBC, 280(6):4761-4771 (2005)). Red-to-NIR radiation also protects the retina against the toxic actions of methanol-derived formic acid in a rodent model of methanol toxicity and may enhance recovery from retinal injury and other ocular diseases in which mitochondrial dysfunction is postulated to play a role (Eells J T., PNAS, 100(6):3439-44 (2003)). Another clinical application of photobiomodulation is repair of soft and bone tissues by IR laser irradiation (Martinez M E, et al., Laser in Med. Sci., 2007). Invasive laser assisted liposuction is a recently developed method, wherein a laser fiber is introduced through a tube into the skin and directly to the fat cells causing the cells to rapture and drain away as liquid (Kim K H, Dermatol. Surg., 32(2):241-48 (2006)). Tissue around the area is coagulated. Yet, another application of photobiomodulation is a non-surgical varicose vein treatment (an endovenous laser therapy), wherein a laser is threaded through an incision and the full length of the varicose vein (Kim H S, J. Vasc. Interv. Radiol., 18(6):811 (2007)). When the laser is slowly withdrawn, heat is applied to the vein walls, causing the vein to permanently close and disappear. The insertion device(s) 3 of the invention can be constructed and programmed or instructed to or configured to deliver light at these wavelengths.

The green light laser is a laser that vaporizes and removes the enlarged prostate tissue (Heinrich E., Eur. Urol., 52(6): 1632-7 (2007)). The significance of the color of the laser light (green) is that this results in absorption by hemoglobin which is contained within red blood cells and not absorbed by water. The procedure may also be known as laser prostatectomy or laser Transurethral resection of the prostate (TURP). The technique involves painting the enlarged prostate with the laser until the capsule of the prostate is reached. By relieving this portion of the prostate, patients are able to void much easier through a wide-open channel in the prostate. The procedure needs to be performed under general or spinal anesthesia. An advantage of the procedure is that even patients taking blood thinners (e.g., aspirin to prevent stroke) can be treated because there is less bleeding compared to a traditional surgery. The insertion device(s) 3 of the invention can be constructed and programmed or instructed to or configured to deliver light at these wavelengths.

Yet, another area of application of photobiomodulation is a direct control of brain cell activity with light. The technique is based upon NIR spectroscopy and is simpler to use and less expensive than other methods such as functional magnetic resonance imaging and positron emission tomography.

Whenever a region of the brain is activated, that part of the brain uses more oxygen. This technique works by measuring the blood flow and oxygen consumption in the brain. The light emitted by NIR laser diodes is carried through optical fibers to a person's head. The light penetrates the skull where it assesses the brain's oxygen level and blood volume. The scattered light is then collected by optical fibers, sent to detectors and analyzed by a computer. By examining how much of the light is scattered and how much is absorbed, portions of the brain and extract information about brain activity can be mapped. By measuring the scattering, it is determined where the neurons are firing. This means that scientists can simultaneously detect both blood profusion and neural activity. The technique could be used in many diagnostic, prognostic and clinical applications. For example, it could be used to find hematomas in children, to study blood flow in the brain during sleep apnea, and to monitor recovering stroke patients on a daily, or even hourly, basis (that would be impractical to do with MRI). To validate the technique, hemoglobin oxygen concentrations in the brain obtained simultaneously by NIR spectroscopy and by functional MRI, the current "gold standard" in brain studies, was compared. Both methods were used to generate functional maps of the brain's motor cortex during a periodic sequence of stimulation by finger motion and rest. Spatial congruence between the hemoglobin signal and the MRI signal in the motor cortex related to finger movement was demonstrated. The researchers also demonstrated collocation between hemoglobin oxygen levels and changes in scattering due to brain activities. The changes in scattering associated with fast neuron signals came from exactly the same locations. The insertion device(s) 3 of the invention can be constructed and programmed or instructed to or configured to deliver light at these wavelengths.

A low-intensity laser light-oxygen cancer therapy is another application of photobiomodulation. The light-oxygen effect (LOE), which involves activation of or damage to biosystems by optical radiation at low optical doses by direct photoexcitation of molecular oxygen dissolved in a biosystem so that it is converted to the singlet state, i.e., by photogeneration of molecular singlet oxygen from $O_2$ dissolved in cells, similar to photodynamic effect (Zakharov S D, et al., Quantum Electronics, 29(12):1031-53 (1999)). It was shown that the He—Ne laser radiation destroys tumor cells in the presence or absence of the photosensitiser. The LOE can be activated by small optical doses, which are 4-5 orders of magnitude lower that those found if a comparison is made with the familiar analogue in the form of the photodynamic effect (PDE). The insertion device(s) 3 of the invention can be constructed and programmed or instructed to or configured to deliver light at these wavelengths.

Another type of photobiomodulation methods fall into two general categories: one set of methods uses light to uncage a compound that then becomes biochemically active, binding to a downstream effector; the other set uses light to activate a light-sensitive protein such as rhodopsin (ChR2), which can then excite the cell expressing the opsin. The insertion device(s) 3 of the invention can be constructed and or instructed to or configured to deliver light for these types of photobiomodulation.

In the first set, this method involves applying "caged" chemicals to a sample and then using light to open the cage to invoke a reaction. Modified glutamate is useful for finding excitatory connections between neurons, since the uncaged glutamate mimics the natural synaptic activity of one neuron impinging upon another. This method is used for elucidation of neuron functions and imaging in brain slices using, for example, two-photon glutamine uncageing (Harvey C D, et al., Nature, 450:1195-1202 (2007); Eder M, et al., Rev. Neurosci., 15:167-183 (2004)). Other signaling molecules can be released by UV light stimulation, e.g., GABA, secondary messengers (e.g., $Ca^{2+}$ and $Mg^{2+}$), carbachol, capsaicin, and ATP (Zhang F., et al., 2006). Chemical modifications of ion channels and receptors may be carried out to render them light-responsive. $Ca^{2+}$ is involved in controlling fertilization, differentiation, proliferation, apoptosis, synaptic plasticity, memory, and developing axons. In yet another preferred embodiment, $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

In the second set which uses light to activate a light-sensitive protein such as rhodopsin (ChR2), which can then excite the cell expressing the opsin, It has been shown that channelrhodopsin-2, a monolithic protein containing a light sensor and a cation channel, provides electrical stimulation of appropriate speed and magnitude to activate neuronal spike firing. Recently, photoinhibition, the inhibition of neural activity with light, has become feasible with the application of molecules such as the light-activated chloride pump halorhodopsin to neural control. Together, blue-light activated channelrhodopsin-2 and the yellow light-activated chloride pump halorhodopsin enable multiple-color, optical activation and silencing of neural activity.

ChR2 photostimulation involves genetic targeting ChR2 to neurons and light pulsing the neurons expressing ChR2 protein. The experiments have been conducted in vitro and in vivo in mice by in vivo deep-brain photostimulaiton using optical fibers to deliver light into the lateral hypothalamus (Adamantidis A R, et al., Nature 450:420-425 (2007)). Genetic targeting of ChR2 allows exclusive stimulation of defined cellular subsets and avoids the need for addition of the caged glutamate, facilitating photostimulation in vivo (Wang H., et al., PNAS, 104(19):8143-48 (2007)). ChR2 photostimulation has been used for restoring visual activity in mice with impaired vision, to evoke behavioral responses in worms and flies (Wang H., et al., 2007). The robust associative learning induced by ChR2-assisted photostimulaiton in mice opens the door to study the circuit basis of perception and cognition in vivo (Huber D., et al., 2007). This kind of neuronal targeting and stimulation might have clinical application, e.g., deep brain stimulation to treat Parkinson's disease and other disorders, controlling behavioral, perceptional and cognitive characteristics, and for imaging and studying how the brain works (Zhang F., et al., Nature Methods, 3(10):785-792 (2006); Wong-Riley M T., et al., JBC, 280(6):4761-4771 (2005)).

Another gene, chloride pump (NpHR), which is borrowed from a microbe called an archaebacterium, can make neurons less active in the presence of yellow light. Combined, the two genes ChR2 and NpHR can now make neurons obey pulses of light like drivers obey a traffic signal: Blue means "go" (emit a signal), and yellow means "stop" (don't emit).

Light-sensitive proteins can be introduced into cells or live subjects via number of techniques including electroporation, DNA microinjection, viral delivery, liposomal transfection and calcium-phosphate precipitation.

Photostimulation

A photostimulation technique involves chemical modification of ion channels and receptors to render them light-responsive. The insertion device(s) 3 of the invention can be constructed and or instructed to or configured to deliver light for this technique. Some of the most fundamental signaling mechanisms in a cell involve the release and uptake of $Ca^{2+}$ ions. $Ca^{2+}$ is involved in controlling fertilization, differentiation, proliferation, apoptosis, synaptic plasticity, memory, and developing axons. It has been shown that $Ca^{2+}$ waves can be induced by UV irradiation (single-photon absorption) and NIR irradiation (two-photon absorption) by releasing caged $Ca^{2+}$, an extracellular purinergic messenger InsP3 (Braet K., et al., Cell Calcium, 33:37-48 (2003)), or ion channel ligands (Zhang F., et al., 2006).

Directly controlling a brain cell activity with light is a novel means for experimenting with neural circuits and could lead to therapies for some disorders. This accomplishment is a step toward the goal of mapping neural circuit dynamics on a millisecond timescale to see if impairments in these dynamics underlie severe psychiatric symptoms. Knowing the effects that different neurons have could ultimately help researchers figure out the workings of healthy and unhealthy brain circuits. If use of the technique can show that altered activity in a particular kind of neuron underlies symptoms, for example, this insight will allow development of targeted genetic or pharmaceutical treatments to fix those neurons. Conceivably, direct control of neuronal activity with light could someday become a therapy in itself. Here, the insertion device(s) 3 of the invention can be constructed and or instructed to or configured to deliver light for direct control of neuronal activity.

In living organisms, scientists have been able to cause worms, C. elegans, to stop swimming while their genetically altered motor neurons were exposed to pulses of yellow light intensified through a microscope. In some experiments, exposure to blue light caused the worms to wiggle in ways they weren't moving while unperturbed. When the lights were turned off, the worms resumed their normal behavior.

Meanwhile, in experiments in living brain tissues extracted from mice, the researchers were able to use the technique to cause neurons to signal or stop on the millisecond timescale, just as they do naturally. Other experiments showed that cells appear to suffer no ill effects from exposure to the light. The mice resume their normal function once the exposure ends.

The most direct application of an optical neuron control is experimenting with neural circuits to determine why unhealthy ones fail and how healthy ones work.

In patients with Parkinson's disease, for example, researchers have shown that electrical "deep brain stimulation" of cells can help patients. By allowing researchers to selectively stimulate or dampen different neurons in the brain, the light stimulation techniques could help in determining which particular neurons are benefiting from deep brain stimulation. That could lead to making the electrical treatment, which has some unwanted side effects, more targeted.

Another potential application is experimenting with simulating neural communications. Because neurons communicate by generating patterns of signals-sometimes on and sometimes off like the 0s and 1s of binary computer code-flashing blue and yellow lights in these patterns could compel neurons to emit messages that correspond to real neural instructions. In the future, this could allow researchers to test and tune sophisticated neuron behaviors. Much farther down the road, the ability to artificially stimulate neural signals, such as movement instructions, could allow doctors to bridge blockages in damaged spinal columns, perhaps restoring some function to the limbs of paralyzed patients.

Finally, the technique could be useful in teasing out the largely unknown functioning of healthy brains. Here, the insertion device(s) 3 of the invention can be constructed and or instructed to or configured to deliver light for control of these and other neuron activities.

Drug Packaging

The reagents and chemicals useful for methods and systems of the present invention may be packaged in kits to facilitate application of the present invention. In one exemplary embodiment, a kit including a psoralen, and fractionating containers for easy fractionation and isolation of autovaccines is contemplated. A further embodiment of kit would comprise at least one activatable pharmaceutical agent capable of causing a predetermined cellular change, at least one energy modulation agent capable of activating the at least one activatable agent when energized, and containers suitable for storing the agents in stable form, and preferably further comprising instructions for administering the at least one activatable pharmaceutical agent and at least one energy modulation agent to a subject, and for applying an initiation energy from an initiation energy source to activate the insertion device(s) which in turn activate the pharmaceutical agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation of initiation source.

Sterilization and Cold Pasteurization of Fluids

It is known that ultraviolet (UV) with a wavelength of 254 nm tends to inactivate most types of microorganisms. Most juices are opaque to UV due to the high-suspended solids in them and hence the conventional UV treatment, usually used for water treatment, cannot be used for treating juices. In order to make the process efficient, a thin film reactor constructed from glass has been used with the juice flowing along the inner surface of a vertical glass tube as a thin film. See "Ultraviolet Treatment of Orange Juice" by Tran et al. published in Innovative Food Science & Emerging Technologies (Volume 5, Issue 4, December 2004, Pages 495-502), the entire contents of which are incorporated herein by reference. Tran et al. reported that decimal reduction doses required for the reconstitute orange juices (OJ; 10.5° Brix) were 87±7 and 119±17 mJ/cm$^2$ for the standard aerobic plate count (APC) and yeast and moulds, respectively. They also reported that the shelf life of fresh squeezed orange juice was extended to 5 days with a limited exposure of UV (73.8 mJ/cm$^2$). The effect of UV on the concentration of Vitamin C was investigated using both HPLC and titration methods of measurements. The degradation of Vitamin C was 17% under high UV exposure of 100 mJ/cm$^2$, which was similar to that usually found in the final sterilization. Enzyme pectin methylesterase (PME) activity, which is the major cause of cloud loss of juices, was also measured. The energy required for UV treatment of orange juice (2.0 kW h/m$^3$) was much smaller than that required in thermal treatment (82 kW h/m$^3$). The color and pH of the juice were not significantly influenced by the treatment.

The invention described herein offers advantages over this approach in that the insertion device(s) 3 of the invention can be placed inside fixtures such as quartz or glass (encapsulation structures) within the orange juice (or other fluid medium) and irradiated with microwave or RF power supplied to activate insertion device(s) 3 in the orange juice.

While discussed with regard to orange juice, any other medium to be sterilized including food products, medical products and cosmetic products could be treated using the technique of the invention described herein.

Sterilization of Blood Products

U.S. Pat. No. 6,087,141 (the entire contents of which are incorporated herein by reference) describes an ultraviolet light activated psoralen process for sterilization of blood transfusion products. The invention can be applied for the neutralization of AIDS and HIV or other viral or pathogenic agents in blood transfusion products. In this embodiment, at least one photoactivatable agent is selected from psoralens, pyrene cholesteiyloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, anthroquinones, porphycene, rubyrin, rosarin, hexaphyrin, sapphyrin, chlorophyl, chlorin, phthalocynine, porphyrazine, bacteriochlorophyl, pheophytin, texaphyrin macrocyclic-based component, or a metalated derivative thereof. These photoactivatable agents serve as recipients for the generated light from the insertion device(s) 3.

The recipient in this and other embodiments of the invention can include at least one of a laser dye, a fluorophore, a lumophore, or a phosphor. The laser dye can be at least one of p-terphenyl, sulforhodamine B, p-quaterphenyl, Rhodamine 101, curbostyryl 124, cresyl violet perchlorate, popop, DODC iodide, coumarin 120, sulforhodamine 101, coumarin 2, oxozine 4 perchlorate, coumarin 339, PCM, coumarin 1, oxazine 170 perchlorate, coumarin 138, nile blue A perchlorate, coumarin 106, oxatine 1 perchlorate, coumarin 102, pyridine 1, coumarin 314T, styryl 7, coumarin 338, HIDC iodide, coumarin 151, PTPC iodide, coumarin 4, cryptocyanine, coumarin 314, DOTC iodide, coumarin 30, HITC iodide, coumarin 500, HITC perchlorate, coumarin 307, PTTC iodide, coumarin 334, DTTC perchlorate, coumarin 7, IR-144, coumarin 343, HDITC perchlorate, coumarin 337, IR-NO, coumarin 6, IR-132, coumarin 152, IR-125, coumarin 153, boron-dipyrromethere, HPTS, flourescein, rhodamine 110, 2, 7-dichlorofluorescein, rhodamine 65, and rhodamin 19 perchlorate, rhodamine b, and derivatives of these laser dyes that are modified by addition the addition of appropriate substituents to modify solubility or tune their interactions within the biological milieu.

In various embodiments of the invention, the recipients are secondary agents performing other functions. Suitable secondary agents for the invention include secondary emitters, cytotoxic agents, magnetic resonance imaging (MRI) agents, positron emission tomography (PET) agents, radiological imaging agents, or photodynamic therapy (PDT) agents.

These photoactivatable agents (recipients and secondary agents) are introduced into the blood product (or a patient's blood stream). Microwave or RF power is applied to the blood product (or to the patient). The insertion device(s) 3 (either included in the blood product) or in encapsulated structures generate secondary light such as UV light which activates the photoactivatable agents in the blood products.

In a specific example, the photoactivatable agent is a psoralen, a coumarin, or a derivative thereof, and as discussed above, one can sterilize blood products in vivo (i.e., in a patient) or in a container of the blood product (such as for example donated blood). The treatment can be applied to treat disorders such as for example a cancer cell, a tumor cell, an autoimmune deficiency symptom virus, or a blood-borne germicide is treated by the psoralen, the coumarin, or the derivative thereof.

Waste Water Detoxification

Photocatalysis has also been used as tertiary treatment for wastewater to comply with regulatory discharge limits and to oxidize compounds that have not been oxidized in the biological treatment. Photocatalysis has been used to reduce or eliminate several pollutants (e.g., alkanes, alkenes, phenols, aromatics, pesticides) with great success. In many cases, total mineralization of the organic compounds has been observed. Several photocatalysts, such as CdS, $Fe_2O_3$, ZnO, WO$_3$, and ZnS, have been studied, but the best results have been achieved with TiO$_2$ P$_{25}$. These photocatalyst can be used in the invention.

The wastewaters of an oil refinery are the waters resulting from washing the equipment used in the process, undesirable wastes, and sanitary sewage. These effluents have high oil and grease contents, besides other organic compounds in solution. These pollutants form a residual chemical oxygen demand (COD) that may pose serious toxic hazards to the environment.

It is known that photocatalysis can be used for waste water reduction remediation. U.S. Pat. No. 5,118,422 (the entire contents of which are incorporated herein by reference) to Cooper et al. describe an ultraviolet driven photocatalytic post-treatment technique for purifying a water feedstock containing an oxidizable contaminant compound. In this work, the water feedstock was mixed with photocatalytic semiconductor particles (e.g., TiO$_2$, ZnO, CdS, CdSe, SnO$_2$, SrTiO$_3$, WO$_3$, Fe$_2$O$_3$, and Ta$_2$O$_5$ particles) having a particle size in the range of about 0.01 to about 1.0 micron and in an amount of between about 0.01% and about 0.2% by weight of the water. The water including the semiconductor mixture is exposed to band-gap photons for a time sufficient to affect an oxidation of the oxidizable contaminant to purify the water. Crossflow membrane filtration was used to separate the purified water from the semiconductor particles. Cooper et al. show that the organic impurity carbon content of simulated reclamation waters at nominal 40 PPM level were reduced to parts per billion using a recirculation batch reactor.

Cooper et al, identified that one important aspect of the photocatalytic process is the adsorption of the organic molecules onto the extremely large surface area presented by the finely divided powders dispersed in the water. Cooper et al. further indicated that, in photoelectrochemical applications, advantage is taken of the fact that the solid phase (a metal oxide semiconductor) is also photo-active and that the generated charge carriers are directly involved in the organic oxidation. The adsorption of the band-gap photon by the semiconductor particle results in the formation of an electron (e$^-$)/hole(h$^+$) pair. Cooper et al. explain that the electrons generated in the conduction band react with solution oxygen forming the dioxygen anion (O$_{2-}$) species which subsequently undergo further reactions resulting in the production of the powerfully oxidizing hydroxyl radical species, .OH. These powerful oxidants are known to oxidize organic compounds by themselves. Additionally, Cooper et al. explain that the strongly oxidizing holes generated in the valence band have sufficient energy to oxidize all organic bonds.

In the reactor of Cooper et al., turbulence is necessary in order to ensure that the waste water contaminants and the photocatalytic titania particles are exposed to the UV light. Cooper et al. explain that the most basic considerations of photocatalyst light adsorption and its relationship to convective mixing. For a 0.1 wt % photocatalyst loading, experiments have shown that 90% of the light is absorbed within 0.08 cm. This is primarily due to the large UV absorption coefficient of the photocatalyst and therefore, most of the photoelectrochemistry occurs within this illuminated region. By operating the reactor of Cooper et al. with a Reynolds number (Re) of 4000, a significant portion of the photoactive region is ensured of being within the well mixed turbulent zone.

Santos et al. have reported in "Photocatalysis as a tertiary treatment for petroleum refinery wastewaters" published in Braz. J. Chem. Eng. vol. 23, No. 4, 2006 (the entire contents of which are incorporated herein by reference), photocatalysis for tertiary treatment for petroleum refinery wastewaters which satisfactorily reduced the amount of pollutants to the level of the regulatory discharge limits and oxidized persistent compounds that had not been oxidized in the biological treatment. The treatment sequence used by the refinery (REDUC/PETROBRAS, a Brazilian oil refinery) is oil/water separation followed by a biological treatment. Although the process efficiency in terms of biological oxygen demand (BOD) removal is high, a residual and persistent COD and a phenol content remains. The refining capacity of the refinery is 41,000 m$^3$/day, generating 1,100 m$^3$/h of wastewater, which are discharged directly into the Guanabara Bay (Rio de Janeiro). Treating the residual and persistent COD remains a priority.

Santos et al. conducted a first set of experiments carried out in an open 250 mL reactor containing 60 mL of wastewater. In the second set of experiments, a Pyrex® annular reactor containing 550 mL of wastewater was used (De Paoli and Rodrigues, 1978). The reaction mixtures inside the reactors were maintained in suspension by magnetic stirring. In all experiments, air was continuously bubbled through the suspensions. A 250 W Phillips HPL-N medium pressure mercury vapor lamp (with its outer bulb removed) was used as the UV-light source (radiant flux of 108 J·m$^{-2}$·s$^{-1}$ at $\lambda$>254 nm). In one set of experiments, the lamp was positioned above the surface of the liquid at a fixed height (12 cm). In the second set, the lamp was inserted into the well. All experiments by Santos et al. were performed at 25±1° C. The catalyst concentration ranged from 0.5 to 5.5 g L$^{-1}$ and the initial pH ranged from 3.5 to 9.

In one embodiment of the invention described herein, the insertion device(s) 3 would be placed inside quartz or glass fixtures within the waste water or would be placed on silica encapsulated structures within the waste water which, like the photocatalytic TiO$_2$, could be entrained in the waste water during the irradiation.

Upon irradiation with for example microwave or RF power, the insertion device(s) 3 would generate UV light in nearby presence of the photocatalytic agent. In other words for this embodiment, the insertion device(s) 3 are mixed along with the photocatalytic semiconductor particles in the waste water fluid stream, and the exterior activation energy source penetrates the container (e.g., a plastic or aluminum container) and irradiates the bulk of the waste water, producing UV light throughout the waste water which in turn drives the photocatalytic reactions. In one embodiment, the insertion device(s) 3 are complexed with the down converting particles or other energy modulation agents.

Photostimulation

Photostimulation is a field in which light is applied to in order to alter or change a physical property. For example, there has been an increased focus on the use of biodegradable polymers in consumer and biomedical fields. Polylactic acid (PLA) plastics and polyhydroxyalkanoates (PHA) plastics have been playing a vital role in fulfilling the objectives. But their relatively hydrophobic surfaces limit their use in various applications. Hence, there is a need to surface modify these film surfaces. Due to the lack of any modifiable side chain groups, workers have used a sequential two step photografting technique for the surface modification of these biopolymers. In step one, benzophenone was photografted on the film surface and in step two, hydrophilic monomers like acrylic acid and acrylamide were photopolymerized from the film surfaces.

Workers have found that UV irradiation could realize an effective graft copolymerization. UV-assisted photografting in ethanol has been used to grow hydrophilic polymers (e.g., poly(acrylic acid) and polyacrylamide) from the surfaces of PLA, PHA, and PLA/PHA blend films. In that work, a functional polyurethane (PU) surface was prepared by photo-grafting N,N-dimethylaminoethyl methacrylate (DMAEM) onto the membrane surface. Grafting copolymerization was conducted by the combined use of the photo-oxidation and irradiation grafting. PU membrane was photo-oxidized to introduce the hydroperoxide groups onto the surface, then the membrane previously immersed in monomer solution was irradiated by UV light. Results have shown prior to the invention that UV irradiation can realize graft copolymerization effectively.

In the invention described herein, these processes are expedited by the inclusion of the insertion device(s) 3 in dispersion in the fluid medium being used for photostimulation. Upon microwave or RF power irradiation, the insertion device(s) 3 would generate UV light permitting batch or bulk type processing to occur in parallel inside the container.

Photodeactivation

In many industrial processes, especially food and beverage industries, yeasts are used to produce changes in a medium such as the conversion of sugars in the raw product. One particularly prominent example is in the wine industry. Stopping the wine from fermenting any further would preserve the current level of sweetness. Likewise, allowing the wine to continue fermenting further would only make the wine less sweet with each passing day. Eventually the wine would become completely dry at which time the fermentation would stop on its own. This is because during the fermentation process yeast turns the sugar into alcohol.

Wanting to stop the fermentation process is all good in and of itself. But unfortunately, there is really no practical way to successfully stop a fermentation dead in its tracks. Additives such as sulphite and sorbate can be added to stabilize a fermented product and stop additional fermentation. Many winemakers will turn to sulfites such as that found in Sodium Bisulfite or Campden tablets for the answer. But, these two items are not capable of reliably killing enough of the yeast to guarantee a complete stop of the activity—at least not at normal doses that leave the wine still drinkable.

Once the bulk of the sulfites from either of these ingredients dissipate from the wine into the air—as sulfites do—there is a very strong chance that the remaining few live yeast cells will start multiplying and fermenting again if given enough time. This usually happens at a most inconvenient time, like after the wine has been bottled and stowed away.

Potassium sorbate is another ingredient that many winemakers consider when trying to stop a wine from fermenting any further. There is a lot of misunderstanding surrounding this product. It is typically called for by home wine making books when sweetening a wine. This is a situation where the fermentation has already completed and is ready for bottling. One adds the potassium sorbate along with the sugar that is added for sweetening.

The potassium sorbate stops the yeast from fermenting the newly added sugar. So, many winemakers assume potassium sorbate can stop an active fermentation as well, but, potassium sorbate does not kill the yeast at all, but rather it makes the yeast sterile. In other words, it impairs the yeast's ability to reproduce itself. But, it does not hinder the yeast's ability to ferment sugar into alcohol.

Ultraviolet light is known to destroy yeast cultures, but has restricted applications due to the inability of UV light to penetrate throughout the fluid medium. While heat can be used to destroy the yeast activity, cooking of the product may be premature or may produce undesirable changes in the consistency and taste. For liquid or fluid food products, the same techniques described above could be used for the application described here. For non-liquid products, energy modulation agents with little and preferably no toxicity (e.g. Fe oxides or titanium oxides) could be added. Here, the concentration of these additives would likely be limited by any unexpected changes in taste.

Here, UV light produced by the insertion device(s) 3 would deactivate the yeasts.

Photoactivated Cross-Linking and Curing of Polymers

In this application, the insertion device(s) 3 of the invention are provided and distributed into an uncured polymer based medium for the activation of photosensitive agents in the medium to promote cross-linking and curing of the polymer based medium. In one embodiment, the insertion device(s) 3 are provided with down-converting luminescent particles or other energy modulation agents prior to being added to the polymer.

For adhesive and surface coating applications, light activated processing is limited due to the penetration depth of UV light into the processed medium. In light activated adhesive and surface coating processing, the primary limitation is that the material to be cured must see the light—both in type (wavelength or spectral distribution) and intensity. This limitation has meant that one medium typically has to transmit the appropriate light. In adhesive and surface coating applications, any "shaded" area will require a secondary cure mechanism, increasing cure time over the non-shaded areas and further delaying cure time due to the existent of a sealed skin through which subsequent curing must proceed.

Conventionally, moisture-curing mechanisms, heat-curing mechanisms, and photo-initiated curing mechanisms are used to initiate cure, i.e., cross-linking, of reactive compositions, such as reactive silicones, polymers, and adhesives. These mechanisms are based on either condensation reactions, whereby moisture hydrolyzes certain groups, or addition reactions that can be initiated by a form of energy, such as electromagnetic radiation or heat.

The invention described herein can use any of the following light activated curing polymers as well as others known in the art to which the insertion device(s) 3 of the invention are added.

Photocuring with the Insertion Devices of this Invention

In this application, the insertion device(s) 3 of the invention are provided and distributed into an uncured polymer based medium for the activation of photosensitive agents in the medium to promote cross-linking and curing of the polymer based medium. For adhesive and surface coating applications, light activated processing is limited due to the penetration depth of UV light into the processed medium. In light activated adhesive and surface coating processing, the primary limitation is that the material to be cured must see the light—both in type (wavelength or spectral distribution) and intensity. This limitation has meant that one medium typically has to transmit the appropriate light. In adhesive and surface coating applications, any "shaded" area will require a secondary cure mechanism, increasing cure time over the non-shaded areas and further delaying cure time due to the existent of a sealed skin through which subsequent curing must proceed.

Conventionally, moisture-curing mechanisms, heat-curing mechanisms, and photo-initiated curing mechanisms are used to initiate cure, i.e., cross-linking, of reactive compositions, such as reactive silicones, polymers, and adhesives.

These mechanisms are based on either condensation reactions, whereby moisture hydrolyzes certain groups, or addition reactions that can be initiated by a form of energy, such as electromagnetic radiation or heat.

The invention described herein can use any of the following light activated curing polymers as well as others known in the art to which the insertion devices 3 of the invention are added.

Loctite Corporation has designed and developed UV and UV/moisture dual curable silicone compositions, which also demonstrate high resistance to flammability and combustibility, where the flame-retardant component is a combination of hydrated aluminand a member selected from the group consisting of organo ligand complexes of transition metals, organosiloxane ligand complexes of transition metals, and combinations thereof. See U.S. Pat. Nos. 6,281,261 and 6,323,253 to Bennington. These formulations are also suitable for the invention.

Other known UV photoactivatable silicones include silicones functionalized with, for example, carboxylate, maleate, cinnamate and combinations thereof. These formulations are also suitable for the invention. Other known UV photoactivatable silicones suitable for the invention include benzoin ethers ("UV free radical generator") and a free-radical polymerizable functional silicone polymers, as described in U.S. Pat. No. 6,051,625 whose content is incorporated herein by reference in its entirety. The UV free radical generator (i.e., the benzoin ether) is contained at from 0.001 to 10 wt % based on the total weight of the curable composition. Free radicals produced by irradiating the composition function as initiators of the polymerization reaction, and the free radical generator can be added in a catalytic quantity relative to the polymerizable functionality in the subject composition. Further included in these silicone resins can be silicon-bonded divalent oxygen atom compounds which can form a siloxane bond while the remaining oxygen in each case can be bonded to another silicon to form a siloxane bond, or can be bonded to methyl or ethyl to form an alkoxy group, or can be bonded to hydrogen to form silanol. Such compounds can include trimethylsilyl, dimethylsilyl, phenyldimethylsilyl, vinyldimethylsilyl, trifluoropropyldimethylsilyl, (4-vinylphenyl)dimethylsilyl, (vinylbenzyl)dimethylsilyl, and (vinylphenethyl)dimethylsilyl.

The photoinitiator component of this invention is not limited to those free radical generators given above, but may be any photoinitiator known in the art, including the aforementioned benzoin and substituted benzoins (such as alkyl ester substituted benzoins), Michler's ketone, dialkoxyacetophenones, such as diethoxyacetophenone ("DEAP"), benzophenone and substituted benzophenones, acetophenone and substituted acetophenones, and xanthone and substituted xanthones. Other desirable photoinitiators include DEAP, benzoin methyl ether, benzoin ethyl ether, benzoin isopropyl ether, diethoxyxanthone, chloro-thio-xanthone, azo-bisisobutyronitrile, N-methyl diethanolamine-benzophenone, and mixtures thereof. Visible light initiators include camphoquinone, peroxyester initiators and non-fluorene-carboxylic acid peroxyesters.

Commercially available examples of photoinitiators suitable for the invention include those from Vantico, Inc., Brewster, N.Y. under the IRGACURE and DAROCUR tradenames, specifically IRGACURE 184 (1-hydroxycyclohexyl phenyl ketone), 907 (2-methyl-1-[4-(methylthio)phenyl]-2-morpholino propan-1-one), 369 (2-benzyl-2-N,N-dimethylamino-1-(4-morpholinophenyl)-1-butanone), 500 (the combination of 1-hydroxy cyclohexyl phenyl ketone and benzophenone), 651 (2,2-dimethoxy-2-phenyl acetophenone), 1700 (the combination of bis(2,6-dimethoxybenzoyl-2,4,4-trimethyl pentyl) phosphine oxide and 2-hydroxy-2-methyl-1-phenyl-propan-1-one), and 819 [bis(2,4,6-trimethyl benzoyl)phenyl phosphine oxide] and DAROCUR 1173 (2-hydroxy-2-methyl-1-phenyl-1-propane) and 4265 (the combination of 2,4,6-trimethylbenzoyldiphenyl-phosphine oxide and 2-hydroxy-2-methyl-1-phenyl-propan-1-one); and IRGACURE 784DC (bis(.eta..sup.5-2,4-cyclopentadien-1-yl)-bis[2,6-difluoro-3-(1H-pyrrol-1-yl)phenyl]titanium).

Generally, the amount of photoinitiator (or free radical generators) should be in the range of about 0.1% to about 10% by weight, such as about 2 to about 6% by weight. The free radical generator concentration for benzoin ether is generally from 0.01 to 5% based on the total weight of the curable composition.

A moisture cure catalyst can also be included in an amount effective to cure the composition. For example, from about 0.1 to about 5% by weight, such as about 0.25 to about 2.5% by weight, of the moisture cure catalyst can be used in the invention to facilitate the cure process beyond that of photo-activated curing. Examples of such catalysts include organic compounds of titanium, tin, zirconium and combinations thereof. Tetraisopropoxytitanate and tetrabutoxytitanate are suitable as moisture cure catalyst. See also U.S. Pat. No. 4,111,890.

Included in the conventional silicone composition (and other inorganic and organic adhesive polymers) suitable for the invention are various inorganic fillers. For example, hollow microspheres supplied by Kish under the trade name Q-CEL are free flowing powders, white in color. Generally, these borosilicate hollow microspheres are promoted as extenders in reactive resin systems, ordinarily to replace heavy fillers, such as calcium carbonate, thereby lowering the weight of composite materials formed therewith. Q-CEL 5019 hollow microspheres are constructed of a borosilicate, with a liquid displacement density of 0.19 g/cm$^2$, a mean particle size of 70 microns, and a particle size range of 10-150 um. Other Q-CEL products are shown below in tabular form. Another commercially available hollow glass microsphere is sold by Kish under the trade name SPHERICEL. SPHEREICEL 110P8 has a mean particle size of about 11.7 microns, and a crush strength of greater than 10,000 psi. Yet other commercially available hollow glass microsphere are sold by the Schundler Company, Metuchen, N.J. under the PERLITE tradename, Whitehouse Scientific Ltd., Chester, UK and 3M, Minneapolis, Minn. under the SCOTCH-LITE trade name.

In general, these inorganic filler components (and others such as fumed silica) add structural properties to the cured composition, as well as confers flowability properties to the composition in the uncured state and increase the transmissivity for the UV cure radiation. When present, the fumed silica can be used at a level of up to about 50 weight percent, with a range of about 4 to at least about 10 weight percent, being desirable. While the precise level of silica may vary depending on the characteristics of the particular silica and the desired properties of the composition and the reaction product thereof, care should be exercised by those persons of ordinary skill in the art to allow for an appropriate level of transmissivity of the inventive compositions to permit a UV cure to occur.

Desirable hydrophobic silicas include hexamethyldisilazane-treated silicas, such as those commercially available from Wacker-Chemie, Adrian, Mich. under the trade designation HDK-2000. Others include polydimethylsiloxane-treated silicas, such as those commercially available from Cabot Corporation under the trade designation CAB-O-SIL N70-TS, or Degussa Corporation under the trade designation AEROSIL R202. Still other silicas include trialkoxylkyl silane-treated silicas, such as the trimethoxyoctyl silane-treated silica commercially available from Degussa under the trade designation AEROSIL R805; and 3-dimethyl dichlorosilane-treated silicas commercially available from Degussa under the trade designation R972, R974 and R976.

While these inorganic fillers have extended the use of conventional UV cured silicone systems to permit the curing of materials beyond a skin depth of UV penetration, these inorganic fillers alone do not overcome shadowing effects and suffer from UV scattering which effectively makes for a smaller penetration depth. In the invention described herein, the inclusion of these inorganic fillers along with phosphor or scintillator particles provide a mechanism by which uniform light activated cures can occur deep inside of the body of adhesive-solidified assemblies in regions that would normally be shadowed or not with the reach of external UV or other light sources.

Accordingly, in this example of the invention described herein, conventional silicone and polymeric adhesive or release or coating compositions are prepared using conventional mixing, heating, and incubation techniques. Included in these conventional compositions are the upconverter structures of the invention. These compositions can then be applied to surfaces of objects to be fixed together or to surfaces where a hard coating is desired or cast in a curable form for the production of molded objects. These compositions upon activation will produce radiant light for photoactivated cure of the polymer composition. The density of the phosphors in these compositions will depend on the "light transparency" of the luminescing particle containing composition.

U.S. Pat. No. 7,294,656 to Bach et al., the entire disclosure of which is incorporated herein by reference, describes a non-aqueous composition curable by UV radiation broadly containing a mixture of two UV curable urethane acrylates that have several advantages over conventional radiation-curable compositions. The Bache et al. compositions can be cured in a relatively short time using UV-C (200-280 nm), UV-B (280-320 nm), UV-A (320-400 nm) and visible (400 nm and above) radiation. In particular, Bache et al. compositions can be cured using radiation having a wavelength of 320 nm or more. When fully cured (regardless of the type of radiation used), the Bach et al. compositions exhibit hardnesses and impact resistances at least comparable to conventional coatings.

In the invention described here, the light emitting insertion devices of the invention are added to these Bach et al. compositions. Due to the fact that the exterior energy source penetrates deeper into the entirety of the Bach et al. compositions, thicker surface coatings can be realized. Further, the coatings can be applied to intricate surfaces having for example been prepared with recesses or protrusions.

For example, one suitable light activated polymer compound includes UV curing silicones having methacrylate functional groups. U.S. Pat. No. 4,675,346 to Lin, the disclosure of which is hereby expressly incorporated herein by reference, is directed to UV curable silicone compositions including at least 50% of a specific type of silicone resin, at least 10% of a fumed silica filler and a photoinitiator, and cured compositions thereof. Other known UV curing silicone compositions suitable for the invention include organopolysiloxane containing a (meth)acrylate functional group, a photosensitizer, and a solvent, which cures to a hard film. Other known UV curing silicone compositions suitable for the invention include compositions of an organopolysiloxane having an average of at least one acryloxy and/or methacryloxy group per molecule; a low molecular weight polyacrylyl crosslinking agent; and a photosensitizer.

Accordingly, in this example of the invention described herein, conventional silicone and polymeric adhesive or release or coating compositions are prepared using conventional mixing, heating, and incubation techniques. Included in these conventional compositions are the insertion device(s) 3 of the invention. These compositions can then be applied to surfaces of objects to be fixed together or to surfaces where a hard coating is desired or cast in a curable form for the production of molded objects. These compositions upon activation will produce radiant light for photoactivated cure of the luminescing particle containing polymer composition. The density of the upconverter structures in these compositions will depend on the "light transparency" of the luminescing particle containing composition. Where these compositions contain a significant amount of the inorganic filler as discussed above, the concentration of the insertion device(s) 3 can be reduced for example as compared to a composition with a black color pigment where the light transparency will be significantly reduced.

U.S. Pat. No. 7,294,656 to Bach et al., the entire disclosure of which is incorporated herein by reference, describes a non-aqueous composition curable by UV radiation broadly containing a mixture of two UV curable urethane acrylates that have several advantages over conventional radiation-curable compositions. The Bache et al. compositions can be cured in a relatively short time using UV-C (200-280 nm), UV-B (280-320 nm), UV-A (320-400 nm) and visible (400 nm and above) radiation. In particular, Bache et al. compositions can be cured using radiation having a wavelength of 320 nm or more. When fully cured (regardless of the type of radiation used), the Bach et al. compositions exhibit hardnesses and impact resistances at least comparable to conventional coatings.

In the invention described here, insertion devices 3 are added to these Bach et al. compositions. Due to the fact that the exterior energy source penetrates deeper into the entirety of the Bach et al. compositions, thicker surface coatings can be realized. Further, the coatings can be applied to intricate surfaces having for example been prepared with recesses or protrusions.

Treatment of Cell-Proliferation Disorders with the Insertion Devices

In a preferred embodiment of the invention, a subject is administered an activatable pharmaceutical agent including at least one photoactive drug. The insertion device(s) 3 are inserted in the subject preferably in vicinity of the diseased site. UV light (or visible light) from the insertion device(s) 3 activates the at least one photoactive drug inside the subject to thereby treat the subject for the cell proliferation disorder.

Alternatively, or in addition, another aspect of the invention includes a method for treating a subject carrying a virus in which the method provides within the subject at least one photoactive drug for treatment of the subject carrying the virus and inserts one of more insertion devices inside the subject. The at least one photoactive drug is activated directly or indirectly at the target inside the subject by UV light (or visible light) from the insertion devices 3 (or light from energy modulation agents) to thereby treat the subject carrying the virus.

Mechanisms included in the invention can involve photoactivation of a drug such as a psoralen or its derivatives or an alkylating agent. Mechanisms included in the invention can involve the formation of highly reactive oxygen species, such as singlet oxygen. Any of these mechanisms can be used in combination or selectively to treat a subject with a cell proliferation disorder, or who is carrying viruses and/or has associated disorders or symptoms thereof. In one embodiment, the UV light (or visible light) from the insertion devices can be used to activate an alkylating agent (e.g., iodonophthylazide) for its attachment to a virus. In one embodiment, the UV light (or visible light) from the insertion devices can be used to activate a psoralen (or a derivative or substitute thereof) for treatment of a bacterial infection or other disorders in the patient. In one embodiment, one wavelength of the UV light (or visible light) from the insertion devices can be used to activate an alkylating agent (e.g., iodonophthylazide) for its attachment to a virus, while another different wavelength of the UV light (or visible light) from the insertion devices can be used to activate a psoralen (or a derivative or substitute thereof) for treatment of a bacterial infection or other disorders in the patient. In one embodiment, one wavelength can be used to activate an alkylating agent or a psoralen, while another wavelength is used for a different purpose such as for example production of singlet oxygen (i.e., highly reactive oxygen species) or for production of sterilizing UV light or to promote cell growth or reduce inflammation, etc.

In various embodiments, one or more wavelengths of the UV light (or visible light) from the insertion devices could be used for treatment a host or arrest of viruses such as *Ebola*, West Nile, encephalitis, HIV, etc., and/or for the regulation and control of biological responses having varying degrees of apoptosis (the process of programmed cell death PCD) and necrosis (the premature death of cells and living tissue typically from external factors). In necrosis, factors external to the cell or tissue, such as infection, toxins, or trauma that result in the unregulated digestion of cell components. In contrast, apoptosis is a naturally occurring programmed and targeted cause of cellular death. While apoptosis often provides beneficial effects to the organism, necrosis is almost always detrimental and may be fatal.

In various embodiments of this invention, the alkylating agent can be at least one or more of drugs from the iodonophthylazide family, such as 1,5-iodonaphthylazide (INA). These photoactivatable compounds are non-toxic, hydrophobic compounds that can penetrate into the innermost regions of biological membrane bilayers and selectively accumulate in such inner membrane regions. Upon irradiation with UV light (or visible light) from the insertion device(s) 3 or light from energy modulation agents, generated inside or nearby the membrane region, it is believed that a reactive derivative of the compound is generated that binds to membrane proteins deep in the lipid bilayer. This process inactivates integral membrane proteins embedded in the membrane while maintaining the structural integrity and activity of the proteins that protrude from the extracellular surface of the membrane. In one aspect of the invention, the inactivated agent constitutes a vaccine created inside the subject animal or bird or human with the vaccine specific to the viral or bacterial infection of the animal or bird or human.

In various embodiments of this invention, a photoactive drug such as a psoralen or its derivatives is used separately or in conjunction with at least one alkylating agent. When using a psoralen, the psoralen is photactivated inside the cell by ultraviolet or visible light generated within the cell or nearby the cell by the UV light (or visible light) from the insertion devices or by light from energy modulation agents. The activated psoralen attaches to the virus's genetic contents, prevents its replication, and causes local cell death (one form of treatment). Alternatively or in addition, the psoralen-inactivated virus can induce an autoimmune response from the animal or bird or human resulting in the body effectively eliminating untreated viruses in other regions of the body.

In one embodiment of the invention, 1,5-iodonaphthyl azide (INA) is employed as a photoactivatable hydrophobic compound. INA is a nontoxic hydrophobic compound. The structure for 1,5-iodonaphthyl azide (INA) is provided below.

Upon exposure to cells, the photoactivatable hydrophobic compounds can penetrate into the innermost regions of biological membrane bilayers and will accumulate selectively in these regions. Upon irradiation with ultraviolet light (e.g., 320 to 400 nm) generated (or otherwise provided) internally within the animal or bird or human subject by the UV light (or visible light) from the insertion device(s) 3 or light from energy modulation agents, it is believed that a reactive derivative is generated that binds to membrane proteins deep in the lipid bilayer.

In another embodiment of the invention, the photoactivatable hydrophobic compounds of the invention can be used for inactivation of viruses, bacteria, parasites and tumor cells using visible light. However, when visible light is used a photosensitizer, a chromophore is typically needed unless the photoactive drug is developed to be activated directly by visible light. A photosensitizer chromophore has an absorption maximum in the visible light range and can photosensitize the photoactivatable hydrophobic compounds of the invention. In general, the photosensitizer chromophores have absorption maxima in the range of about 450 to about 525 nm or about 600 to about 700 nm. Suitable photosensitizer chromophores can include one or more of a porphyrin, chlorin, bacteriochlorin, purpurin, phthalocyanine, naphthalocyanine, merocyanines, carbocyanine, texaphyrin, non-tetrapyrrole, or other photosensitizers known in the art. Specific examples of photosensitizer chromophores include fluorescein, eosin, bodipy, nitro-benzo-diazol (NBD), erythrosine, acridine orange, doxorubicin, rhodamine 123, picoerythrin and the like.

As provided in various embodiments of the invention, viruses, bacteria, parasites and tumor cells and other infectious structures and microorganisms can be inactivated by exposure to photoactivatable hydrophobic compounds which were themselves activated by light generated internally within the animal or bird or human subject by UV light (or visible light) from the insertion devices or light from energy modulation agents or light from photosensitizer chromophores. In various embodiments, the photoactivatable hydrophobic compound is 1,5-iodonaphthyl azide (INA) or a related compound. In one embodiment of the invention, the virus, parasite or tumor cell is contacted with the recently photoactivated hydrophobic compound, which was photoactivated by ultraviolet light generated internally using the energy modulation agents of the invention. If the virus, parasite, tumor cell or other infectious structures and microorganisms are contacted with both the photoactivatable hydrophobic compound and a photosensitizer chromophore that absorbs visible light, then visible light generated internally by UV light (or visible light) from the insertion device(s) 3 or light from energy modulation agents or light from photosensitizer chromophores can photoactivate the photoactivatable hydrophobic compound. Accordingly, in one embodiment, exposure to internally generated ultraviolet light directly photoactivates the photoactivatable hydrophobic compound within viral and cellular membranes. In one embodiment, exposure to internally generated visible light first photoactivates the photosensitizer chromophore, which then activates or photosensitizes the photoactivatable hydrophobic compound within viral or cellular membranes.

In either case, a reactive derivative of the photoactivatable hydrophobic compound is generated that binds to membrane proteins deep within the lipid bilayer. This process is believed to cause specific inactivation of integral membrane proteins embedded in the membrane, while maintaining the integrity and activity of proteins that protrude outside of the membrane.

The invention with internally generated light can provide a method that can inactivate a wide variety of viruses, bacteria, parasites and tumor cells in a way that the inactivated species can be safely used as immunological compositions or vaccines to inhibit the disease they cause. The activated drug agents (generated indirectly from the UV light (or visible light) from the insertion device(s) 3 activating a photoactivatable drug) kill the organism or cell in a specific manner that maintains its structure and conformation. Hence, the structure of the inactivated virus/cell is similar to that of the live virus/cell. In this way, the immunogenicity of the organism or cell as a whole is maintained and can be safely used to stimulate the immune system of a subject animal or bird or patient. Similarly, in one aspect of the invention, the inactivated viruses, bacteria, cancer cells, or parasites generated inside the animal or bird or human subject can be used for vaccination without causing disease or other negative side effects.

Hence, the INA internal treatment procedures generate inactive viruses inside the subject that can be used in a manner similar to aldrithiol inactivated HIV (developed by the AIDS vaccine program SAIC). Alternatively, the INA-internal-inactivation procedures of this invention can be used in conjunction with aldrithiol inactivation procedures to generate inactive HIV that comply with the requirements of the FDA. Thus, in one aspect of this invention, two mechanistically independent methods of inactivation can be used to provide a prophylactic AIDS or HIV vaccine.

In one aspect of the invention, prevention or treatment of microbial infections, viral infections, parasitic infections, prion infection or cancer is intended to include the alleviation of or diminishment of at least one symptom typically associated with the infection or cancer. Prevention or treatment also includes alleviation or diminishment of more than one symptom. Ideally, treatment with the internally inactivated agents of the invention generates immunity in the animal or bird or human towards the agent while prevention by the inactivated agents of the invention substantially eliminates the symptoms associated with the infection or cancer.

In various embodiments of the invention, infections that can be treated by the present internally activated drug agents (generated from the UV light (or visible light) from the insertion device(s) 3 activating a photoactivatable drug) include infections by any target infectious organisms and structures that can infect a mammal or other animal or a bird. Such target infectious organisms and structures include, but are not limited to, any virus, bacterium, fungus, single cell organism, prion conformations or parasite that can infect an animal, including mammals. For example, target microbial organisms include viruses, bacteria, fungi, yeast strains and other single cell organisms. In another embodiment, the inactivated agents of the invention can give rise to immunity against both gram-negative and gram-positive bacteria.

Exemplary viral infections that can be treated by this invention include infections by any virus that can infect animals (including but not limited to mammals or birds), including enveloped and non-enveloped viruses, DNA and RNA viruses, viroids, and prions. Hence, for example, infections or unwanted levels of the following viruses and viral types can be treated internally: human immunodeficiency virus (HIV), simian immunodeficiency virus (SIV), hemorrhagic fever viruses, hepatitis A virus, hepatitis B virus, hepatitis C virus, poxviruses, herpes viruses, adenoviruses, papovaviruses, parvoviruses, reoviruses, orbiviruses, picornaviruses, rotaviruses, alphaviruses, rubiviruses, influenza virus type A and B, flaviviruses, coronaviruses, paramyxoviruses, morbilliviruses, pneumoviruses, rhabdoviruses, lyssaviruses, orthmyxoviruses, bunyaviruses, phieboviruses, nairoviruses, hepadnaviruses, arenaviruses, retroviruses, enteroviruses, rhinoviruses and the filovirus.

Infections or unwanted levels of the following target viruses and viral types that are believed to have potential as biological weapons can be treated, prevented or addressed by the internally inactivated agents of this invention: hemorrhagic fever viruses (HFVs), Chikungunya virus, Japanese encephalitis virus, Monkey pox virus, variola virus, Congo-Crimean hemorrhagic fever virus, Junin virus, Omsk hemorrhagic fever virus, Venezuelan equine encephalitis virus, Dengue fever virus, Lassa fever virus, Rift valley fever virus, Western equine encephalitis virus, Eastern equine encephalitis virus, Lymphocytic choriomeningitis virus, Russian Spring-Summer encephalitis virus, White pox, *Ebola* virus, Machupo virus, Smallpox virus, Yellow fever virus, Hantaan virus, Marburg virus, and Tick-borne encephalitis virus.

Similarly, infections or unwanted levels of the following examples of target microbial organisms can be treated by this invention: *Aeromonas* spp. (including, for example, *Aeromonas hydrophila, Aeromonas caviae* and *Aeromonas sobria*), *Bacillus* spp. (including, for example, *Bacillus cereus, Bacillus anthracis* and *Bacillus thuringiensis*), *Bacteroides* spp. (including, for example, *B. fragilis, B. thetaiotaomicron, B. vulgatus, B. ovatus, B. distasonis, B. uniformis, B. stercoris, B. eggerthii, B. merdae*, and *B. caccae*), *Campylobacter* spp. (including, for example, *Campylobacter jejuni, Campylobacter laridis*, and *Campylobacter hyointestinalis*), *Clostridium* spp. (such as the pathogenic clostridia including all types of *Clostridium botulinum* (including those in Groups I, II, III and IV, and including those that produce botulism A, B, C, D, E, F and G), all types of *Clostridium tetani*, all types of *Clostridium difficile*, and all types of *Clostridium perfringens*), *Ebola* spp. (e.g. EBOV Zaire), *Enterobacter* spp. (including, for example, *Enterobacter aerogenes* (also sometimes referred to as *Klebsiella mobilis*), *Enterobacter agglomerans* (also sometimes referred to as *Pantoea agglomerans*), *Enterobacter amnigenus, Enterobacter asburiae, Enterobacter cancerogenus* (also sometimes referred to as *Enterobacter taylorae* and/or *Erwinia cancerogena*), *Enterobacter cloacae, Enterobacter cowanii, Enterobacter dissolvens* (also sometimes referred to as *Erwinia dissolvens*), *Enterobacter gergoviae, Enterobacter hormaechei, Enterobacter intermedium, Enterobacter intermedius* (also sometimes referred to as *Enterobacter intermedium*), *Enterobacter kobei, Enterobacter nimipressuralis* (also sometimes referred to as *Erwinia nimipressuralis*), *Enterobacter sakazakii*, and *Enterobacter taylorae* (also sometimes referred to as *Enterobacter cancerogenus*)), *Enterococcus* spp. (including, for example, Vancomycin Resistant *Enterococcus* (VRE), *Enterococcus faecalis, Enterococcus faecium, Enterococcus*

*durans, Enterococcus gallinarum*, and *Enterococcus casseliflavus*), *Escherichia* spp. (including the enterotoxigenic (ETEC) strains, the enteropathogenic (EPEC) strains, the enterohemorrhagic (EHEC) strain designated *E. coli* O157: H7, and the enteroinvasive (EIEC) strains), *Gastrospirillum* spp. (including, for example, *Gastrospirillum hominis* (also sometimes now referred to as *Helicobacter heilmannii*), *Helicobacter* spp. (including, for example, *Helicobacter pylori* and *Helicobacter hepaticus*), *Klebsiella* spp. (including, for example, *Klebsiella pneumoniae, Klebsiella ozaenae, Klebsiella rhinoscleromatis, Klebsiella oxytoca, Klebsiella planticola, Klebsiella terrigena*, and *Klebsiella ornithinolytica*), *Salmonella* spp. (including, for example, *S. typhi* and *S. paratyphi* A, B, and C, *S. enteritidis*, and *S. dublin*), *Shigella* spp. (including, for example, *Shigella sonnei, Shigella boydii, Shigella flexneri*, and *Shigella dysenteriae*), *Staphylococcus* spp. (including, for example, *Staphylococcus aureus*, methicillin-resistant *Staphylococcus aureus* (MRSA), *Staphylococcus saprophyticus* and *Staphylococcus epidermis*), *Streptococcus* ssp. (including Groups A (one species with 40 antigenic types, *Streptococcus pyogenes*), B, C, D (five species (*Streptococcus faecalis, Streptococcus faecium, Streptococcus durans, Streptococcus avium*, and *Streptococcus bovis*)), F, and G, including *Streptococcus pneumoniae*), *Pseudomonas* spp. (including, for example, *Pseudomonas aeruginosa, Pseudomonas maltophilia, Pseudomonas fluorescens, Pseudomonas putida, Pseudomonas cepacia, Pseudomonas stutzeri, Pseudomonas mallei, Pseudomonas pseudomallei* and *Pseudomonas putrefaciens*), *Vibrio* spp. (including, for example, *Vibrio cholera* Serogroup O1 and *Vibrio cholera* Serogroup Non-01, *Vibrio parahaemolyticus, Vibrio alginolyticus, Vibrio furnissii, Vibrio carchariae, Vibrio hollisae, Vibrio cincinnatiensis, Vibrio metschnikovii, Vibrio damsela, Vibrio mimicus, Vibrio vulnificus*, and *Vibrio Yersinia* spp. (including, for example, *Yersinia pestis, Yersinia enterocolitica* and *Yersinia pseudotuberculosis*), *Neisseria, Proteus, Citrobacter, Aerobacter, Providencia, Serratia, Brucella, Francisella tularensis* (also sometimes referred to as *Pasteurella tularensis, Bacillus tularensis, Brucella tularensis*, tularemia, rabbit fever, deerfly fever, Ohara's disease, and/or Francis disease), and the like.

Thus, for example, various bacterial infections or unwanted levels of bacteria that can be treated, prevented or addressed by the present invention include but are not limited to those associated with anthrax (*Bacillus anthracis*), staph infections (*Staphylococcus aureus*), typhus (*Salmonella typhi*), food poisoning (*Escherichia coli*, such as O157:H7), bascillary dysentery (*Shigella dysenteria*), pneumonia (*Psuedomonas aerugenosa* and/or *Pseudomonas cepacia*), cholera (*Vibrio cholerae*), ulcers (*Helicobacter pylori*), *Bacillus cereus, Salmonella, Clostridium perfringens, Campylobacter, Listeria monocytogenes, Vibrio parahaemolyticus*, botulism (*Clostridium botulinum*), smallpox (variola major), listeriosis (*Listeria monocytogenes*), tularemia (*Francisella tularensis*), plague (*Yersinia pestis*; also sometimes referred to as bubonic plague, pneumonic plague, and/or black death) and others. *E. coli* serotype O157:H7 has been implicated in the pathogenesis of diarrhea, hemorrhagic colitis, hemolytic uremic syndrome (HUS) and thrombotic thrombocytopenic purpura (TTP). As indicated herein, the internally inactivated agents of this invention are also active against drug-resistant and multiply-drug resistant strains of bacteria, for example, multiply-resistant strains of *Staphylococcus aureus* and vancomycin-resistant strains of *Enterococcus faecium* and *Enterococcus faecalis*.

Fungal infections that can be treated or prevented by this invention include infections by fungi that infect a mammal or a bird, including *Histoplasma capsulatum, Coccidioides immitis, Cryptococcus neoformans, Candida* ssp. including *Candida albicans, Aspergilli* ssp. including *Aspergillus fumigatus, Sporothrix, Trichophyton* ssp., *Fusarium* ssp., *Tricosporon* ssp., *Pneumocystis carinii*, and *Trichophyton mentagrophytes*. Hence, for example, infections or unwanted levels of target fungi can be treated, prevented or addressed by the present inactivated agents. Such fungi also include fungal pathogens that may have potential for use biological weapons, including *Coccidioides immitis* and *Histoplasma capsulatum*.

Prions that are treatable in the invention are proteins that can access multiple conformations, at least one of which is beta-sheet rich, infectious and self-perpetuating in nature. These infectious proteins show several remarkable biological activities, including the ability to form multiple infectious prion conformations, also known as strains or variants, encoding unique biological phenotypes, and to establish and overcome prion species (transmission) barriers. See, e.g., Tessier et al., Unraveling infectious structures, strain variants and species barriers for the yeast prion [PSI+], Nat. Struct. Mol. Biol. 2009 June; 16(6):598-605.

Cancers that can be treated by this invention include solid mammalian tumors as well as hematological malignancies. Solid mammalian tumors include cancers of the head and neck, lung, mesothelioma, mediastinum, esophagus, stomach, pancreas, hepatobiliary system, small intestine, colon, colorectal, rectum, anus, kidney, urethra, bladder, prostate, urethra, penis, testis, gynecological organs, ovaries, breast, endocrine system, skin central nervous system; sarcomas of the soft tissue and bone; and melanoma of cutaneous and intraocular origin. Hematological malignancies include childhood leukemia and lymphomas, Hodgkin's disease, lymphomas of lymphocytic and cutaneous origin, acute and chronic leukemia, plasma cell neoplasm and cancers associated with AIDS. In addition, a cancer at any stage of progression can be treated, such as primary, metastatic, and recurrent cancers. Both human and veterinary uses are contemplated.

Besides cancers, other disorders of the lymph nodes (such as for example viral and/or bacterial infections) can be treated by this invention. Accordingly, in one embodiment of the invention, there is provided a method for treating a subject with a virus or a bacterium which 1) provides within lymph nodes of the subject at least one photoactive or photoactivatable drug for treatment of the virus or the bacterium, and 2) applies initiation energy from at least one source to the lymph nodes. The method 3) activates by the UV light (or visible light) from the insertion device(s) 3 directly or indirectly the at least one photoactive or photoactivatable drug at the target inside the lymph nodes. Inside the lymph nodes, the method 4) reacts the activated drug with the virus or bacterium to inactivate the virus or the bacterium to thereby treat the subject.

Generalized Applications

The invention as described above can be viewed for its following applications in both medical and non-medical uses. Light or energy from the insertion device(s) 3 as noted above can produce a change in a medium in which the insertion device(s) 3 are in a vicinity of, whether or not the insertion device(s) 3 are interior or proximate the medium being treated. The changes induced can be changes in biological or non-biological medium.

The change produced can cure a radiation-curable medium by activating a photoinitiator in the radiation-curable medium. In this case, the emitted light or energy can be of a wavelength appropriate to induce photo-catalytic effects such as coupling to a photoinitiator or a UV cross-linking agent to produce curing in the uncured medium. Curing or polymerization of the medium results in the formation of a partial or complete three-dimensional network. The radiation-curable medium can be cured by activating a photoinitiator in the radiation-curable medium. For way of contrast, an uncured state of a material can be considered a state at which the material exhibit liquid-like behavior with a viscosity that can be high or that can be low. The cured state typically results in a state at which the material exhibits solid-like or rubbery-like behavior or a visco-elastic behavior and can result in a state where limited flow under an applied stress is produced.

The change produced can result in a photo-stimulated change to a medium. The change produced can result in a radiation cured medium. The change produced can result in a sterilized medium. The change produced can activate a therapeutic drug.

For many applications, the insertion device(s) 3 can be activated by signals transmitted from low frequency sources such as microwave or radio frequency irradiation. In one embodiment of the invention, reception of the microwave or radio frequency radiation by the insertion device(s) 3 results in subsequent emission at visible and/or ultraviolet light.

In one embodiment, the invention utilizes microwave or radiofrequency energy to trigger light generation from the insertion device(s) 3, whose light emission in turn produces a number of the physical and biological changes described above.

In one embodiment of the invention, at least one activatable pharmaceutical agent that is capable of activation a predetermined cellular change when activated is administering to a subject. Light or energy from the insertion device(s) 3 interacts with the at least one activatable pharmaceutical agent to activate the activatable pharmaceutical agent in situ, thus causing the predetermined cellular change to occur in the medium of the subject.

In one embodiment of the invention, the cell proliferation disorder being treated by light from the insertion device(s) 3 is at least one member selected from the group consisting of cancer, bacterial infection, viral infection, immune rejection response, autoimmune disorders, aplastic conditions, and combinations thereof. In one embodiment of the invention, the activatable pharmaceutical agent is a photoactivatable agent activatable by light from the insertion device(s) 3. The activatable pharmaceutical agent can be selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones.

In one embodiment of the invention, the pharmaceutical agent activated by light from the insertion device(s) 3 is a psoralen, a coumarin, a porphyrin or a derivative thereof. In one embodiment of the invention, the pharmaceutical agent is 8-MOP or AMT. In one embodiment of the invention, the activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematophorphyrin, and phthadocyanine.

In one embodiment of the invention, the activatable pharmaceutical agent is coupled to a carrier that is capable of binding to a receptor site. The carrier can be one selected from insulin, interleukin, thymopoietin or transferrin. In one embodiment of the invention, the activatable pharmaceutical agent is coupled to the carrier by a covalent bond. In one embodiment of the invention, the activatable pharmaceutical agent is coupled to the carrier by non-covalent bond. In one embodiment of the invention, the receptor site is one selected from nucleic acids of nucleated cells, antigenic sites on nucleated cells, or epitopes.

In one embodiment of the invention, the pharmaceutical agent has affinity for a target cell. In one embodiment of the invention, the activatable pharmaceutical agent is capable of being preferentially absorbed by a target cell. In one embodiment of the invention, the predetermined cellular change is apoptosis in a target cell.

In one embodiment of the invention, the activatable pharmaceutical agent causes an auto-vaccine effect in the subject that reacts with a target cell. The auto-vaccine effect can be generated in a joint or lymph node. In one embodiment of the invention, the activatable pharmaceutical agent is a DNA intercalator or a halogenated derivative thereof.

In one embodiment of the invention, light or energy from the insertion device(s) 3 is applied to a target structure in a subject in need of treatment, wherein the light contacts the target structure and induces a predetermined change in the target structure in situ in the medium of the subject, and the predetermined change modifies the target structure and modulates the biological activity of the target structure. In this embodiment, the emitted light or energy can induce a predetermined change in the target structure with or without an energy modulator or photoactive agent.

In one embodiment, an energy modulation agent can be administered to the subject which adsorbs, intensifies or modifies the light emitted from insertion device(s) 3 into an energy that effects the predetermined change in the target structure. In this embodiment, the energy modulation agent can be specifically located around, on, or in the target structure. In this embodiment, the energy modulation agent can also transform the initiation electromagnetic energy into a photonic or another electromagnetic energy that effects the predetermined change in the target structure. In this embodiment, the energy modulation agent can decrease the wavelength of the initiation energy. In this embodiment, the energy modulation agent can increase the wavelength of the initiation energy. In this embodiment, the energy modulation agent(s) can include one or more members selected from a biocompatible fluorescing metal nanoparticle, fluorescing metal oxide nanoparticle, fluorescing metal coated metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a biocompatible phosphorescent molecule, a combined electromagnetic energy harvester molecule, and a lanthanide chelate exhibiting intense luminescence.

In one embodiment, the predetermined change can or cannot result in destruction, lysis orinactivation of the target structure. In this embodiment, the predetermined change can enhance an activity of the target structure. The activity enhanced can be energy emission from the target, which then mediates, initiates or enhances a biological activity of other target structures in the subject, or of a second target structure.

In one embodiment, the target structure can be at least one of a eukaryotic cell, a prokaryotic cell, a subcellular structure. The subcellular structure can be a cell membrane, a nuclear membrane, cell nucleus, nucleic acid, mitochondria, ribosome, or other cellular organelle or component. In this embodiment, the target structure can be at least one of an extracellular structure, a virus or prion, a cellular tissue.

In one embodiment, the predetermined change can result in treatment of a condition, disorder or disease in the subject. The condition, disorder or disease can be at least one of a cancer, a disease occurring in a soft tissue and/or cartilage, a disease occurring in bone tissue, a chronic pain, an autoimmune disease, a prion, viral, bacterial, fungal, or parasitic infection, a disease characterized by varicose veins, a disease characterized by an enlarged prostate, a disease characterized by retinal injuries and other ocular diseases, a disease characterized by a behavioral, perceptional and/or cognitive disorder, or Parkinson's disease.

In one embodiment, the predetermined change can be a wound healing, an enhancement of tissue growth, nerve regeneration or sensory regeneration/restoration, reduction or removal of fat deposits (liposuction), nerve (brain) imaging and stimulation or direct control of brain cell activity with light, modulation of cell death (apoptosis), modulating cell growth and division, modulation of an activity, quantity, or number of intracellular components in a cell, or modulation of an activity, quantity, or number of extracellular components produced by, excreted by, or associated with a cell.

In one embodiment, heat can be generated in the target structure from the light or energy from insertion device(s) 3, and the heat can enhance the induction of the predetermined change. In this embodiment, the predetermined change can modify the target structure and modulate the biological activity of the target structure thus treating a condition, disorder or disease affecting the target structure.

Computer-Assisted Control

Figure 3:
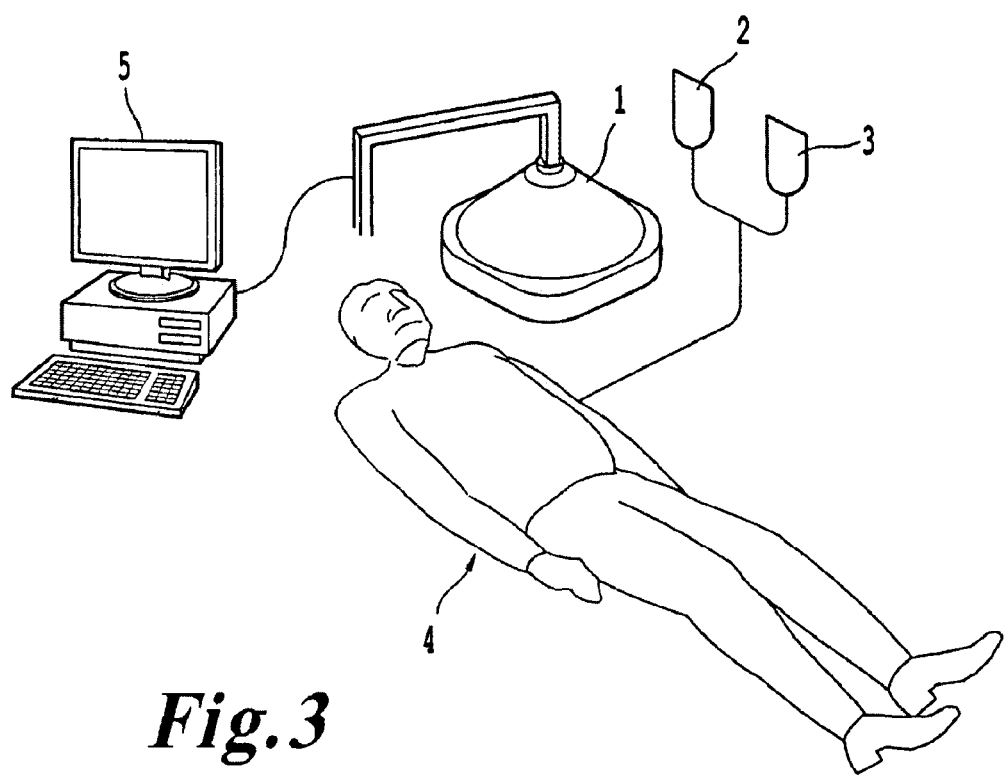
FIG. 3 is a schematic of an exemplary system according to one embodiment of the invention having an initiation energy source directed at a subject to activate the insertion device(s) of the invention.

FIG. 3 illustrates a system according to one exemplary embodiment of the invention. Referring to FIG. 3, an exemplary system according to one embodiment of the invention may have an initiation energy source 1 directed at the subject 4. An activatable pharmaceutical agent 2 and an insertion device 3 can be administered to the subject 4. The initiation energy source may additionally be controlled by a computer system 5 that is capable of directing the delivery of the initiation energy (e.g., radio-wave or microwave communications).

In another embodiment, there is also provided a computer implemented system for designing and selecting suitable combinations of initiation energy source, energy transfer agent, and activatable pharmaceutical agent to provide in a vicinity of the insertion device(s) 3 when inserted into a medium to be treated or a subject or patient, comprising:

a central processing unit (CPU) having a storage medium on which is provided:

a database of excitable compounds;

a first computation module for identifying and designing an excitable compound (e.g., a photoactivatable drug) that optionally is capable of binding with a target cellular structure or component; and a second computation module predicting the UV light (or visible light) dose or flux from the insertion device(s) 3 needed for excitation of the excitable compound, wherein the system, upon selection of a target cellular structure or component, computes an excitable compound that is capable of interacting with the target structure.

The computer-implemented system according to one embodiment of the invention may have a central processing unit (CPU) connected to a memory unit, configured such that the CPU is capable of processing user inputs and selecting a combination of initiation source (or initiation energies or distances), activatable pharmaceutical agent, and energy modulation or energy transfer agents for use in a method of the invention along with the insertion device(s) 3.

The computer-implemented system according to one embodiment of the invention includes (or is programmed to act as) a control device configured to calculate and provide control instructions to the insertion device(s) 3 for a prescribed ultraviolet light exposure. For example, the computer system 5 shown in FIG. 3 can include a central processing unit (CPU) having a storage medium on which is provided: a database of excitable compounds, a first computation module for a photoactivatable agent or energy transfer agent, and a second computation module predicting the requisite ultraviolet or visible flux needed to sufficiently activate the energy transfer agent or photoactivatable agent.

A more thorough discussion of the computer system 5 is provided below in reference to FIG. 4. As discussed below in more detail, the initiation energy source 1 can be an external energy source or an energy source located at least partially in a biological or non-biological medium 4. As discussed elsewhere in more detail, activatable agents 2 and/or energy modulation agents and/or plasmonics agents (which enhance either the ultraviolet or visible flux from the insertion device(s) 3) can be introduced into the medium so as to directly or indirectly produce a change in the biological or non-biological medium.

Figure 4:
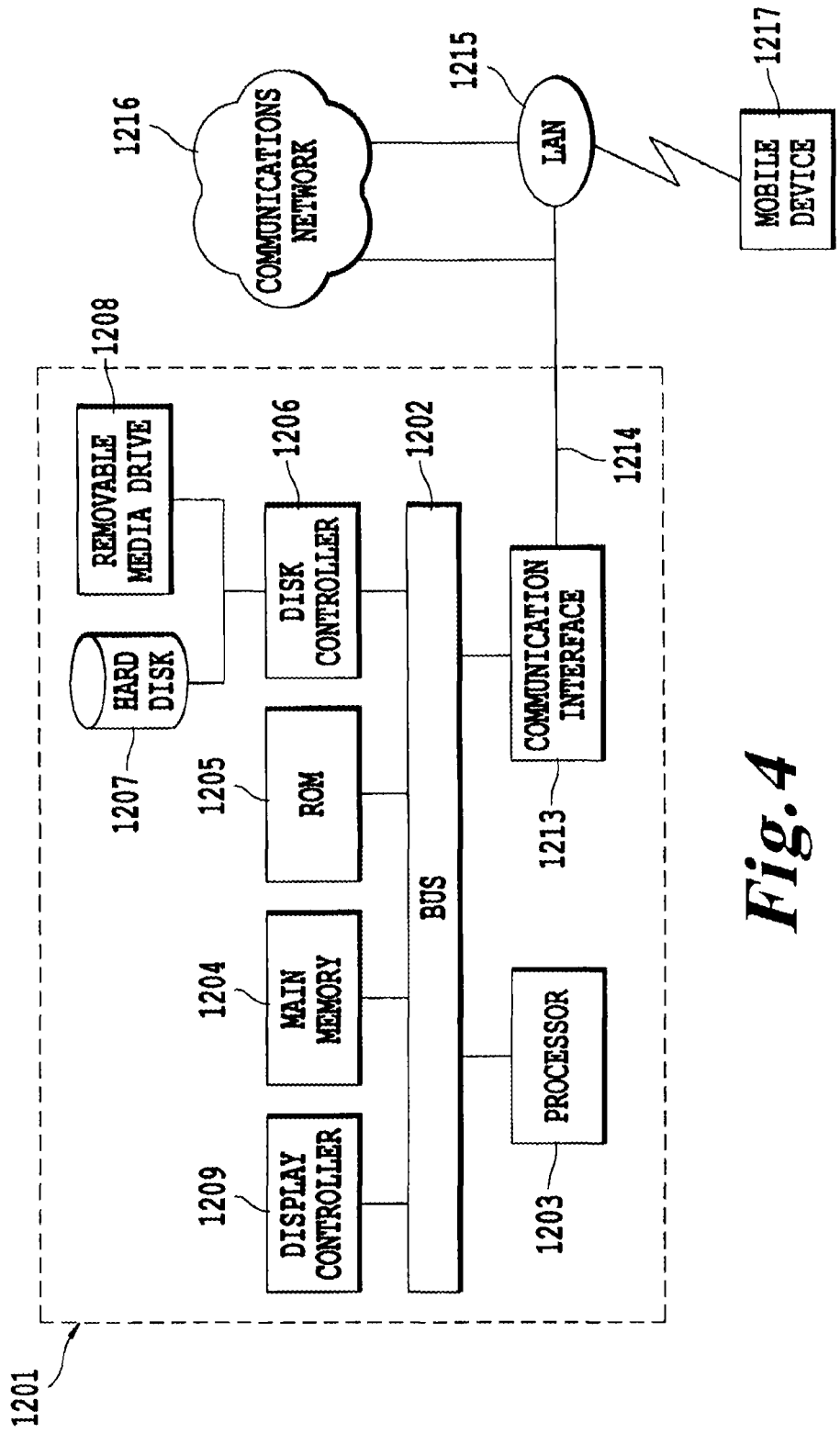
FIG. 4 illustrates a computer system for implementing various embodiments of the invention.

FIG. 4 illustrates a computer system 1201 for implementing various embodiments of the invention. The computer system 1201 may be used as the computer system 5 to perform any or all of the functions described above. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable read only memory (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display, such as a cathode ray tube (CRT), for displaying information to a computer user. The computer system includes input devices, such as a keyboard and a pointing device, for interacting with a computer user and providing information to the processor 1203. The pointing device, for example, may be a mouse, a trackball, or a pointing stick for communicating direction information and command selections to the processor 1203 and for controlling cursor movement on the display. In addition, a printer may provide printed listings of data stored and/or generated by the computer system 1201.

The computer system 1201 performs a portion or all of the processing steps (or functions) of this invention in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the invention includes software for controlling the computer system 1201, for driving a device or devices for implementing the invention, and for enabling the computer system 1201 to interact with a human user (i.e., operator). Such software may include, but is not limited to, device drivers, operating systems, development tools, and applications software. Such computer readable media further includes the computer program product of the invention for performing all or a portion (if processing is distributed) of the processing performed in implementing the invention.

The computer code devices of the invention may be any interpretable or executable code mechanism, including but not limited to scripts, interpretable programs, dynamic link libraries (DLLs), Java classes, and complete executable programs. Moreover, parts of the processing of the invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications which can be used along with microwave broadcast to communicate to the insertion device(s) 3.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213. Moreover, the network link 1214 may provide a connection through a LAN 1215 to a mobile device 1217 such as a personal digital assistant (PDA) laptop computer, or cellular telephone.

In one embodiment, there is provided a system for production of emitted light internal to a medium or internal to a human or animal subject. The system includes 1) a source configured to produce an initiation signal penetrating at least a part of the medium or the human or animal subject and 2) an insertion device having an electronics assembly unit. The assembly unit includes 1) an emitter configured to emit light of a predetermined type to treat a disease or disorder in the human or animal subject or to produce a change in the medium and 2) a receiver that receives the signal, 3) a transponder (including for example components of computer system 1201 describe above) having the ability to receive, process and emit a signal (optionally signals for an iCode Philips chip) The assembly unit is configured, upon receiving the signal, to power the emitter thereby emitting the light interior the human or animal subject or interior the medium.

As noted above, the iCode Philips chip is a compliant transponder that has fast access and read/write times. The higher frequency operation allows communication rates up to 53 kbaud. The iCode Philips chip hasflexible memory structure and requires for only a few turns of wire or printed foil tracks for the antenna.

In one embodiment, there is provided a system for production of emitted light internal to a medium or internal to a human or animal subject. The system includes 1) a source configured to produce an initiation signal penetrating at least a part of the medium or the human or animal subject and 2) an insertion device having an electronics assembly unit. The assembly unit includes 1) an emitter configured to emit light of a predetermined type to treat a disease or disorder in the human or animal subject or to produce a change in the medium and 2) a receiver that receives the signal and optionally 3) a receiving and transmitting device. The assembly unit is configured, upon receiving the signal, to power the emitter thereby emitting the light interior the human or animal subject or interior the medium. The assembly (including for example components of computer system 1201 describe above) can be embedded in the human or animal subject and configured to perform a diagnostic function (such as a local measurement of temperature) and then emit such information to be processed. The transmission of such High Frequency signals can be optionally within the compliance and communication protocols and standards such as ISO 15693/ISO 18000-3 or optionally outside of such protocols. The information received from the embedded device that is remotely controlled is then processed through a computerized system (such as computer system 5 in FIG. 3) which provides a feedback loop as to the next step to be performed by the insertion device.

The reagents and chemicals useful for methods and systems of the invention may be packaged in kits to facilitate application of the invention. In one exemplary embodiment, a kit would comprise the insertion device(s) 3, at least one activatable agent capable of producing a predetermined cellular change, optionally at least one energy modulation agent capable of activating the at least one activatable agent when energized, optionally at least one plasmonics agent that can enhance the UV light (or visible light) from the insertion device(s) 3 such that the UV light (or visible light) from the insertion device(s) 3 activates the at least one activatable agent which produces a change in the medium when activated, and containers suitable for storing the various agents in stable form, and further comprising instructions for administering the at least one activatable agent and/or at least one energy modulation agent to a medium, and for applying an initiation energy from an initiation energy source to activate the insertion device(s) 3. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

Specific Insertion Device Configurations

The insertion device(s) 3 described above can employ one or more of the configurations described below.

In one embodiment of the invention, the insertion device(s) 3 are part of an intravenous ultraviolet implant inserted into blood supply vessel close to a diseased organ. US Pat. Appl. No. 2006/0183987 describes an intravenous ultraviolet implant within a human body having a plurality of ultra-violet frequency (UV) LED's attached radially in an inwardly facing manner to a rigid ring, an electrical power cord attached at one end to the UV-LED ring and at the other end to a power supply such as a battery, and a housing that encloses the power supply as well as other standard electronic components such as resistors and battery contacts. In the '987 application, the ring was surgically installed within a major vein so that blood passing through the vein can be irradiated with UV light frequencies.

Figure 5:
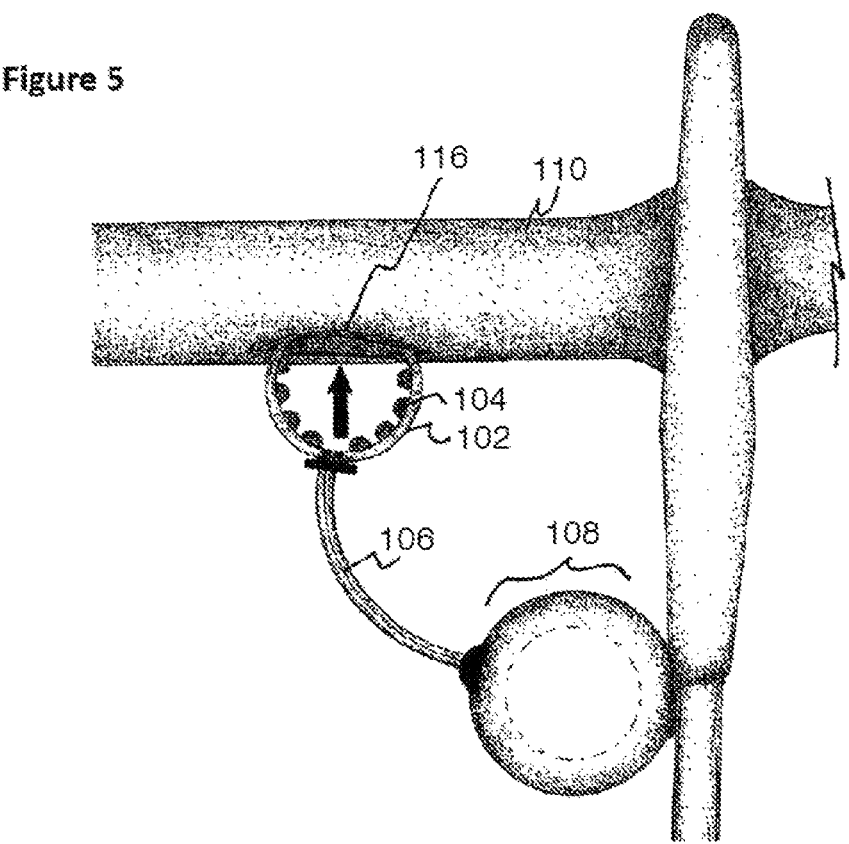
FIG. 5 is a schematic depiction of a ring-member insertion device.

FIG. 5 is a schematic depiction of a ring-member insertion device. In one embodiment of the invention, the ring member insertion device can be installed inside a major vein or artery 110 by way of a surgical slit 116 so that blood passing through can be irradiated with UV and/or visible light frequencies on reception of an initiation signal.

Similar to that in the'987 application, the insertion device(s) are disposed along an interior or exterior a ring member 102 and comprise a plurality of UV or visible LED's 104 radially attached to the inner surface of the ring member 102. A resilient tubular cord 106 can enclose a pair of electrically conducting wires that power the LED's 104. A housing 108 encloses components that control and power the LED's 104. After insertion in the vein or artery 110, the ring member 102 may be turned ninety degrees so that blood can flow through the ring member 102 and be radiated by the UV or visible LED's 104. Inside the housing 108 are a battery and control electronics to operate the UV or visible LED's 104. The control electronics can receive the initiation signal as discussed above. Here, in the present invention, housing 108 contains a supply of the activatable drugs, the energy modulation agents, and/or plasmonic agents. The energy modulation agents and/or plasmonic agents can serve to enhance the penetration of the UV or visible light throughout a portion of the artery or vein and if positioned adjacent a diseased organ can serve to enhance the penetration of the UV or visible light into the diseased organ.

In one embodiment of the invention, ring member 102 (or for example the insertion devices 3 shown in FIG. 2A) are attached onto the outside of the arteries (e.g., bronchial arteries) interior or in proximity to a diseased organ (e.g. the lungs). UV or visible light emitted from the ring member 102 without or without the assistance of energy modulation agents and/or plasmonic agents can penetrate the diseased cells of the organ and activate the above-noted photoactivatable drugs, administered separately or from the insertion device(s) 3.

Figure 6:
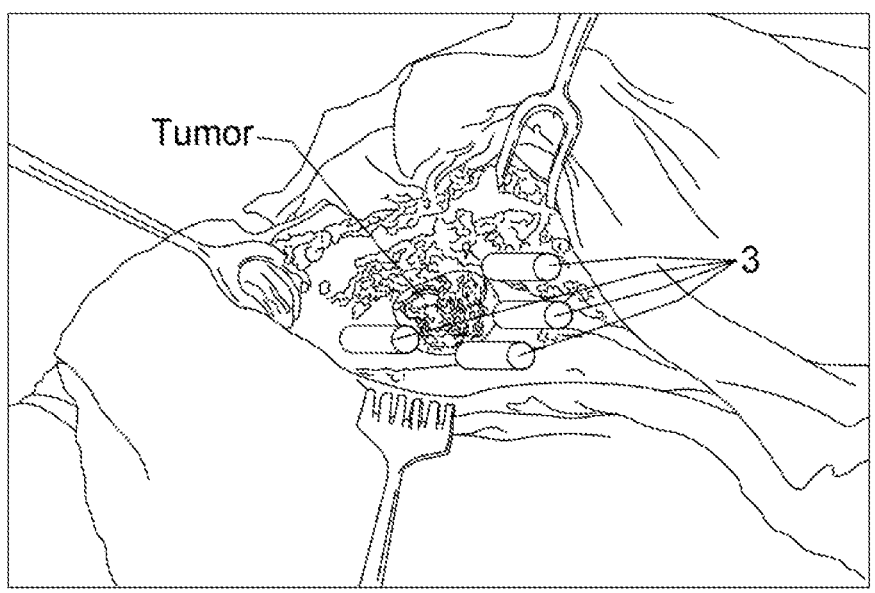
FIG. 6 is a schematic depiction showing the placement of insertion devices about a tumor on a lung.

In another embodiment of the invention, FIG. 6 shows the surgical placement of the insertion device(s) 3 around a lung tumor. The insertion devices (not shown to scale) would be attached to the surface of the tumor. (While illustrated here with full exposure of the lung cavity, the insertion devices could be positioned by a robotic device or an intra-cavity catheter.) Millimeter size devices or sheet or wire-tube configurations (discussed below) holding a plurality of the insertion devices would be positioned and secured to the surface of the tumor. In one embodiment of the invention, the insertion device(s) 3 would be adhered to the surface of the tumor with a substantially UV transparent or visible light transparent adhesive to promote better coupling of the light into the tumor. In one embodiment of the invention, plasmonics structures such as gold nanoparticles could be impressed into the tumor prior to securing the insertion device(s) 3. The gold nanoparticles serve to enhance the UV light intensity and thereby increase the probability of the photoactivatable drugs inside the cancerous mass being activated.

Once the insertion devices were secured, the patient could be sewn up. The initiation energy would then be used to control periodic UV and/or visible light exposures simultaneous with the presence of the photoactivatable drug.

Figure 7A:
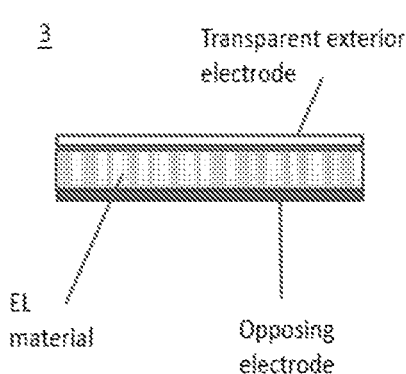
FIG. 7A is a schematic depiction of planar electroluminescent (EL) insertion device.
Figure 7B:
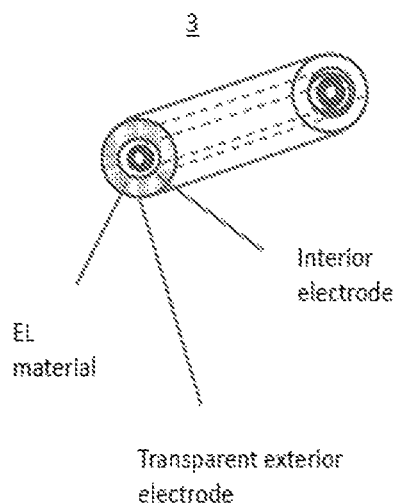
FIG. 7B is a schematic depiction of a coaxial electroluminescent (EL) insertion device.

FIG. 7A shows another insertion device configuration of the present invention. Specifically, FIG. 7A is a schematic depiction of planar electroluminescent (EL) insertion device In this configuration, electroluminescent devices are used as the source of the UV and/or visible light. Electroluminescent (EL) devices include a material (or materials) which emits light in response to the passage of an electric current or to a strong electric field. FIG. 7B shows still another insertion device configuration of the present invention. Specifically, FIG. 7B is a schematic depiction of coaxial electroluminescent (EL) insertion device.

U.S. Pat. No. 6,204,514 illustrates how ultraviolet light emitting devices can be fabricated. The techniques in the '514 patent are suitable in the present invention for preparation of UV light emitting insertion device components. The '514 patent describes for example that an EL element (or a laser luminescent element) capable of emitting ultraviolet rays with high wavelength purity includes a thin film made from one of a polymer and an oligomer in which the elements, selected from Si, Ge, Sn, and Pb, and directly bonded. The elements selected may be the same as or different from each other. The film is disposed between two electrodes. At least one of the electrodes is transparent. In one embodiment of the present invention the thin film polymer-based construction permits the insertion device(s) 3 of the present invention to be fabricated on a flexible template thereby providing a conformal luminescent sheet which can be "wrapped" in place at the diseased organ.

The '514 patent indicates that a thin film made from a polymer or an oligomer, can be formed by directly bonding elements selected from Si, Ge, Sn, and Pb (those elements may be the same as or different from each other) and used as an emission layer of an EL element or a laser luminescent element. As a polymer or an oligomer in which elements selected from Si, Ge, Sn, and Pb are directly bonded (those elements may be the same as or different from each other), chemical formula 1 may be used as follows:

polymer or oligomer in which elements selected from Si, Ge, Sn, and Pb are the same as each other, and the elements are directly bonded, or chemical formula 2 may be used as follows:

polymer or oligomer in which elements selected from Si, Ge, Sn, and Pb are different from each other, and the elements are directly bonded.

[Chemical formula 1]

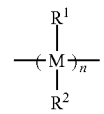

Here, M represents Si, Ge, Sn, or Pb, and $R^1$ and $R^2$ represent substituents of the aforementioned elements. Both of them may be the same as or different from each other. Alkyl group, allyl group, phenoxy group, alkoxyl group, alkylamino group, alkylthio group, alcoholic hydroxy group or the like may be selected as $R^1$ and $R^2$. However, they are not limited to the above-mentioned groups.

[Chemical formula 2]

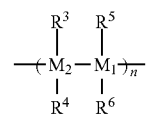

Here, $M_1$ and $M_2$ represent Si, Ge, Sn, or Pb, and $R^3$, $R^4$, $R^5$, and $R^6$ represent substituents of the aforementioned elements. Both of them may be the same as or different from each other. Alkyl group, allyl group, phenoxy group, alkoxyl group, alkylamino group, alkylthio group, alcoholic hydroxy group or the like may be selected as $R^1$ and $R^2$. However, they are not limited to the above-mentioned groups.

A polymer of any one of the four kinds of 14th group elements Si, Ge, Sn, and Pb basically has the same physical properties. So that it is possible to obtain an EL element and a laser luminescent element with an emission spectrum in the ultraviolet range from a polymer or an oligomer in which the above-mentioned elements are exchanged with each other. Since this kind of EL element has a narrow emission band, it is possible to produce EL elements and laser luminescent elements with different emission wave lengths by changing the kinds of 14th family elements or the sequence of elements.

In the '514 patent and in the present invention, the UV light emitting EL devices can be made using conventional methods such as spin coating, vacuum evaporation, optical CVD, thermal CVD, and MBE (molecular beam epitaxy) may be used to form an emission layer film. When an emission layer is formed directly on a base plate by the CVD method, it is advantageous to use a silane-treated surface.

In the '514 patent and in the present invention, with a polymer or an oligomer, which is used as an emission layer in the present invention, it is possible to control the emission wave length by changing the number of atoms of Si, Ge, Sn, and Pb, which form the main structure. Generally, as chain length of the polymer or oligomer becomes longer, the peak wave length shifts on the long wave length side.

In the '514 patent and in the present invention, emission of polysilane itself is used to provide an ultraviolet electroluminescent element. These materials of the '514 patent can be utilized in either the configurations of FIGS. 7A and 7B to produce either planar or of coaxial electroluminescent (EL) insertion devices 3.

Similarly, Brovelli et al in *Nature Communications*|3: 690|DOI: 10.1038/ncomms1683|www.nature.com/naturecommunications Received 3 May 2011 Accepted 12 Jan. 2012 Published 21 Feb. 2012, reported on the realization of fully inorganic ultraviolet light-emitting diodes emitting at 390 nm with a maximum external quantum efficiency of ~0.3%, based on $SnO_2$ nanoparticles embedded in $SiO_2$ thin films obtained from a solution-processed method. The techniques in the Brovelli et al are applicable to the present invention for fabrication of UV (or visible) light emitting EL devices for the insertion device(s) 3. Brovelli et al report on a composite planar system similar to that shown in FIG. 7A, including a p-silicon substrate and the semitransparent Au-capped titanium cathode (~10 nm Au; ~5 nm Ti). The choice of titanium as electrode assured a good electron injection into the conduction band of SnO2 NCs (FIG. 2e), which favors electric conduction and the resulting generation of excitons inside the NCs. Furthermore, titanium ensured good adhesion on the glassy active film, which results in remarkably robust LEDs resistive to mechanical damage.

These materials of the Brovelli et al article can be utilized in either the configurations of FIGS. 7A and 7B to produce either planar or of coaxial electroluminescent (EL) insertion devices 3.

Konenkamp et al in an article in Nano Lett. 2005 October; 5(10):2005-8, entitled "Ultraviolet electroluminescence from ZnO/polymer heterojunction light-emitting diodes" describe ultraviolet electroluminescence at 390 nm from diode structures consisting of electrodeposited ZnO nanorods sandwiched between a transparent $SnO_2$ film and a p-type conducting polymer. The nanorods were embedded in an insulating polystyrene layer. ZnO deposition occurs at 90° C. and produces vertically oriented nanorods with very high uniformity over areas of approximately 20 $cm^2$. Electron diffraction shows the nanorods to be single crystalline wurtzite ZnO. As-grown films show a broad electroluminescence band over the visible spectrum. Annealing at moderate temperatures (T=300° C.) increased the emission and strongly raises the excitonic contribution. Optimally processed films in the Konenkamp et al article showed a narrow ultraviolet electroluminescence line at approximately 390 nm. These materials of the Konenkamp et al article can be utilized in either the configurations of FIGS. 7A and 7B to produce either planar or of coaxial electroluminescent (EL) insertion devices 3. The low temperature deposited 90° C. ZnO would in the present invention be especially well suited for deposition on low temperature flexible polymeric substrates, thereby providing a flexible, conformal sheet of EL devices to apply to a tumor.

U.S. Pat. No. 8,786,188 describes another configuration which can be used in the present invention for remote communication and power supply to the insertion devices 3. The '188 patent describes a wireless electroluminescent device having a top (or first) electrode layer and a bottom (or second) electrode layer, an electroluminescent layer, and an interconnection. The interconnection connects the top and the bottom electrode layers, with the two electrode layers structured as windings; and the electroluminescent layer located between the two electrode layers.

The '188 patent describes a mode of operation which would be preferred in the insertion devices 3 of the present invention. That is an AC voltage is induced into the electrode layers by an electromagnetic field. The induced voltage is applied to the electroluminescent layer being located between the two electrode layers. Thus, the first and the second electrode layer are adapted for applying a voltage on the electroluminescent layer. Because the electroluminescent device acts as a diode and blocks the current in reverse direction, only during one of the half waves a current flows. While for the purposes of the '188 patent, the AC frequency has to be high enough to avoid flickering, e.g. larger than 100 Hz, here in the present invention the "flickering" merely provides a high frequency duty cycle for the UV or visible emission. When the AC frequency is in the kHz, MHz or even GHz region, the spatial length of the windings will control the power coupling based in part on the resonance frequencies of the windings being used.

Figure 8:
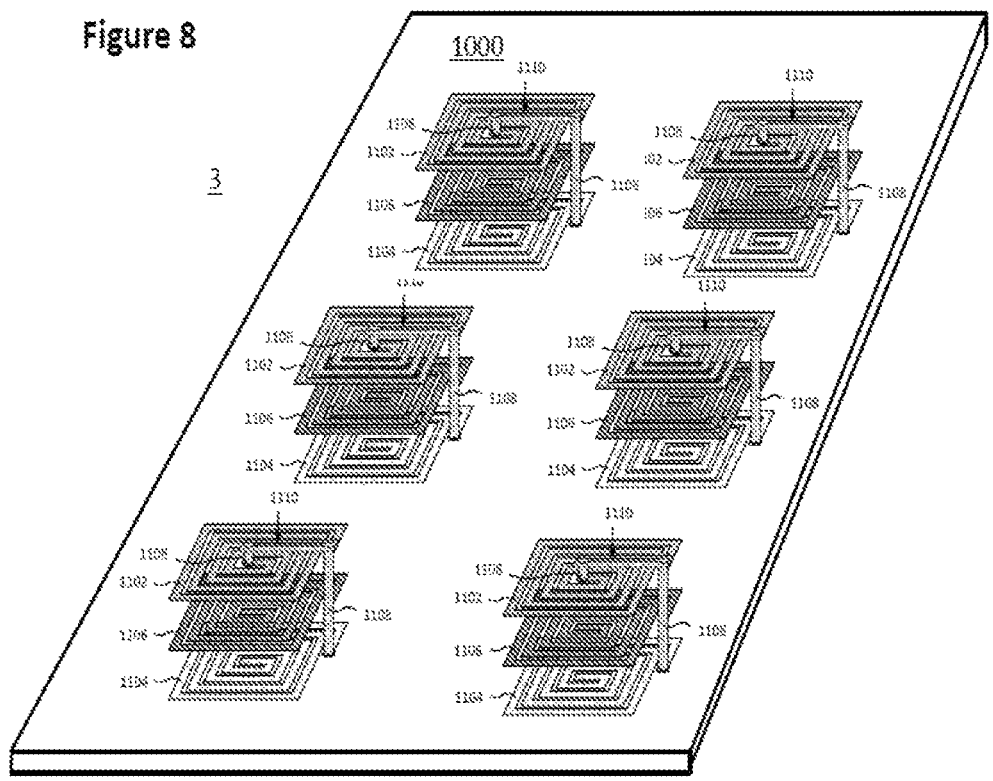
FIG. 8 is a schematic depiction of a wireless EL insertion device 3 according to the invention.

FIG. 8 is a schematic depiction of a wireless EL insertion device 3 according to the invention. Similar to that m the '188 patent, the electroluminescent devices are mounted on a common substrate 1000 which may be a flexible or rigid material. Each EL device comprises a top electrode 1102, a bottom electrode 1104, an electroluminescent layer 1106, an interconnection 1108, and an insulation layer 1110.

The electroluminescent layer 1106, the top electrode 1102 and the bottom electrode 1104 are structured as clockwise windings. As an alternative, anti-clockwise windings can also be used. The electroluminescent layer 1106 is located between the top electrode 1102 and the bottom electrode 1104. The interconnection 1108 connects the top electrode 1102 with the bottom electrode 1104. The origin of the windings of top electrode 1102 is connected with the interconnection 1108 to the end of the peripheral winding of bottom electrode 1104. The insulation layer 1110 insulates other parts of the top electrode 1102 from the interconnection 1108 for avoiding a short circuit. The insulation layer may be extended to form an encapsulation layer isolating and passivating these components and materials from the medium where the insertion device(s) are to be disposed.

In operation, an AC voltage is induced into the windings of the top electrode 1102 and the bottom electrode 1104. Because the end of the peripheral winding of the bottom electrode 1104 is connected with the origin of the windings of the top electrode 1108, a short circuit is established between these two points. Thus, the applied voltage at these points is zero volts. Depending on the direction of the electromagnetic field the voltage in the windings increases or decreases from the origin of the windings to the end of the peripheral winding.

If, for example, the voltage decreases from the origin of the windings to the end of the peripheral winding, the induced voltage in the top electrode 1102 decreases from 0 volts in the origin of the windings to the maximum negative value on the end of the peripheral winding. The maximum value depends on the power of the electromagnetic field. The voltage in the bottom electrode 1104 increases from 0 volts on the end of the peripheral winding up to the maximum value in the origin of the windings. Thus, there is a constant voltage between the top electrode 1102 and the bottom electrode 1104, the maximum voltage induced by the electromagnetic field.

Because a homogeneous voltage is applied between the two electrodes, the electroluminescent layer homogeneously emits light. A short circuit is avoided by the winded structure of the electroluminescent layer. To avoid shortcuts the electroluminescent layer 106 is preferably a good conductor in the direction from one electrode to the other electrode, and a bad conductor in the perpendicular direction. This is achieved by the structured electroluminescent layer 1106 in FIG. 1. Alternatively a non-structured contiguous electroluminescent layer can also be applied without risks of shorts, if the thickness of the electroluminescent layer is significantly smaller than the distance between neighbored windings of the electrodes. A typical thickness of the electroluminescent layer is 100 nm. The distance between neighbored windings can be adjusted to be at least 1 mm. For electroluminescent layers with a homogeneous conductivity, the electrical path from one electrode to the opposite electrode can be about 10000 times shorter than the electrical path from a winding to its neighbored winding of one electrode.

U.S. Pat. No. 8,317,561 similarly described light emitting diode materials and configurations operating in response to frequencies from between about 30 and 500 kHz, and between about 10 and 15 MHz. The materials and configurations are suitable for the insertion device(s) of the present invention. Indeed, as described in the '561 patent and applicable to the present invention, an alternating electromagnetic field usually induces a voltage in a coil and/or an antenna, (e.g., the top and bottom electrodes of FIG. 8) which generates a voltage/current, as described in the '561 patent and applicable to the present invention, a micro-coil can be used in the present invention in addition to or as the top and bottom electrodes of FIG. 8. The micro-coils can have, for example, in cross section, a height of less than or equal to 2 mm, such as less than or equal to 1 mm and/or a width of less than or equal to 5 mm, such as less than or equal to 3 mm. The length of a micro-coil equals between about 20 mm and 50 mm in some embodiments; for example, in one embodiment, the micro-coil length equals 30 mm. The micro-coil can include a ferrite core.

In one embodiment of the present invention, a device (for example, a storage battery) can be included (e.g., on substrate 1000 or inside housings 24 or 108) that stores or accumulates the energy drawn by the receiver device from the alternating electromagnetic field over a longer time span—that is for a longer duration than one or a few periods of the alternating electromagnetic field The power accumulated over time can then be used "on demand" to power the UV or visible light emitting insertion device(s) 3.

Figure 9:
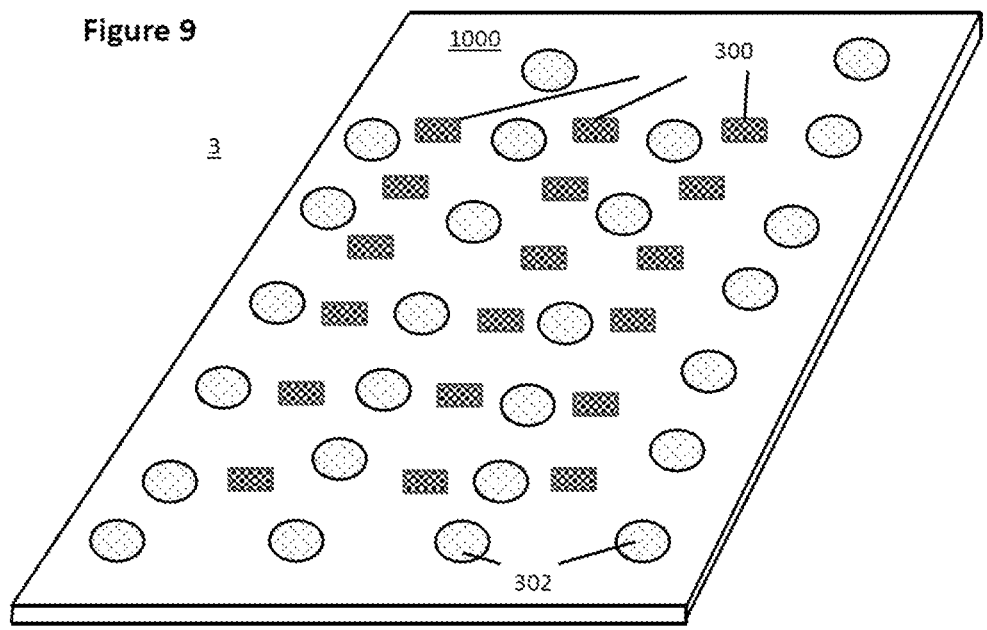
FIG. 9 is a schematic depiction of a flexible wireless UV or visible light emitting insertion device according to the invention.

FIG. 9 is a schematic depiction of a flexible wireless UV or visible light emitting insertion device 3 according to the invention. In one embodiment of the present invention, substrate 1000 could be a porous template containing the plurality of wirelessly powered UV or visible light emitting LEDs or EL devices 300. The devices 300 would in one embodiment contain the light emitters and the micro-coils described above. The devices 300 would in another embodiment contain the light emitters and use strip antennas on the substrate 1000 and a battery to power the devices. As shown in FIG. 9, the substrate 1000 has an optional number of holes 302 adding to the flexibility although inclusion of any of the holes is not required.

By having a porous template (i.e. a substrate with through-holes) small LED chips could be picked and placed robotically onto the porous membrane (or for that matter onto substrate 1000) and solder bump bonded to wire traces on the membrane. The wire traces would serve the antennas or micro-coils for the power coupling. With this template, the holes in the template would permit a medium to be treated (e.g., blood or polymers to be cured or a medium to be sterilized) to flow in between. This template with or without the pores made of a flexible material could be inserted by way of a catheter having substrate 1000 or the porous template rolled-up for placement inside or against a tumor site.

In one embodiment of the invention, the UV or visible light emitting LEDs or EL devices 300 can be made of the materials and constructions described in U.S. Pat. No. 7,355,284. In general, the '284 patent describes semiconductor light emitting devices including a substrate having a face, a flexible film that includes therein an optical element, on the face, and a semiconductor light emitting element between the substrate and the flexible film and configured to emit light through the optical element. The face can include a cavity therein, and the semiconductor light emitting element may be in the cavity. The flexible film extends onto the face beyond the cavity, and the optical element overlies the cavity.

As in the '284 patent and suitable for the present invention, some embodiments may be configured to incorporate phosphor into the semiconductor light emitting device. In some embodiments, phosphor is provided on the flexible film between the lens and the semiconductor light emitting element. In other embodiments, the lens includes a concave inner surface adjacent the semiconductor light emitting element, and the phosphor includes a conformal phosphor layer on the concave inner surface. In yet other embodiments, the optical element includes a lens that overlies the cavity and protrudes away from the cavity, the flexible film further includes a protruding element between the lens and the light emitting element that protrudes towards the cavity, and a conformal phosphor coating is provided on the protruding element. Combinations and subcombinations of these and/or other configurations of phosphor also may be provided. Moreover, an optical coupling media may be provided between the phosphor and the semiconductor light emitting element in any of these embodiments. In one embodiment of the present invention, the insertion device(s) 3 can include an optical coupling media may be provided between the semiconductor light emitting element and the diseased organ. The optical coupling media can be a fluid which has a relatively high visible or ultraviolet transmission as compared to blood. In one example, a saline solution can function as an optical coupling media.

As in the '284 patent and suitable for the present invention, the light emitting elements of the insertion device(s) 3 may be gallium nitride-based LEDs or lasers fabricated on a silicon carbide substrate such as those devices manufactured and sold by Cree, Inc. of Durham, N.C. Other suitable LEDs and/or lasers are described in published U.S. Patent Publication No. US 2003/0006418 A1 entitled Group III Nitride Based Light Emitting Diode Structures With a Quantum Well and Superlattice, Group III Nitride Based Quantum Well Structures and Group III Nitride Based Superlattice Structures, published Jan. 9, 2003, as well as published U.S. Patent Publication No. US 2002/0123164 A1 entitled Light Emitting Diodes Including Modifications for Light Extraction and Manufacturing Methods Therefor. Furthermore, phosphor coated LEDs, such as those described in U.S. application Ser. No. 10/659,241, entitled Phosphor-Coated Light Emitting Diodes Including Tapered Sidewalls and Fabrication Methods Therefor, filed Sep. 9, 2003, may also be suitable for use in embodiments of the present invention for the insertion device(s) 3. The LEDs may be configured to operate such that light emission occurs through the substrate. In such embodiments, the substrate may be patterned so as to enhance light output of the light emitting devices as is described, for example, in the above-cited U.S. Patent Publication No. US 2002/0123164 A1.

In another embodiment of the invention, the UV or visible light emitting LEDs or EL devices 300 can be made of the materials and constructions described in U.S. Pat. Appl. Publ. No. 2008/0096365. As in the '365 application and suitable for the present invention, the insertion device(s) 3 of the present invention can be fabricated from semiconductor devices at the wafer level. Wafer-level bonding using an electrically conducting bond medium can be used to achieve void-free permanent wafer level bonding. The bond medium can be introduced to the pre-bonded wafers by deposition or as a preform.

The papers, articles, patents, and patent applications discussed herein are each incorporated herein by reference in their entirety.

Passive and Active Insertion Devices

Remote control of the internal light (e.g., UV or visible) generating devices, according to various embodiments of the invention, can be accomplished by remote control of passive devices (i.e., devices that do not necessarily contain light emitting electronics) or active devices (i.e., devices that do contain light emitting electronics). For the passive devices, in one embodiment, the passive devices do not contain a chemical agent but works co-incubated with bio-therapeutic agent such as a photoactivatable drug or catalyst or co-incubated with other photoactivatable substances such as photoinitiators. For the passive devices, in one embodiment, the passive devices do contain a chemical agent which, upon release into the subject or medium to be treated, is then activated by light emitted from the passive device typically, but not necessarily, by some form of fluorescence or luminescence, as described in a number of the related cases incorporated by reference as noted above. For the passive devices, in one embodiment, the passive devices do not contain a chemical agent, but are able to treat a disease or disorder via a photobiomodulation pathway, as described in a number of the related cases incorporated by reference as noted above.

For the active devices, in one embodiment, the active devices do not contain a chemical agent but works co-incubated with bio-therapeutic agent such as a photoactivatable drug or catalyst or co-incubated with other photoactivatable substances such as photoinitiators. For the active devices, in one embodiment, the active devices do contain a chemical agent which, upon release into the subject or medium to be treated, is then activated by light emitted from the active device(s). For the active devices, in one embodiment, the active devices do not contain a chemical agent, but are able to treat a disease or disorder via the photobiomodulation pathway. For the active devices, in one embodiment, the active devices can have an on-board source of energy (e.g., a battery). For the active devices, in one embodiment, the active devices can rely on an external signal to charge the device and/or to provide instructions for how and when the active device functions. For the active devices, in one embodiment, the active devices can be programmed prior to insertion into the subject or medium to be treated. For the active devices, in one embodiment, the active devices can receive instructions (programming) once inside the subject or medium to be treated.

Figure 10:
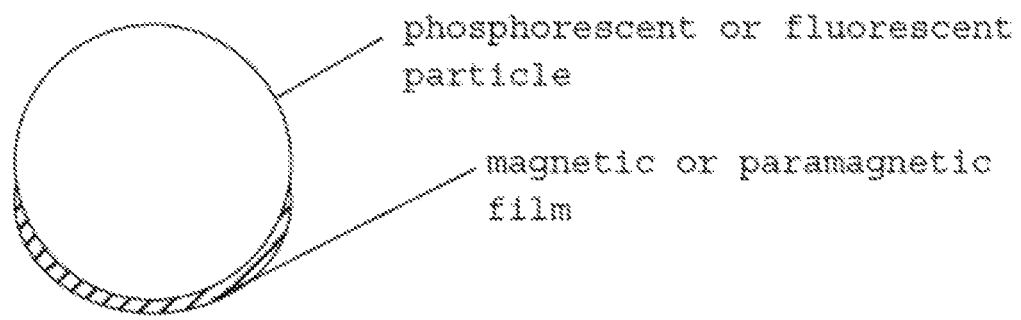
FIG. 10 is a schematic depicting a representative phosphorescent or fluorescent particle having a magnetic or paramagnetic component.

In one embodiment, passive devices are capable of remotely being oriented using a magnetic field. FIG. 10 is a schematic depicting a representative phosphorescent or fluorescent particle having a magnetic or paramagnetic component and that is capable of being activated using x-ray energy and/or an electron-beam. The magnetic or paramagnetic component includes, in one embodiment, a magnetic or paramagnetic film (or coating) partially covering the surface of the phosphorescent or fluorescent particle, and therefore partially covering an emission surface thereof. When the magnetic or paramagnetic film coated particle is exposed to a magnetic field, the coated particles will align in a common direction. The presence of the coating not only assists in alignment but also in directing light emission in a preferential direction by reflection or by obstruction. The reflection of the light occurs by at the internal surface between the magnetic or paramagnetic film and the phosphorescent or fluorescent particle. The reflective properties can be enhanced if the particle is coated with a metallic coating such as Gold or Silver prior to depositing the magnetic material. The obstruction of the light occurs when the thickness of the film is such that the transmission coefficient of the magnetic film attenuates the emitted light emanating from the phosphorous material.

Suitable ferromagnetic layers for this invention can be grown in one embodiment of the invention in an atomic layer deposition (ALD) system for production of manganites such as ($La_{0.7}Sr_{0.3}MnO_3$). Other paramagnetic and magnetic thin films (and ALD methods) are described and referenced in the Proceedings of the Workshop on Smoothing and Characterization of Magnetic Films. Vol. 112 (2007) ACTA PHYSICA POLONICA A No. 6, the entire contents of which are incorporated herein by reference.

In one embodiment of the invention, manufacturing considerations for production of the magnetically orientable phosphorous particles would follow for example the method described below, although the following description is not the only method to produce phosphor particles with a magnetic film attached thereon. In this manufacturable method, a slurry of phosphors is made by mixing a given mass of phosphors with a volume of solvent at for example a ratio of 1 gm of phosphor to 10 mL of solvent (such as Acetone).

The phosphor slurry is spun onto a meshed disk (e.g., like a sieve). The average particle size would be suitably matched the size of the aperture. A slight vacuum is applied from one side of the mesh during the spinning process to force the phosphors through the various apertures. The elastic forces of the solvent increases the binding of the phosphorous particles to the mesh. Once the particles are secured in place, the mesh is dried to remove the solvent.

Figure 11:
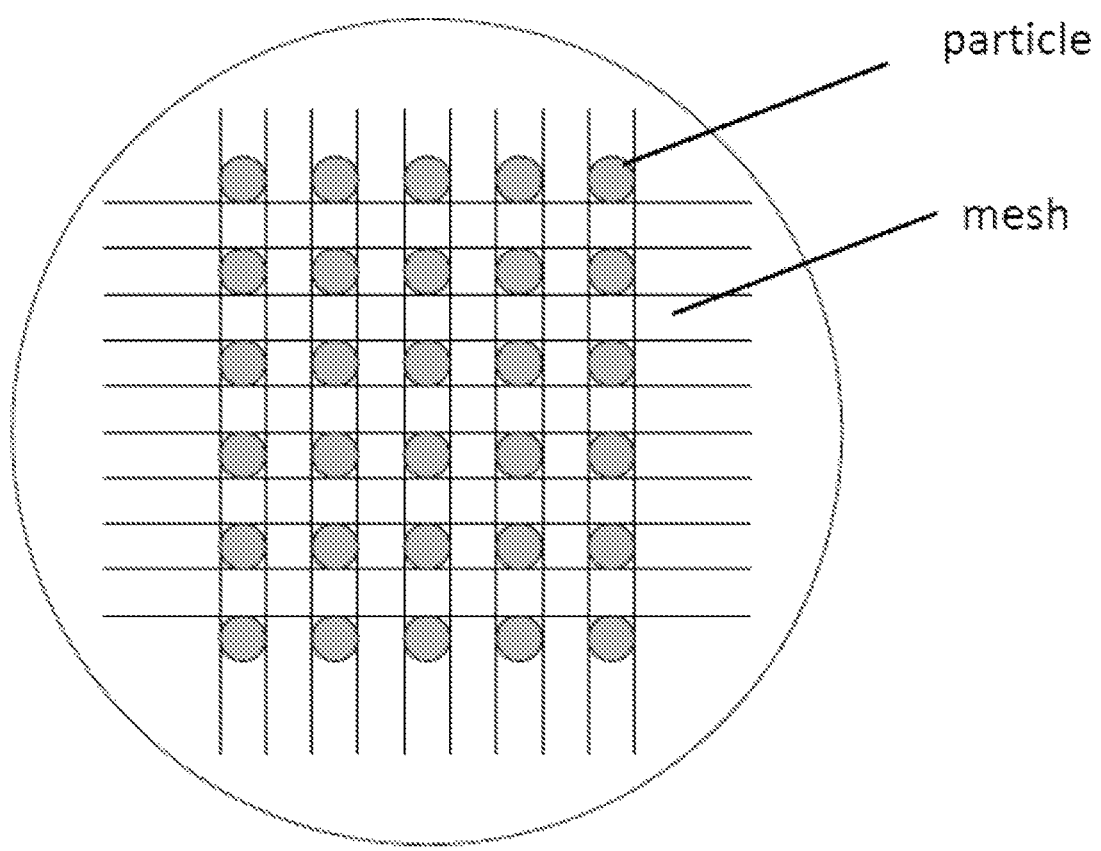
FIG. 11 is a schematic depicting particles secured in place in openings in a mesh.

FIG. 11 is a schematic depicting particles secured in place in openings in a mesh.

The mesh is then transferred to a metal vapor deposition system for deposition of a magnetic coating on the exposed top surface of the phosphor particles. In one embodiment, the above-noted atomic layer deposition (ALD) process could be used to deposit the magnetic coating on one side of the mesh and hence on one side of the embedded particles. In one embodiment, $La_{0.7}Sr_{0.3}MnO_3$ is the magnetic material deposited.

Once the deposition is performed, the mesh disk is transferred to a station where positive pressure is applied from the back side of the mesh to force the particles out of the mesh and into a container. Alternatively, an electromagnet can be used to pick up the partially coated particles. In this case the binding force of the magnetic field has to overcome the retaining force between the mesh and the particles. In either case (with or without a magnetic field, a positive pressure can be applied to remove the particles) The phosphorescent, fluorescent, or otherwise luminescent particles are therefore partially coated with a magnetic coating. This magnetic coating acts also as a light reflector reflecting emissions of the phosphor particles in a unidirectional manner. If the particles are suspended into a solution then gain a degree of freedom and can be made to orient and to reorient under the influence of an externally applied magnetic field.

Figure 12A:
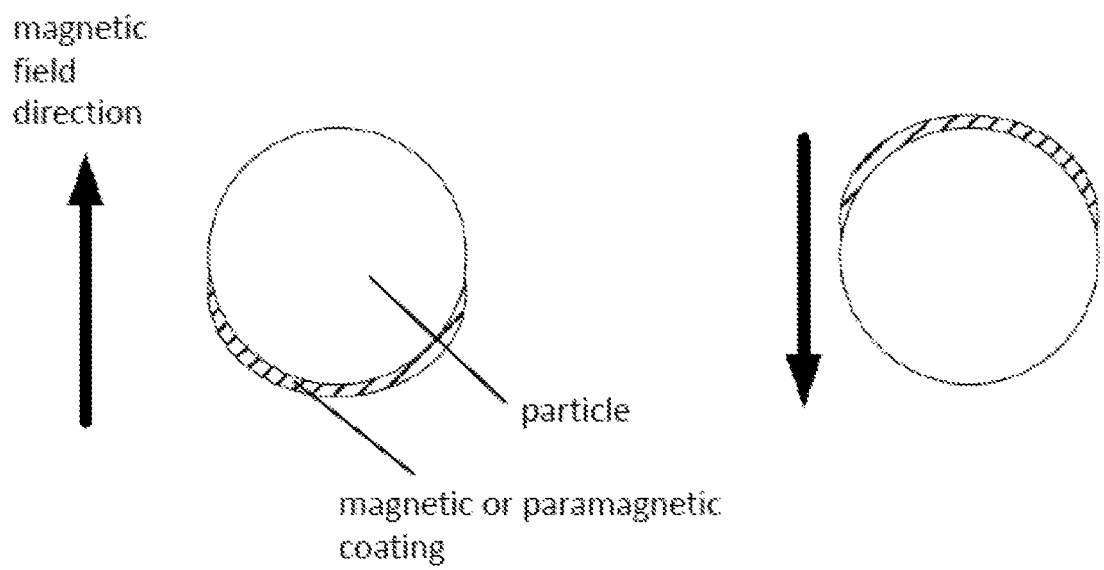
FIG. 12A is a schematic depicting a representative phosphorous or fluorescent particle aligned under the influence of a magnetic field.

FIG. 12A is a schematic depicting a representative phosphorous or fluorescent particle aligned under the influence of a magnetic field, showing the ability to orient the particles in a preferred direction and thereby orient the direction of the light emission.

Figure 12B:
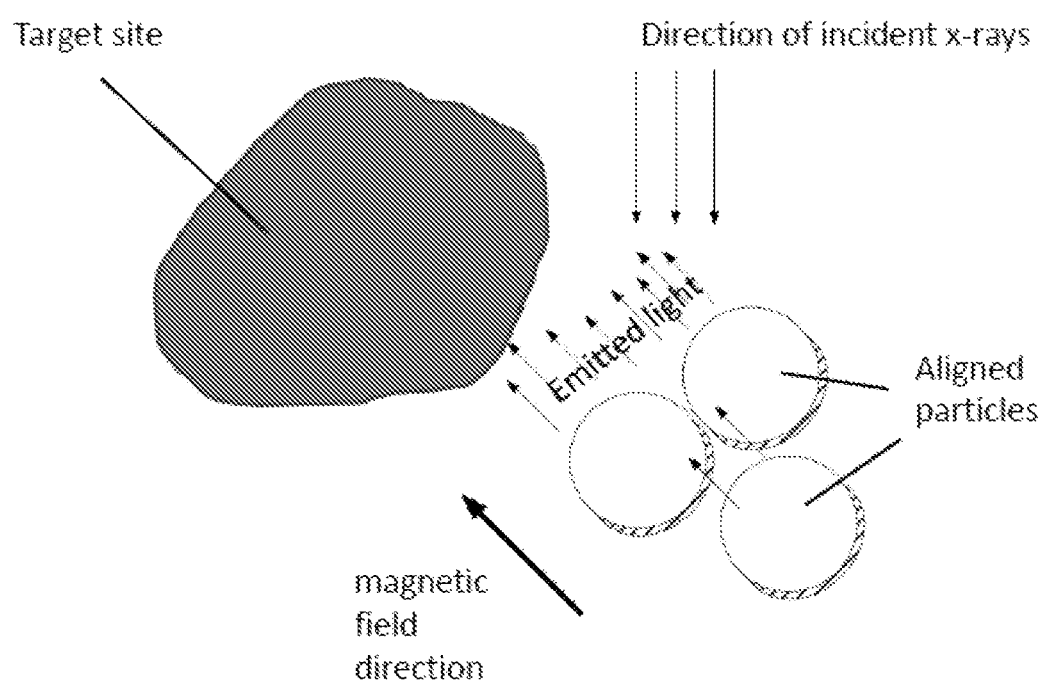
FIG. 12B is a schematic depicting a representation of multiple phosphorous or fluorescent particles aligned under the influence of a magnetic field where the net light emissions re-directed (preferentially) toward a target site.

In particular, FIG. 12B shows a representation of multiple phosphorous or fluorescent particle aligned under the influence of a magnetic field where the net light emissions (induced by incident KV, MV X-Ray beams are directed (preferentially) toward a target site, for example a diseased area, and thereby bypassing normal tissue. In one embodiment, a particle beam or a photon beam can be used instead of the x-rays.

Normally, when a phosphorous particle is exposed to an excitation energy leading to its excitation and subsequently its emission, the emitted light emanates from the numerous color centers and the emission is uniform (isotropic emission).

Figure 13:
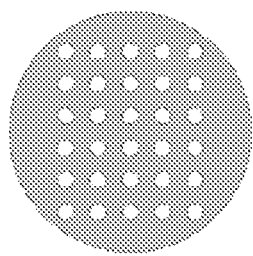
FIG. 13 is a process diagram showing various steps according to one embodiment for making the inter-layered phosphorous or fluorescent composite.
Figure 13:
Figure 13:
Figure 13:
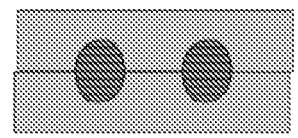
Figure 13:
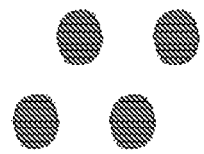

One method for achieving non-isotropic light emissions would be, according to one embodiment of the invention, to have a particle constructed by inter-layering metallic thin layers with phosphorescent or fluorescent layers. FIG. 13 is a process diagram showing various steps according to one embodiment for making the inter-layered phosphorous or fluorescent composite. First, a wafer (such as an intrinsic silicon wafer) is etched to form a set of cavities (e.g., small hemispheres etched into the silicon wafer), as shown in the top view in FIG. 13.

An illustration of the cross-section of the hemispheres etched into the silicon wafer is shown in step a-1. In step a-2, the silicon wafer is placed inside a deposition system where an interlayering is formed by a sequential deposition of a metal (e.g., Ag or Au) thin film (and/or a magnetic or paramagnetic film) followed by a phosphor thin film (e.g., $YTaO_4$) or other phosphorescent or fluorescent film.

The interlayering of the thin films metals (Ag or Au in this case) and thin phosphor films ($YTaO_4$ in this case) create hemispheres. In one embodiment, the thickness of each layer can vary from 100 nm to 800 nm, or from 10 to 2000 nm, or from 200 to 800 nm, or from 400 to 500 nm with intermediate and extended layer thicknesses achievable through timing of the layer deposition sequences. In other embodiments, a separation distance between layers in the layered assemblies noted above can range from 10 nm to 1000 nm, or between 100 nm and 700 nm, or between 200 nm and 500 nm, or between 300 nm and 400 nm. In still other embodiments, a separation distance between layers in the layered assemblies noted above can range from 1 µm to 1000 µm, or between 10 µm and 100 µm, or between 100 µm and 500 µm, or between 300 µm and 400 µm.

As shown in step a-3, once two wafers that have been used to create hemispheres, the hemispheres of each wafer are butted and collapsed together under heat and pressure to fuse the thin meal layers together and form spheres of the interlayered structures out of the two hemispheres.

The particles as seen in step a-4 are removed from the wafer by etching of the silicon.

In one embodiment of the invention, these particles formed through sequential layering of thin film metals (Ag in this case) and thin film phosphors ($YTaO_4$ in this case) have anisotropic light emission under the influence of an excitation energy such as X-Ray.

In one embodiment of the invention, there are specially occurring photonic crystals and "black" phosphors that have non-isotropic emissions which can be utilized to produce anisotropic emissions.

One example of such materials capable of emitting more energy along certain planes but not others. include:

$Sr_2CeO_4$ where the crystallographic structure is orthorhombic and the phosphor has linear chains of edge sharing $CeO_6$.

Other examples of such phosphors include:

$(Y_{0.82}Al_{0.07}La_{0.06})VO_4:Eu_{0.05}$, $(Y_{0.5}Gd_{0.5})_{2.97}(Al_{0.5}Ga_{0.5})_5O_{12}:Ce_{0.03}$.

The methods of building and the specific chemistries to be utilized are described in U.S. Pat. No. 6,013,199, the entire contents of which are incorporate herein by reference.

Figure 14:
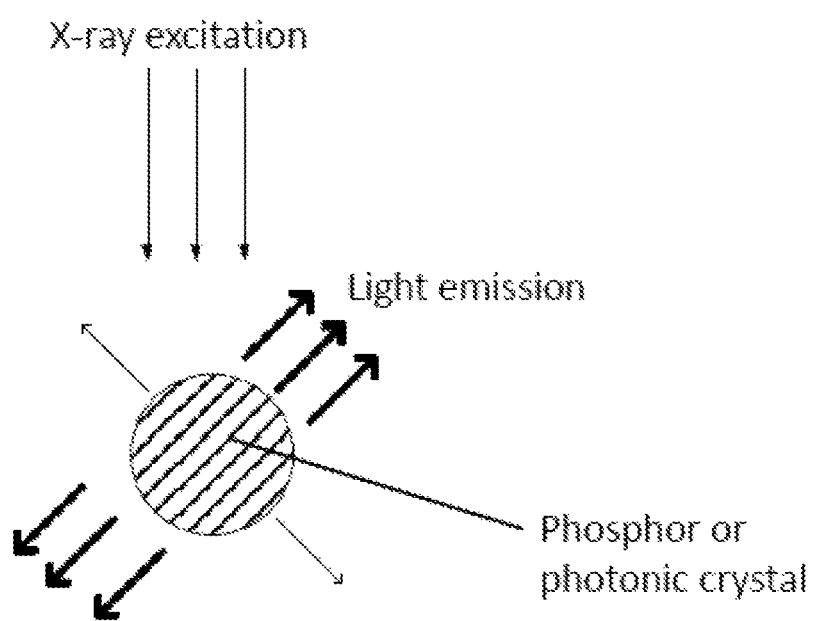
FIG. 14 is a schematic depicting x-ray excitation and a preferential light emission from the phosphor or photonic crystal along certain crystallographic planes.

In one embodiment of the invention, these phosphors would be coated with a magnetic or paramagnetic material (as described above) and oriented by way of a magnetic field (as described above). X-Ray energy excitation of these phosphor or photonic crystals would result in light emission preferentially along different crystallographic planes in these materials. FIG. 14 is a schematic depicting x-ray excitation and a preferential light emission from the phosphor or photonic crystal along certain crystallographic planes.

Figure 15:
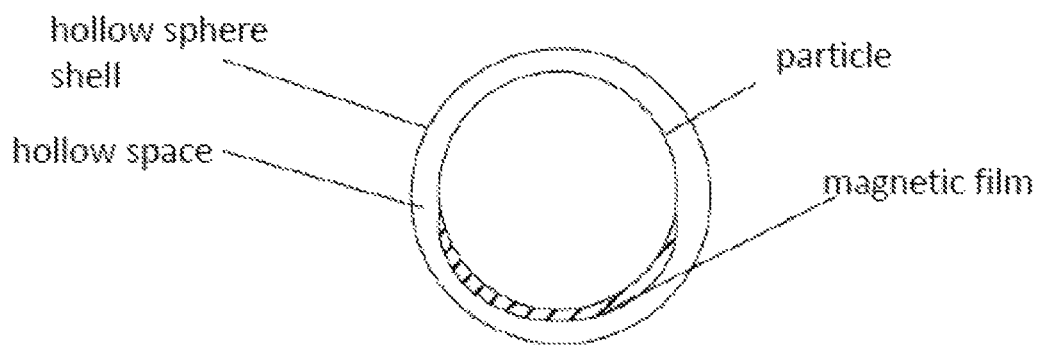
FIG. 15 is a schematic depiction of a free-floating particle inside a hard shell core of a hollow sphere.

In one embodiment, the phosphorescent or fluorescent particles are "free-floating" particles inside hard shell cores of hollow spheres. FIG. 15 is a schematic depiction of a free-floating particle inside a hard shell core of a hollow sphere. In one aspect of this embodiment, a polycrystalline or single crystalline particles is encapsulated inside a fluidic media in the hollow space, provided by the encapsulating hard shell core. In one aspect of this embodiment, the fluidic media can be a bio-therapeutic suspension (e.g., a photoactivatable drug or other therapeutic substance). A breaking of the shell would release the bio-therapeutic suspension into the subject to be treated.

In one embodiment of the invention, manufacturing considerations for production of the free-floating particle construction would follow for example the method described below, although the following description is not the only method to produce this construction.

Figure 16:
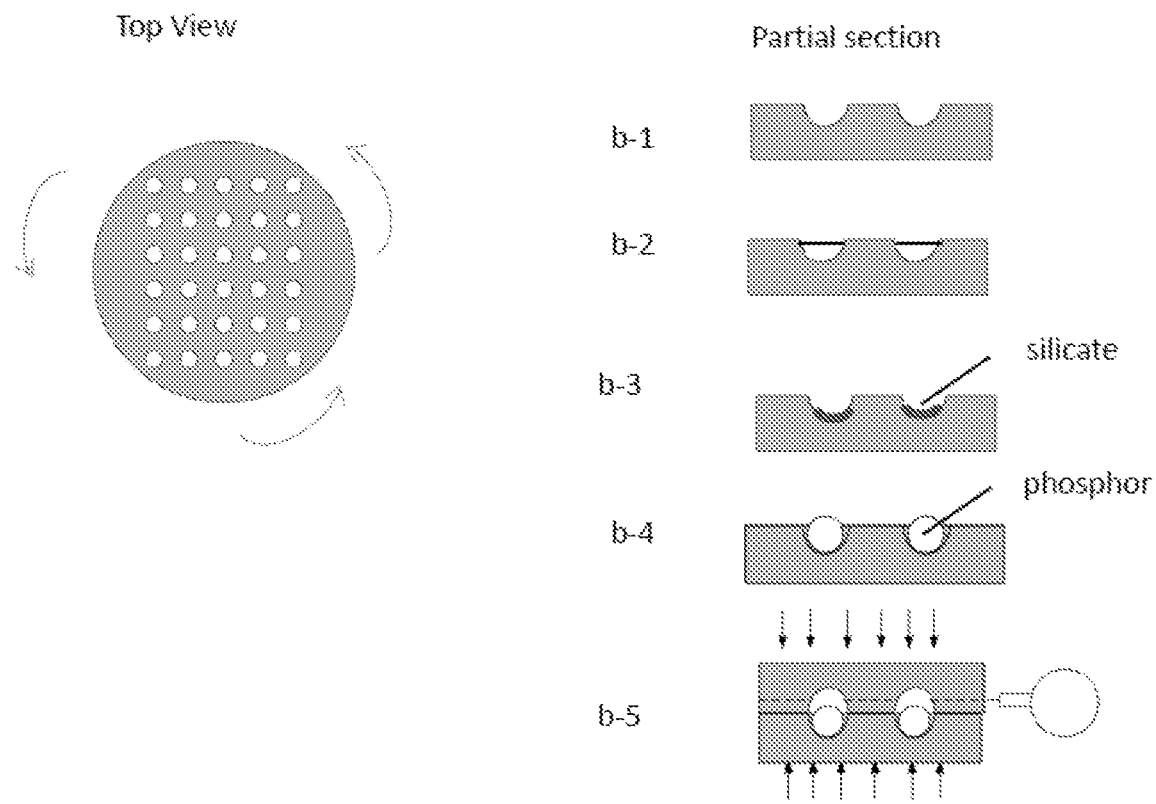
FIG. 16 is a process diagram showing various steps according to one embodiment for making the free-floating particle construction.

FIG. 16 is a process diagram showing various steps according to one embodiment for making the free-floating particle construction. In step b-1, an intrinsic silicon wafer with hollow up hemispheres is prepared. (The hemispheres in this case, can be in the range of 5 to 10 microns for the sake of illustration.) A solution is prepared containing a silicate chemistry (with a proportion within the range of $6SiO_2:1Al_2O_3:2NaO_2$). The silicate solution is added to the wafer surface while it is spinning at a rate for example of 250 rpm and fills the hemispheres, as shown in step b-2. An IR lamp is used to dry and vitrify the silicate chemistry span on the wafer, as shown in step b-3. Two wafers are prepared in the same fashion. The bottom wafer is designed to host the phosphors powders. The top wafer is treated using photoresist techniques to etch fluidic channels. (A slurry containing magnetic powders or a dry powder spray of magnetic powders could be used to provide for a "strip" of magnetic material.)

A slurry containing phosphors is added to the wafer also while spinning for example at around 100 rpm. The wafer is dried and the phosphors particles become lodged into the hemispheres. Step b-4 shows a depiction of this completed step.

The second wafer (top wafer) also containing a silicate coating and containing microfluidic channels is positioned on top of the first wafer containing the phosphors. The two wafers are pressed and heated until the silicate coatings are fused to form a sphere (from the 2 initial hemispheres contained in each of the respective top and bottom wafers).

Once the composited two wafers are fused the biotherapeutic agent is added through the microfluidic channels (step b-5). A pressure is added until the silicate capsules are filled with the bio-therapeutic agent. The top wafer is released from the bottom wafer. The glass coating is released from the top wafer by applying a rapid heat spike to the wafer to force a thermal expansion mismatch. The glass capsules are now formed and partially filled with the phosphors particles and the bio therapeutic agent. The free volume left between the inner volume of the silicate sphere and the phosphor particle is partially filled (e.g., at about 65% fill). The small aperture on top of the sphere (where the microchannel existed) is closed using a laser. The bottom wafer is exposed to a rapid thermal heat using lamps to release all the glass capsules from the wafer. The spheres containing the phosphors and the bio-therapeutic are hence formed.

These cylindrical phosphorous materials depicted in b-4 can be made for example by compacting a phosphorous powder and then sintering the powder to form the desired shape. An organic binder can be used to give the powder green strength and an extrusion process can be used to heat and burn the binder at 700° C. followed by sintering at elevated temperatures. The sintering temperatures can be around 1500° C. The sintering temperatures can be lowered by adding a small silicate chemistry such as $3SiO_2:1Na_2O$ to lower the temperature at which the particles can be necked together.

In one embodiment of the invention, particles such as for example an amorphous, polycrystalline, or single crystalline particle with a magnetic strip can be encapsulated with a fluidic media inside a hard shell cover (where the fluidic media could be a bio-therapeutic suspension) and where the hard shell can be made breakable under certain X-Ray energies. Schematically, the structural elements are the same as in FIG. 15 but the hard shell is made of materials susceptible to X-ray damage and loss of structural integrity.

In this embodiment, the hard shell capsule containing a fluidic bio-therapeutic agent which can be made to break (or lose structural integrity) under the influence of X-Ray energy exposure is a glass modified for example to contain PbO. Bio therapeutic agent in powder forms can also be used. The manufacturing method of adding such is however different than for fluidic bio therapeutic agents. Pb can be incorporated as a network former in the glass chemistry at a rate of 0.5% molar percent compared to Silica. Upon X-Ray exposure the Si—O—Pb bridge is broken. If sufficient amount of these lead containing silicate bridges are broken then the glass loses its structural integrity. Other heavy metals can be added instead of or as a supplement to the Pb, such as network formers of Cu and Ag. Regardless of the heavy metal used, the same phenomenon of breakable bonds under X-Ray works to produce a glass capsule that is breakable under X-Ray.

In one embodiment, multiple hard shell capsules can contain the same or different bio-therapeutic agents. Each capsule can be made of a shell having a different thickness that will break under different X-Ray beam or delivered dose and therefore a staged and controllable drug delivery system is devised.

Figure 17:
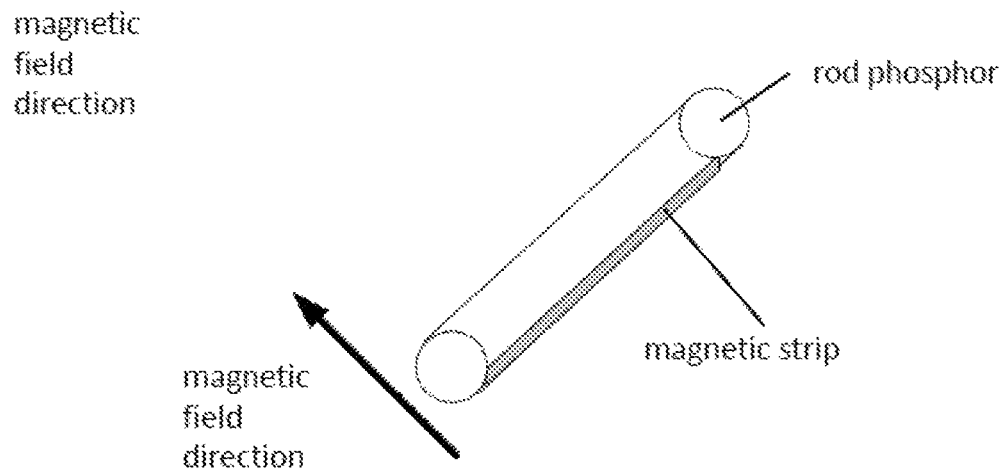
FIG. 17 depicts another embodiment of the invention where the phosphorescent or fluorescent material is shaped in the form of a rod (or other elongated shape)

FIG. 17 depicts another embodiment of the invention where the phosphorescent or fluorescent material is shaped in the form of a rod (or other elongated shape). A magnetic strip exist along a longitudinal axis that serves for orientation of the rod and for reflection of the emitted light. This constriction can be made along similar ways as the fabricated engineered particles described above in FIG. 13 but by starting not with hemispherical spheres in the base wafer but rather by etching trenches.

In one embodiment, multiple hard shell capsules can be inserted in the vicinity of a target or diseased site along with "simple" phosphorescent or fluorescent particles or rods not having a fluidic compartment. In one embodiment, multiple hard shell capsules can be inserted in the vicinity of a target or diseased site along with the insertion devices described above. In one embodiment, the multiple hard shell capsules, the simple phosphorescent or fluorescent particles, and the insertion devices can all be used interchangeably or in conjunction to treat a target site.

In one embodiment, multiple insertion devices are inserted into the vicinity of the target site and work in tandem to treat the target site. The multiple insertion devices are either remote controlled or are preprogrammed and optionally grafted in the body (in the diseased are of the micro-environment surrounding the diseased area).

Figure 18:
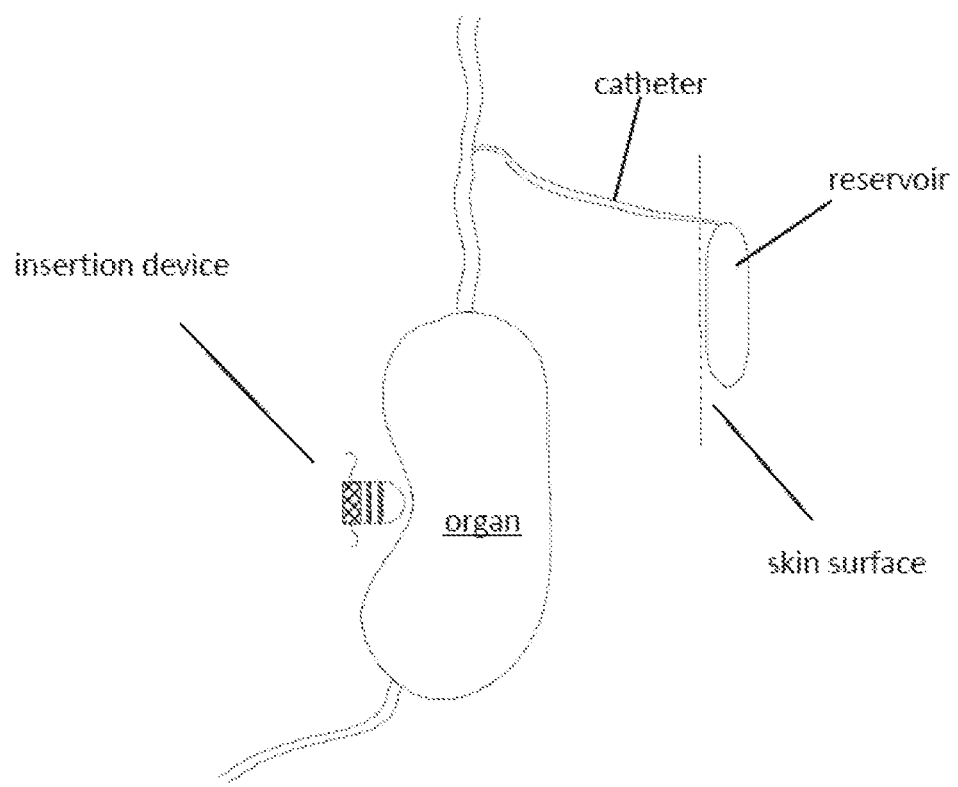
FIG. 18 is a schematic representation of an insertion device grafted in place adjacent an organ (i.e. a target site)

FIG. 18 is a schematic representation of an insertion device grafted in place adjacent an organ (i.e. a target site). Upon emission of light from the insertion device, a photoactivatable drug (i.e., a biotherapeutic agent or an adjuvant agent or a combination) elsewhere supplied to the organ than from the insertion device absorbs the emitted light and binds to diseased cells in the organ. In this embodiment shown in FIG. 18, a reservoir located outside the body provides the photoactivatable drug to the organ through a catheter. In this embodiment shown in FIG. 18, the insertion device is LED capsule with an on board battery where the battery can be charged remotely and a processor in the capsule can be programmed or triggered remotely.

Figure 19:
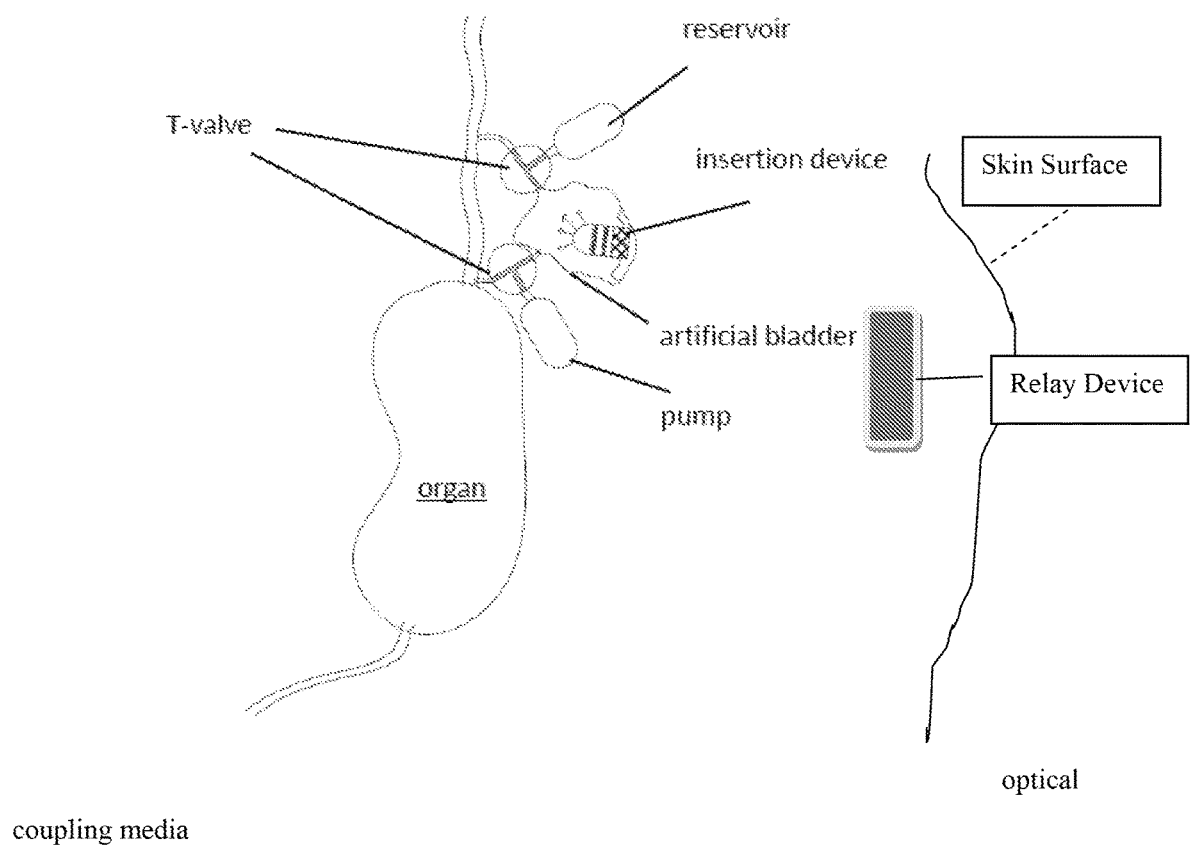
FIG. 19 is a schematic representation of an insertion device grafted in place nearby a region containing blood from a vasculature surrounding a diseased area.

FIG. 19 is a schematic representation of an insertion device grafted in place nearby a region containing blood from a vasculature surrounding a diseased area, for example of an organ. In the embodiment shown in FIG. 19, a controllable T-valve takes blood from the vasculature surrounding the diseased area and mixes the blood from a reservoir containing a bio-therapeutic agent. The blood is passed to a conformable bladder (acting as a port where the blood is exposed to the emitted light) that treats the mixture of blood and medication using light from the LED capsule. A secondary T-valve takes the treated blood from one port and forces it into circulation using a pump to create the right pressure conditions. The pump can utilize the pump/valve 40, the fluid reservoir 38, the fluid conduit channel 46, and/or the conduit 44 described above with regard to FIG. 2B to pump the blood and/or provide a biotherapeutic or photoactivatable agent to the blood.

With the embodiment shown in FIG. 19, the combination of modular systems (reservoir, T-valves, LED capsule, pump) can permit treatment to be performed around a major artery for systemic circulation. This inventive system and method can replace the conventional well established psoralen and ultraviolet A (PUVA) radiation treatments.

The emitted light treats the blood supply or directly treats organs of the human or animal subject. The energy modulation agent can be at least one of a phosphorescent or fluorescent agent, including at least one of a sulfide, a telluride, a selenide and an oxide semiconductor and a combination thereof.

In one embodiment of the invention, as shown in FIG. 19, there is a relay device utilized. The relay device's function is to mediate the communication between the programmable micro-device (or microdevices as the case may be) and the outside world where a computerized system monitors and provide feedback as to the next process step to be performed. By doing so, even faint and weak signals from the micro-device can be picked up and relayed to the computerized system (control) monitoring and guiding the process.

Hence, in one embodiment of the invention, a system for emitting a wavelength of energy internal to a medium or internal to a human or animal subject includes an embedded insertion-device embedded within a region of a human or animal subject, a computerized control controlling an external source of electro-magnetic transmissions outside the human or animal subject, and an embedded relay unit embedded within the region of a human or animal subject and disposed between the embedded insertion-device and the outside world. The embedded relay passes the electromagnetic transmissions, and is in communication with the embedded insertion device.

In one embodiment of the invention, the embedded relay is programmed to functions as a booster to alleviate loss of transmission of the electro-magnetic transmissions through a thick section of the human body where signal aberration and loss can occur.

Controlled Release of a Biotherapeutic Agent and/or One or More Energy Modulation Agents:

In terms of special coatings and materials with special properties, sodium silicates and other silicates are suitable for the present invention. A gelatinous precipitate of condensed Silicic acids ($SiO_2.H_2O$) is obtained when an ordinary acid including HCl is added to a solution of sodium silicate. When this precipitate is partially dehydrated it forms a porous material widely referred to as silica gel. This material can be impregnated with a bio therapeutic agent for its slow release once embeded inside the human body. Furthermore, the release of the bio-therapeutic agent can be made to accelerate if some of the bonds are made with Pb, Phosphorous network formers. Such materials would partially lose their integrity leading to more release of the biotherapeutic in the body. Both of the phosphors (that are UV emitters under X-Ray energy) as well as the porous materials (that are impregnated with the biotherapeutic agent) can be delivered to the tumor site (as implants). The added benefit of this technique is that the releasing of the bio therapeutic agent is only taking place when X-Ray is sensed and the phosphors are only activating UV when the X-Ray energy is turned on. Such atreatment would be used for osteosarcomas for examples where these materials are implanted (drilled into) the bone. Then the frequency of X-Ray treatment dictates the frequency with which the treatment is delivered. Other examples would include the jaw bone where the phosphors and impregnated porous gels are implanted at the root of a tooth and exposed to a dental X-Ray delivering imaging doses to activate the therapy.

In one embodiment of the invention pertaining to the release of energy modulation agents, the energy modulation agent (the above-noted phosphors) can be at least one of $CaWO_4:Pb^{2+}$, $CaWO_4:W$, $Sr_3(PO_4)_2$: $Eu^{2+}$, $Ba_3(PO_4)_2$: $Eu^{2+}$, $Y_2SiO_5:Ce^{3+}$, $SrMg(SiO_4)_2:Eu^{2+}$, $BaMg_2Al_{14}O_{24}:Eu^{2+}$, $ZnSiO_4:Mn^{2+}$, $Y_3(Al,Ga)_5O_{12}:Ce^{3+}$, $BaMg_2Al_{14}O_{24}:Mn^{2+}$, $BaMgAl_{14}O_{23}:Mn^{2+}$, $SrAl_{12}SiO_{19}:Mn^{2+}$, $ZnAl_{12}O_{19}:Mn^{2+}$, $CaAl_{12}O_{19}:Mn^{2+}$, $YBO_3:Tb^{3+}$, $Sr_4Si_3O_8Cl_4:Eu^{3+}$, $Y_2O_3:Eu^{3+}$, $Y_2SiO_5:Eu^{3+}$, $Y_3Al_5O_{12}Eu^{3+}$, $CaSiO_3:Mn^{2+}$, $YVO_4:Eu^{3+}$.

In one embodiment pertaining to the release of energy modulation agents, the energy modulation agent can further include a plasmonics agent comprising a dielectric-metal composite; or a plasmonics agent comprising a plurality of differently sized metal particles disposed in vicinity of each other as a composite plasmonics agent.

In one embodiment pertaining to the release of energy modulation agents, the energy modulation agent can be at least one of $Y_2O_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb $ZnS:Tb^{3+}$, $Er^{3+}$; $ZnS:Tb^{3+}$; $Y_2O_3:Tb^{3+}$; $Y_2O_3:Tb^{3+}$, $Er3^+$; $ZnS:Mn^{2+}$; ZnS:Mn, $Er^{3+}$; $CaWO_4$, $YaTO_4$, $YaTO_4$:Nb, $BaSO_4$:Eu, $La_2O_2S$:Tb, $BaSi_2O_5$:Pb, NaI(Tl), CsI(Tl), CsI(Na), CsI(pure), CsF, KI(Tl), LiI(Eu), $BaF_2$, CaF, $CaF_2$(Eu), ZnS(Ag), $CaWO_4$, $CdWO_4$, YAG(Ce) ($Y_3Al_5O_{12}$(Ce)), BOO bismuth germanate, GSO gadolinium oxyorthosilicate, LSO lutetium oxyorthosilicate, $LaCl_3$(Ce), and $LaBr_3$(Ce).

The above noted energy modulation agents (and others known in the art or described elsewhere in this specification) can be used as the passive devices described above or in conjunction with the active devices described above by their positioning near a diseased or target site to be treated.

The above noted energy modulation agents (and others known in the art or described elsewhere in this specification) cab injected from the insertion devices in saline solutions or in solutions containing the above-noted photoactivatable drugs or biotherapeutics.

Blood Processing and Treatment with and without Insertion Devices—

Blood performs many functions including transporting nutrients and oxygen to tissues and organs to regulating pH and temperature. It also provides an efficient transit system through the vascular network for transport of immune cells for defense against foreign microbes and wound healing. Broadly, plasma and cells constitute the two main blood components each with ~60% and 40% volume fractions respectively. The blood cellular components mainly consist of red blood cells (RBCs), leukocytes and platelets. Of the ~5 billion cells per milliliter of blood, red blood cells (RBCs) make up >99% of all cellular components. However, ultraviolet is greatly attenuated by RBCs.

Therefore, in one embodiment of the invention, there is provided a system for treating a patient or a subject with a photoactivatable drug where the system includes a source of a wavelength of energy which is capable of activating the photoactivatable drug and a blood supply displacement system (e.g. an organization of valves, pumps, reservoirs etc, as shown above in for example FIGS. 5, 18, and 19) and method thereof which displaces or flushes blood from a diseased site or organ to be treated. Displacing the blood is a biocompatible fluid which is less absorptive of the wavelength of energy than blood. Accordingly, in one embodiment of the invention, the resultant treatment is more likely to have the internal wavelength of energy photoactivate the photoactivatable drug than be absorbed by the subject or patient's blood. In one embodiment, the biocompatible fluid is a saline solution. In another embodiment, the biocompatible fluid is plasma. In another embodiment, the biocompatible fluid is plasma separated from the subject's blood supply. In another embodiment, the biocompatible fluid includes a photoactivatable drug such as for example psoralen or INA. In another embodiment, the biocompatible fluid includes a photoactivatable drug and/or a luminescing agent (such as for example a phosphorescent or a fluorescent agent). In one embodiment, the biocompatible fluid displaces the blood for a time period less than 10 minutes, preferably less than 5 minutes, more preferably less than 2 minutes, and still more preferably less than 1 minute. In one embodiment, the internal wavelength of energy is generated (during the time of displacement) inside the patient or subject by the passive devices of this invention. In one embodiment, the internal wavelength of energy is generated (during the time of displacement) inside the patient or subject by the active devices of this invention. In another embodiment, the displacement of blood occurs by needle injections of a saline solution and/or the photoactivatable drug solution.

Moreover, while described below as an insertion device, the microfluidic devices described below need not be inserted within the body of a subject or patient, but may reside outside the body.

According to one embodiment of the invention, the insertion devices described above can include or can be supplemented with microfluidic devices permitting the RBCs to be separated or diverted from the organ, while plasma (from the remaining blood) and/or a saline solution is pumped through the diseased organ or site. In one embodiment, similar to that shown above, valves are used to divert the blood supply and a reservoir of plasma or saline can be substituted for the blood flow. While prolonged periods of RBCs would be detrimental to the diseased and healthy cells in the organ, for short durations (e.g., 10 sec to 2 min.), the effects are not expected to be detrimental during this gap time of blood diplacement when no RBCs flow. Furthermore, according to one embodiment of the invention, it is during the gap period, preferably in the last half or last quarter that a photoactivatable drug such as psoralen is applied and activated by UV light (or other wavelength of radiation) from the light emitting insertion device. If the insertion device is a passive device (see discussion above), then the UV or other wavelength of radiation is generated during the gap period as detailed above by phosphorescent or fluorescent agents (or other luminescing agent) disposed in or nearby the diseased organ or site Over the past decade, new microfluidic based technologies have emerged to process clinical blood samples. Microfluidics is the science of studying fluid flow behavior at the microscale and the development of miniaturized analysis systems that take advantage of the unique physics emergent at these small scales. Microfluidic devices are capable of plasma and RBC separation using acoustophoresis. With this approach in the present invention, a microchannel containing the whole blood is excited by a $\lambda/2$ wavelength ultrasonic standing wave which concentrates the RBCs at the channel center by the primary acoustic radiation force. The acoustic forces generated by ultrasonic standing waves can be used for plasma separation in microchannels. The radiation force generated on the cells by these acoustic waves moves them into pressure nodes of the standing wave field. By exciting the microfluidic channel with half wavelength width ultrasonic wave, the cells/particles can be focused at the pressure node located at the center of the channel. Typically, in these devices, a transducer is placed underneath a chip containing the microchannel and outlet, and the transducer generates an ultrasonic standing wave between the channel walls perpendicular to the flow. A multiple outlet system permits the enriched blood cell fractions to be removed from the center of the channel, while a clean plasma fraction can be withdrawn from the side, and used in the present invention to provide plasma to a diseased or target site thereby displacing the blood from the site during a time of drug photoactivation.

U.S. Pat. Appl. No. 2014/0008307 (the entire contents of which are incorporated herein by reference) describes two-stage microfluidic devices using surface acoustic waves and having a particle focusing stage including: at least a first pair of surface acoustic wave generators, the first pair of surface acoustic wave generators are positioned opposite one another, and a first channel disposed between the first pair of surface acoustic wave generators; a particle separating stage including: a second pair of surface acoustic wave generators, the pair of surface acoustic wave generators are positioned opposite one another, and a second channel disposed between the second pair of surface acoustic wave generators; with the first channel and the second channel being in fluidic communication with one another. U.S. Pat. Appl. No. 2008/0181828 (the entire contents of which are incorporated herein by reference) describes a one-quarter wave separation chamber of an ultrasound resonator which is effective at particle/fluid/living cell separation. The '828 ultrasound resonator is part of a continuous flow closed system, and is optically monitored for cell type/volume near each exit port to control outlet valves maintaining collection purity. Uncollected cells/plasma can return to donor patient. In the '828 system, nonresonant secondary ultrasound can be applied to the resonator to fluidize/facilitate aggregated cell egress from exit ports.

U.S. Pat. No. 6,664,104 (the entire contents of which are incorporated herein by reference) describes a device for separating an analyte from a fluid sample comprises a cartridge incorporating a flow-through microfluidic chip. The '104 microfluidic chip includes an extraction chamber having an array of microstructures for capturing the analyte and for subsequently releasing the captured analyte into an elution fluid. Each of the microstructures has an aspect ratio of at least 2:1. The '104 cartridge also includes channels and at least one low controller (e.g., one or more valves) for directing the flow of the sample and elution fluid through the microfluidic chip. U.S. Pat. Appl. No. 2013/0175226 (the entire contents of which are incorporated herein by reference) describes an acoustic separator having two parallel chamber walls defining a separation chamber therebetween, each chamber wall defining one side of the chamber; inlet means through which fluid can flow into the chamber; and outlet means through which fluid can flow out of the chamber. One of the chamber walls includes a transducer arranged to transmit pressure waves across the chamber towards the other of the chamber walls which in turn is arranged to reflect the pressure waves to set up a standing wave in the chamber. The outlet means defines an opening in one of the sides of the chamber.

Such microfluidic devices and others known in the art would be capable, according to the invention, of the separation of RBCs during the aforementioned gap time when plasma or a saline solution would supply a photoactivatable drug to the diseased organ or site for activation by UV light or other wavelength of energy.

In another embodiment of the invention, the microfluidic devices permit circulating tumor cells to be collected from the blood stream exiting a diseased organ or site. As background, circulating tumor cells (CTCs) in blood is an important intermediate step in cancer metastasis, which accounts for ~90% of all cancer related deaths. Clinical studies have shown that enumeration of CTCs can be correlated with cancer progression.

Due to the large size differences between CTCs and other blood cellular components (CTCs ~16-20 µm; RBC ~8 µm;

leukocytes ~10-15 μm), size-based CTCs separation in microfluidic devices is often achieved using microstructures of different geometries to physically trap the larger CTCs. The engineered dimension in these devices has been the size of the pore/structure which is designed to allow maximum CTCs trapping with little contamination. Using spacing or sieve sizes between 5 to 10 μm, microfluidic devices have been used for isolation of cancer cells with high efficiency (>80%).

In one embodiment of the invention, the isolated CTCs are then treated with a photoactivatable drug such as psoralen, UV activated, and returned to the blood stream by reverse pumping of blood backwards through the sieve. In one embodiment of the invention, microfluidic devices can be used for separation and collection of CTCs from a patient or subject's blood stream as a monitor of cancer progression or regression over time.

In one embodiment of the invention, microfluidic devices can be used for separation and treatment of microorganisms (e.g., CTCs, bacterial agents, and viral agents) in the blood stream. Separation of microorganisms from blood has been primarily used as a therapeutic blood cleansing method for treating sepsis, a lethal disease caused by a systemic microbial infection that spreads via the bloodstream and compromises the body's immunological system. Antibiotics are often the main course of treatment, but inflammation continues to spread for a few hours before the drugs are effective. As noted above, psoarelen once photoactivated is effective in cancer cell apoptosis, engendering an autovaccine response from the human body. As noted above, iodonophthylazide (INA) once photoactivated is an effective antiviral and antibacterial agent engendering an autovaccine response from the human body. Accordingly, in one embodiment of the invention, isolated microorganisms are treated with a photoactivatable drug such as psoralen or INA, UV activated, and returned to the blood stream for example by reverse pumping of blood backwards through the sieve.

U.S. Pat. Appl. No. 2011/0301058 (the entire contents of which are incorporated herein by reference) describes a microfluidic device fabricated as Monolithic Internal micro Pillars (MIPi) made of SU-8 photoresist in which a microfluidic chip with the internal pillars (a MIPi chip) was used for cell capturing. The surface of MIPi was coated with specific antibody and then used for capturing cells by affinity binding. An antibody, anti-EGFR, which has high affinity to lung cancer cells, CL1-5 was coated on the micro pillars. The coated MIPi chip specifically captured the cancer cells that were pumped through the MIPi chip. This device with the specific coatings noted would be especially useful in the present invention for monitoring of the cancer progression or regression over time, but could also be used for collection, treatment, and release of the treated cells for example by way of heating the micro pillars to release the cells.

For example, in Gurkan et al. "Controlled viable release of selectively captured label-free cells in microchannels" in Lab Chip. 2011 Dec. 7; 11(23): 10.1039/c11c20487d (the entire contents of which are incorporated herein by reference) describe that rapid heating to (37° C.) and cooling (<32° C.) of their microchannels (achieved by the small liquid volume of 10 μL) allowed release of bound species. More specifically, Gurkan et al, described the following heating/cooling sequence applicable to the present invention using a microfluidic chip composed of three parallel channels (4 mm×22 mm×80 μm), one of which (middle channel) was used as the temperature indicator channel. Blood was introduced into the top and bottom release channels. A channel surface at 37° C. captured cells on the channel surface thereof, with the non-captured cells in the channels rinsed away. The microchip was then cooled down below 32° C. (in less than 5 minutes). The released cells were rinsed out of the channels and collected at the channel outlet.

U.S. Pat. No. 8,834,794 (the entire contents of which are incorporated herein by reference) describes a disposable handheld device for detecting circulating tumor cells (CTC) in blood (HCTCD). The HCTCD is capable of detecting less than 1 CTC per milliliter. The HCTCD consists of a dense array of high aspect ratio freestanding metallic nanoneedles, functionalized with antibodies that integrated within a microfluidic device and selectively capture and count (using electrical signal detection) the CTCs. By selecting a right functionalization protocol for the nanoneedles array, the HCTCD can be used for selective capturing a variety of rare cells that are mixed in human fluids. This device with the specific antibodies noted would be especially useful in the present invention for monitoring of the cancer progression or regression over time, but could also be used for collection, treatment, and release of the treated cells for example by way of heating the nanoneedles to release the cells.

U.S. Pat. Appl. No. 2014/0061049 (the entire contents of which are incorporated herein by reference) describes a printed circuit with a microfluidic device and the wirelessly powering the microfluidic device. The '049 microfluidic device includes a substrate with a fluidic channel to provide a path for a fluid with particles. The fluidic channel includes fluid inlet and outlet. A pair of electrodes near the inlet and the outlet guides the particles toward a center of the fluidic channel using negative-dielectrophoresis (DEP) effect in response to an alternating current (AC) frequency voltage received at the pairs of electrodes. Additional pairs of electrodes are disposed along a border of the fluidic channel between the pairs of electrodes near the inlet and the outlet of the fluidic channel to isolate a subpopulation of the particles using positive and negative DEP effects in response to AC voltages of different frequencies received at different ones of the additional pairs of electrodes. Plasma and RBCs separation could be accomplished in the invention with this kind of device.

As described in the '049 application and as suitable for the present invention to capture preferentially CTCs or microorganisms, cells with different size experience different amounts of dielectrophoretic force when passing through the electrode pair. Cells experiencing negative dielectrophoresis (DEP) will be deflected into upper chambers while cells subject to positive DEP will flow into lower chambers. The cells are then subdivided by the travelling DEP force generated by the parallel array electrodes. The phase difference between these electrodes is 90°. For example, if the first electrode in the array has a phase of 0°, the subsequent electrodes will have phases of 90°, 180° and 270°, respectively. Cells subjected to positive traveling DEP are deflected to different regions of the device than those subject to negative DEP. In such a way, cells are grouped by like kind.

Such microfluidic devices and others known in the art would be capable, according to the invention, of the capture of CTCs or microorganisms from the blood supply and treatment thereof with a photoactivatable drug with its activation by UV light or other wavelength of energy.

Generalized Statements of the Invention

The following statements of the invention provide one or more characterizations of the invention and do not limit the scope of the invention.

1. A system for emitting a wavelength of energy internal to a medium or internal to a human or animal subject, comprising: a source configured to produce an initiation signal penetrating at least a part of the medium or the human or animal subject; an insertion device having an electronics assembly unit. The assembly unit comprises an emitter configured to emit said wavelength of energy of a predetermined type 1) to treat a disease or disorder in the human or animal subject or 2) to produce a change in the medium, and a receiver that receives the initiation signal. The assembly unit is configured, upon receiving the signal, to power the emitter to thereby emit said wavelength of energy interior the human or animal subject or interior the medium.

2. The system of statement 1, where the emitter comprises a microemitter capsule ranging in size from 100 microns to less than a centimeter.

3. The system of statement 1 or 2, where the emitter comprises a light emitting diode or an electroluminescent device configured to emit said wavelength of energy.

4. The system of any one of statements 1 to 3, wherein the initiation signal is a low frequency RF or microwave signal which traverses parts of or the entirety of the human or animal subject or the medium.

5. The system of any one of statements 1 to 4, wherein the insertion device comprises a container having a containment wall comprising at least one of a silicate glass, an alkali glass, a sodium glass, and a phosphate glass.

6. The system of any one of statements 1 to 5, further comprising:
a fluid reservoir;
at least one fluid channel from the reservoir to outside of the insertion device.

7. The system of statement 6, wherein the fluid reservoir contains at least one of a fluid of an activatable pharmaceutical agent or a fluid of nanoparticles.

8. The system of statement 7, wherein the at least one activatable pharmaceutical agent is present and, upon activation by the emitted wavelength of energy treats a cell proliferation disorder selected from the group consisting of cancer, bacterial infection, viral infection, immune rejection response, autoimmune disorders, aplastic conditions, and combinations thereof.

9. The system of statement 7 or 8, wherein the at least one activatable pharmaceutical agent is present and is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones.

10. The system of any one of statements 7 to 9, wherein the at least one activatable pharmaceutical agent is present and is a psoralen, a coumarin, a porphyrin or a derivative thereof.

11. The system of any one of statements 7 to 10, wherein the at least one activatable pharmaceutical agent is present and is 8-MOP or AMT.

12. The system of statement 7, wherein the at least one activatable pharmaceutical agent is present and is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematophorphyrin, and phthadocyanine.

13. The system of any one of statements 7 to 12, wherein the at least one activatable pharmaceutical agent is present and is coupled to a carrier that is capable of binding to a receptor site.

14. The system of statement 13, wherein the carrier is one selected from insulin, interleukin, thymopoietin or transferrin.

15. The system of statement 13 or 14, wherein the at least one activatable pharmaceutical agent is coupled to the carrier by a covalent bond.

16. The system of statement 13 or 14, wherein the at least one activatable pharmaceutical agent is coupled to the carrier by non-covalent bond.

17. The system of any one of statements 13 to 16, wherein the receptor site is one selected from nucleic acids of nucleated cells, antigenic sites on nucleated cells, or epitopes.

18. The system of any one of statements 7 to 17, wherein the cell proliferation disorder is treated by apoptosis in a target cell.

19. The system of any one of statements 7 to 18, wherein the at least one activatable pharmaceutical agent is present and is capable of being preferentially absorbed by a target cell.

20. The system of any one of statements 1 to 19, wherein said wavelength of energy induces a predetermined change in the target structure with or without an energy modulation agent or a photoactive agent.

21. The system of statement 20, wherein the energy modulation agent is present and is configured to adsorb, intensify or modify said wavelength of energy.

22. The system of statement 20 or 21, wherein the energy modulation agent is present and is configured to transform the wavelength of energy into a photonic or another electromagnetic energy that affects the predetermined change in said target structure.

23. The system of any one of statements 20 to 22, wherein the energy modulation agent emits secondary light at a decreased wavelength compared to the wavelength of energy.

24. The system of any one of statements 20 to 22, wherein the energy modulation agent emits secondary light at an increased wavelength compared to the wavelength of energy.

25. The system of any one of statements 20 to 24, wherein the energy modulation agent is present and comprises one or more members selected from a biocompatible fluorescing metal nanoparticle, fluorescing metal oxide nanoparticle, fluorescing metal coated metal oxide nanoparticle, fluorescing dye molecule, gold nanoparticle, silver nanoparticle, gold-coated silver nanoparticle, a water soluble quantum dot encapsulated by polyamidoamine dendrimers, a luciferase, a biocompatible phosphorescent molecule, a combined electromagnetic energy harvester molecule, and a lanthanide chelate exhibiting intense luminescence.

26. The system of any one of statements 20 to 25, wherein the energy modulation agent is present and comprises at least one of a phosphorescent or fluorescent agent.

27. The system of any one of statements 20 to 26, wherein the energy modulation agent is present and comprises at least one of at least one of a sulfide, a telluride, a selenide and an oxide semiconductor and a combination thereof.

28. The system of any one of statements 20 to 26, wherein the energy modulation agent is present and comprises at least one of $CaWO_4:Pb^{2+}$, $CaWO_4:W$, $Sr_3(PO_4)_2: Eu^{2+}$, $Ba_3(PO_4)_2: Eu^{2+}$, $Y_2SiO_5:Ce^{3+}$, $SrMg(SiO_4)_2:Eu^{2+}$, $BaMg_2Al_{14}O_{24}:Eu^{2+}$, $ZnSiO_4:Mn^{2+}$, $Y_3(Al,Ga)_5O_{12}:Ce^{3+}$, BaMg$_2$Al$_{14}$O$_{24}$:Mn$^{2+}$, BaMgAl$_{14}$O$_{23}$:Mn$^{2+}$, SrAl$_{12}$SiO$_{19}$:Mn$^{2+}$, ZnAl$_{12}$O$_{19}$: Mn$^{2+}$, CaAl$_{12}$O$_{19}$:Mn$^{2+}$, YBO$_3$:Tb$^{3+}$, Sr$_4$Si$_3$O$_8$Cl$_4$:Eu$^{3+}$, Y$_2$O$_3$:Eu$^{3+}$, Y$_2$SiO$_5$:Eu$^{3+}$, Y$_3$Al$_5$O$_{12}$Eu$^{3+}$, CaSiO$_3$:Mn$^{2+}$, YVO$_4$:Eu$^{3+}$.

29. The system of any one of statements 20 to 28, wherein the energy modulation agent is present and further comprises a plasmonics agent comprising a dielectric-metal composite; or a plasmonics agent comprising a plurality of differently sized metal particles disposed in vicinity of each other as a composite plasmonics agent.

30. The system of any one of statements 20 to 29, wherein the energy modulation agent is present and comprises at least one of Y$_2$O$_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb ZnS:Tb$^{3+}$, Er$^{3+}$; ZnS:Tb$^{3+}$; Y$_2$O$_3$:Tb$^{3+}$; Y$_2$O$_3$:Tb$^{3+}$, Er3$^+$; ZnS:Mn$^{2+}$; ZnS:Mn, Er$^{3+}$; CaWO$_4$, YaTO$_4$, YaTO$_4$:Nb, BaSO$_4$:Eu, La$_2$O$_2$S:Tb, BaSi$_2$O$_5$:Pb, NaI(Tl), CsI(Tl), CsI(Na), CsI(pure), CsF, KI(Tl), LiI(Eu), BaF$_2$, CaF, CaF$_2$(Eu), ZnS(Ag), CaWO$_4$, CdWO$_4$, YAG(Ce) (Y$_3$Al$_5$O$_{12}$(Ce)), BOO bismuth germanate, GSO gadolinium oxyorthosilicate, LSO lutetium oxyorthosilicate, LaC1$_3$(Ce), and LaBr$_3$(Ce).

31. The system of any one of statements 1 to 30, wherein: said insertion device is disposed in a fluidized bed;
said insertion device is disposed in re-entrant structures extending into an artificial container holding said medium; or said insertion device is disposed on interior walls of an artificial container holding said medium.

32. The system of any one of statements 1 to 31, wherein interaction of at least one photoactivatable agent in the medium after activation by said wavelength of energy cures a polymer in the medium.

33. The system of statement 32, wherein the photoactivatable agent comprises photoinitiator including at least one of benzoin and substituted benzoins, Michler's ketone, dialkoxyacetophenones, benzophenone and substituted benzophenones, acetophenone and substituted acetophenones, and xanthone and substituted xanthones, benzoin methyl ether, benzoin ethyl ether, benzoin isopropyl ether, diethoxyxanthone, chloro-thio-xanthone, azo-bisisobutyronitrile, N-methyl diethanolaminebenzophenone, camphoquinone, peroxyester initiators and non-fluorene-carboxylic acid peroxyesters.

34. A system for emitting a wavelength of energy internal to a medium or internal to a human or animal subject, comprising:
an emitter configured, in response to an initiation signal, to emit said wavelength of energy of a predetermined type to treat a disease or disorder in the human or animal subject or to produce a change in the medium,
a controller which provides a control signal moderating an amount of said wavelength of energy being emitted in the human or animal subject.

35. The system of statement 34, wherein the emitter comprises an active device including a receiver for reception of at least one of the initiation signal and the control signal.

36. The system of statement 34 or 35, wherein the emitter further comprises a processor which contains programmed instructions determining a schedule for administration of said wavelength of energy to the medium or internal to the human or animal subject.

37. The system of any one of statements 34 to 36, wherein the emitter comprises a light emitting diode or an electroluminescent device configured to emit said wavelength of energy.

38. The system of any one of statements 34 to 37, further comprising a fluid reservoir including a biotherapeutic fluid.

39. The system of statement 38, further comprising at least one fluid channels for delivery of the biotherapeutic fluid to the human or animal subject.

40. The system of any one of statements 34 to 37, further comprising a fluid reservoir including a photoactivatable fluid.

41. The system of statement 40, further comprising at least one fluid channel for delivery of the photoactivatable fluid to the medium or to the human or animal subject.

42. The system of any one of statements 34 to 37, further comprising an x-ray breakable container holding at least one of a biotherapeutic fluid or a photoactivatable fluid, wherein upon x-ray exposure a container wall breaks releasing said at least one of a biotherapeutic fluid or a photoactivatable fluid to the medium or to the human or animal subject.

43. The system of statement 42, wherein the x-ray breakable container comprises a glass including at least one of a silicate glass, an alkali glass, a sodium glass, and a phosphate glass doped with a heavy metal.

44. The system of statement 43, wherein the heavy metal in the glass comprises at least one of Pb, Cr, and Th.

45. The system of any one of statements 34 to 44, wherein the emitter comprises a passive device without electrical circuitry.

46. The system of statement 45, wherein the passive device comprises at least one of a phosphorescent or fluorescent agent.

47. The system of statement 45 or 46, wherein the passive device comprises at least one of at least one of a sulfide, a telluride, a selenide and an oxide semiconductor and a combination thereof.

48. The system of any one of statements 45 to 47, wherein the passive device comprises at least one of CaWO$_4$:Pb$^{2+}$, CaWO$_4$:W, Sr$_3$(PO$_4$)$_2$: Eu$^{2+}$, Ba$_3$(PO$_4$)$_2$: Eu$^{2+}$, Y$_2$SiO$_5$:Ce$^{3+}$, SrMg(SiO$_4$)$_2$:Eu$^{2+}$, BaMg$_2$Al$_{14}$O$_{24}$:Eu$^{2+}$, ZnSiO$_4$:Mn$^{2+}$, Y$_3$(Al,Ga)$_5$O$_{12}$:Ce$^{3+}$, BaMg$_2$Al$_{14}$O$_{24}$:Mn$^{2+}$, BaMgAl$_{14}$O$_{23}$:Mn$^{2+}$, SrAl$_{12}$SiO$_{19}$:Mn$^{2+}$, ZnAl$_{12}$O$_{19}$: Mn$^{2+}$, CaAl$_{12}$O$_{19}$:Mn$^{2+}$, YBO$_3$:Tb$^{3+}$, Sr$_4$Si$_3$O$_8$Cl$_4$:Eu$^{3+}$, Y$_2$O$_3$:Eu$^{3+}$, Y$_2$SiO$_5$:Eu$^{3+}$, Y$_3$Al$_5$O$_{12}$Eu$^{3+}$, CaSiO$_3$:Mn$^{2+}$, YVO$_4$:Eu$^{3+}$.

49. The system of any one of statements 45 to 48, wherein the passive device comprises a plasmonics agent comprising a dielectric-metal composite; or a plasmonics agent comprising a plurality of differently sized metal particles disposed in vicinity of each other as a composite plasmonics agent.

50. The system of any one of statements 45 to 49, wherein the passive device comprises at least one of Y$_2$O$_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb ZnS:Tb$^{3+}$, Er$^{3+}$; ZnS:Tb$^{3+}$; Y$_2$O$_3$:Tb$^{3+}$; Y$_2$O$_3$:Tb$^{3+}$, Er3$^+$; ZnS:Mn$^{2+}$; ZnS:Mn, Er$^{3+}$; CaWO$_4$, YaTO$_4$, YaTO$_4$:Nb, BaSO$_4$:Eu, La$_2$O$_2$S:Tb, BaSi$_2$O$_5$:Pb, NaI(Tl), CsI(Tl), CsI(Na), CsI(pure), CsF, KI(Tl), LiI(Eu), BaF$_2$, CaF, CaF$_2$(Eu), ZnS(Ag), CaWO$_4$, CdWO$_4$, YAG(Ce) (Y$_3$Al$_5$O$_{12}$(Ce)), BGO bismuth germanate, GSO gadolinium oxyorthosilicate, LSO lutetium oxyorthosilicate, LaCl$_3$(Ce), and LaBr$_3$(Ce).

51. The system of any one of statements 34 to 50, further comprising: a mechanism to administer to a subject at least one activatable pharmaceutical agent that is capable of producing a predetermined cellular change when activated by said wavelength of energy to treat a cell proliferation related disorder.

52. The system of statement 51, wherein the cell proliferation disorder is at least one member selected from the group consisting of cancer, bacterial infection, viral infection, immune rejection response, autoimmune disorders, aplastic conditions, and combinations thereof.

53. The system of statement 51 or 52, wherein the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones.

54. The system of any one of statements 51 to 53, wherein the at least one activatable pharmaceutical agent is a psoralen, a coumarin, a porphyrin or a derivative thereof.

55. The system of any one of statements 51 to 54, wherein the at least one activatable pharmaceutical agent is 8-MOP, TMP, or AMT.

56. The system of any one of statements 51 to 52, wherein the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthadocyanine tetrasulonate, hematophorphyrin, and phthadocyanine.

57. The system of any one of statements 51 to 56, wherein the predetermined cellular change is apoptosis in a target cell.

58. The system of any one of statements 51 to 57, wherein the at least one activatable pharmaceutical agent causes an auto-vaccine effect in the subject that reacts with a target cell.

59. The system of any one of statements 51 to 58, wherein the at least one activatable pharmaceutical agent is a DNA intercalator or a halogenated derivative thereof.

60. The system of any one of statements 51 to 59, wherein the at least one activatable pharmaceutical agent upon activation binds to DNA associated with the cell proliferation related disorder.

61. The system of any one of statements 51 to 60, wherein the at least one activatable pharmaceutical agent intercalates DNA associated with the cell proliferation related disorder and upon activation binds to the DNA.

62. A directional energy modulator for converting initiation energy into a wavelength of energy emitted in a preferential direction, comprising:
a layered assembly including,
at least one layer of an energy converting material which absorbs the initiation energy and emits said wavelength of energy, and
multiple layers of an energy reflecting material disposed around said at least one layer of the energy converting material,
wherein said wavelength of energy is reflected by the energy reflecting material and exits at a longitudinal end of the layered assembly.

63. The modulator of statement 62, wherein the layered assembly has a spherical shape.

64. The modulator of statement 62, wherein the layered assembly has a rectilinear shape.

65. The modulator of statement 62, wherein the layered assembly has a rod shape. 66. The modulator of statement 62, wherein the energy reflecting material comprises at least one of Ag, Au, Al, or Cu.

67. The modulator of any one of statements 62 to 66, wherein the energy reflecting material comprises a magnetic or paramagnetic material.

68. The modulator of any one of statements 62 to 67, wherein the energy reflecting material comprises a non-magnetic material.

69. The modulator of any one of statements 62 to 68, wherein the energy reflecting material comprises at least one of iron, nickel, cobalt, and alloys of rare earth metals.

70. The modulator of any one of statements 62 to 69, wherein a separation distance between layers in the layered assembly ranges from 10 nm to 1000 nm, or between 100 nm and 700 nm, or between 200 nm and 500 nm, or between 300 nm and 400 nm.

71. The modulator of any one of statements 62 to 69, wherein a separation distance between layers in the layered assembly ranges from 1 µm to 1000 µm, or between 10 µm and 100 µm, or between 100 µm and 500 µm, or between 300 µm and 400 µm.

72. A system for emitting a wavelength of energy internal to a medium or internal to a human or animal subject, comprising:
any one of the modulators of statements 62-71 configured, in response to an initiation signal, to emit said wavelength of energy of a predetermined type to treat a disease or disorder in the human or animal subject or to produce a change in the medium,
a magnetic field generator configured to provide a magnetic field along a predetermined direction which moderates a direction of said wavelength of energy being emitted in the human or animal subject.

73. A system for emitting a wavelength of energy internal to a human or animal subject, comprising:
an emitter disposed inside the human or animal subject, which in response to an initiation signal containing the initiation energy, emits said wavelength of energy to treat a disease or disorder in the human or animal subject;
a first blood supply valve disposed inside the human or animal subject, which diverts blood from a first blood vessel of the human or animal subject;
a port connected to the blood supply valve where the blood is exposed to the wavelength of energy;
a photoactivatable drug reservoir for delivery of a photoactivatable drug to the blood in the port; and
a second blood supply valve disposed inside the human or animal subject, which returns blood from the port back to a second blood vessel of the human or animal subject.

74. The system of statement 73, further comprising a pump disposed inside the human or animal subject for pumping said blood.

75. The system of statement 73 or 74, where the reservoir is disposed inside the human or animal subject.

76. The system of statement 73 or 74, where the reservoir is disposed outside the human or animal subject.

77. The system of any one of statements 73 to 76, further comprising an artificial bladder disposed inside the human or animal subject.

78. The system of any one of statements 73 to 77, where at least one of the emitter, the port, and the reservoir is disposed inside the artificial bladder.

79. The system of any one of statements 73 to 78, further comprising a pump disposed inside the artificial bladder for pumping said blood.

80. A medical catheter comprising:
an insertion device having an electronics assembly unit;
said assembly unit comprising,
an emitter,
a receiver that receives a signal for communication with the assembly unit; and
said assembly unit configured, upon receiving the signal, to power the emitter to emit a wavelength of energy of a predetermined type interior of the human or animal subject to treat the human or animal subject; and
an insertion sleeve including at a distal end thereof for insertion of the insertion device into a patient.

81. An emitter capsule comprising:
an assembly unit comprising,
an emitter,
a receiver that receives an initiation signal for communication with the assembly unit; and
said emitter emitting a wavelength of energy interior of the human or animal subject to treat the human or animal subject or emitting the wavelength of energy interior to the medium to produce a change in the medium.

82. An insertion device comprising:
an electronics assembly unit; and
a container configured to contain the electronics assembly unit and configured for insertion 1) into a body of a human or animal subject or 2) into a medium;
wherein said electronics assembly unit comprises,
an emitter configured to emit a wavelength of energy of a predetermined type 1) to treat a disease or disorder in the human or animal subject or 2) to produce a change in the medium,
said electronics assembly unit configured to power the emitter to thereby emit said wavelength of energy from the container.

83. An insertion device comprising:
an electronics assembly unit; and
a container configured to contain the electronics assembly unit and configured for insertion 1) into a body of a human or animal subject or 2) into a medium;
wherein said electronics assembly unit comprises,
an emitter configured to emit a wavelength of energy of a predetermined type 1) to treat a disease or disorder in the human or animal subject or 2) to produce a change in the medium,
a receiver that receives an initiation signal; and
said electronics assembly unit configured, upon receiving the initiation signal, to power the emitter to thereby emit said wavelength of energy interior the human or animal subject or interior the medium.

84. A system for emitting a wavelength of energy internal to a medium or internal to a human or animal subject, comprising:
an embedded insertion device embedded within a region of a human or animal subject;
a computerized control controlling an external source of electro-magnetic transmissions outside the human or animal subject;
a relay embedded within the region of a human or animal subject and disposed between the embedded insertion device and the outside world; and
said relay passes along the electro-magnetic transmissions to the embedded insertion device.

85. The system of statement 84, wherein the relay is programmed to functions as a booster to alleviate loss of transmission of the electro-magnetic transmissions through a thick section of the human body where signal aberration and loss can occur.

86. A system for treating a patient or a subject with a photoactivatable drug. comprising:
a source of a wavelength of energy which is capable of activating the photoactivatable drug; and
a blood supply displacement system which temporarily displaces blood from a diseased site or organ to be treated with a biocompatible fluid which is less absorptive of the wavelength of energy than blood.

87. A method for treating a condition, disorder, or disease, comprising:
generating an energy in-situ in a subject in need thereof, by way of (1) any one of the systems of statements 1-61, 72-79, or 84-86, (2) a medical catheter of statement 80, (3) an emitter capsule of statement 81, or (4) an insertion device of one of statements 82-83,
whereby the energy generated in-situ either (a) directly effects a change in the subject thus treating the condition, disorder, or disease, or (b) activates an activatable pharmacutical agent which has been administered prior to or simultaneously with generating the energy in-situ, whereby upon activation the activated activatable pharmaceutical agent effects a change thereby treating the condition, disorder, or disease.

Having generally described this invention, a further understanding can be obtained by reference to certain specific examples which are provided herein for purposes of illustration only and are not intended to be limiting unless otherwise specified.

Numerous modifications and variations of the invention are possible in light of the above teachings. It is therefore to be understood that within the scope of the appended statements, the invention may be practiced otherwise than as specifically described herein.

The invention claimed is:

1. A system for emitting a wavelength of energy internal to a medium or internal to a human or animal subject, comprising:
an emitter configured, in response to an initiation signal, to emit said wavelength of energy of a predetermined type to treat a disease or disorder in the human or animal subject or to produce a change in the medium,
a controller which provides a control signal moderating an amount of said light being emitted in the human or animal subject, and
an x-ray breakable container holding at least one of a biotherapeutic fluid or a photoactivatable fluid, wherein upon x-ray exposure a container wall breaks releasing said at least one of a biotherapeutic fluid or a photoactivatable fluid to the medium or to the human or animal subject.

2. The system of claim 1, wherein the emitter comprises an active device including a receiver for reception of at least one of the initiation signal and the control signal.

3. The system of claim 2, wherein the emitter further comprises a processor which contains programmed instructions determining a schedule for administration of said wavelength of energy to the medium or internal to the human or animal subject.

4. The system of claim 2, wherein the emitter comprises a light emitting diode or an electroluminescent device configured to emit said wavelength of energy.

5. The system of claim 2, further comprising a fluid reservoir including a biotherapeutic fluid.

6. The system of claim 5, further comprising at least one fluid channels for delivery of the biotherapeutic fluid to the human or animal subject.

7. The system of claim 2, further comprising a fluid reservoir including a photoactivatable fluid.

8. The system of claim 7, further comprising at least one fluid channel for delivery of the photoactivatable fluid to the medium or to the human or animal subject.

9. The system of claim 1, wherein the x-ray breakable container comprises a glass including at least one of a silicate glass, an alkali glass, a sodium glass, and a phosphate glass doped with a heavy metal.

10. The system of claim 9, wherein the heavy metal in the glass comprises at least one of Pb, Cr, and Th.

11. The system of claim 2, wherein the emitter comprises a passive device without electrical circuitry.

12. The system of claim 11, wherein the passive device comprises at least one of a phosphorescent or fluorescent agent.

13. The system of claim 11, wherein the passive device comprises at least one of a sulfide, a telluride, a selenide and an oxide semiconductor and a combination thereof.

14. The system of claim 11, wherein the passive device comprises at least one of $CaWO_4:Pb^{2+}$, $CaWO_4:W$, $Sr_3(PO_4)_2:Eu^{2+}$, $Ba_3(PO_4)_2:Eu^{2+}$, $Y_2SiO_5:Ce^{3+}$, $SrMg(SiO_4)_2:Eu^{2+}$, $BaMg_2Al_{14}O_{24}:Eu^{2+}$, $ZnSiO_4::Mn^{2+}$, $Y_3(Al,Ga)_5O_{12}:Ce^{3+}$, $BaMg_2Al_{14}O_{24}:Mn^{2+}$, $BaMgAl_{14}O_{23}:Mn^{2+}$, $SrAl_{12}SiO_{19}:Mn^{2+}$, $ZnAl_{12}O_{19}:Mn^{2+}$, $CaAl_{12}O_{19}:Mn^{2+}$, $YBO_3:Tb^{3+}$, $Sr_4Si_3O_8Cl_4:Eu^{3+}$, $Y_2O_3:Eu^{3+}$, $Y_2SiO_5:Eu^{3+}$, $Y_3Al_5O_{12}Eu^{3+}$, $CaSiO_3:Mn^{2+}$, $YVO_4:Eu^{3+}$.

15. The system of claim 11, wherein the passive device comprises a plasmonics agent comprising a dielectric-metal composite; or a plasmonics agent comprising a plurality of differently sized metal particles disposed in vicinity of each other as a composite plasmonics agent.

16. The system of claim 11, wherein the passive device comprises at least one of $Y_2O_3$; ZnS; ZnSe; MgS; CaS; Mn, Er ZnSe; Mn, Er MgS; Mn, Er CaS; Mn, Er ZnS; Mn, Yb ZnSe; Mn, Yb MgS; Mn, Yb CaS; Mn, Yb ZnS:$Tb^{3+}$, $Er^{3+}$; ZnS:$Tb^{3+}$; $Y_2O_3$:$Tb^{3+}$; $Y_2O_3$:$Tb^{3+}$, $Er^{3+}$; ZnS:$Mn^{2+}$; ZnS:Mn, $Er^{3+}$; $CaWO_4$, $YaTO_4$, $YaTO_4$:Nb, $BaSO_4$:Eu, $La_2O_2S$:Tb, $BaSi_2O_5$:Pb, NaI(Tl), CsI(Tl), CsI(Na), CsI(pure), CsF, KI(Tl), LiI(Eu), $BaF_2$, CaF, $CaF_2$(Eu), ZnS(Ag), $CaWO_4$, $CdWO_4$, YAG(Ce) ($Y_3Al_5O_{12}$(Ce)), BGO bismuth germanate, GSO gadolinium oxyorthosilicate, LSO lutetium oxyorthosilicate, $LaCl_3$(Ce), and $LaBr_3$(Ce).

17. The system of claim 1, further comprising: a mechanism to administer to a subject at least one activatable pharmaceutical agent that is capable of producing a predetermined cellular change when activated by said wavelength of energy to treat a cell proliferation related disorder.

18. The system of claim 17, wherein the cell proliferation disorder is at least one member selected from the group consisting of cancer, bacterial infection, viral infection, immune rejection response, autoimmune disorders, aplastic conditions, and combinations thereof.

19. The system of claim 17, wherein the at least one activatable pharmaceutical agent is selected from psoralens, pyrene cholesteryloleate, acridine, porphyrin, fluorescein, rhodamine, 16-diazorcortisone, ethidium, transition metal complexes of bleomycin, transition metal complexes of deglycobleomycin organoplatinum complexes, alloxazines, vitamin Ks, vitamin L, vitamin metabolites, vitamin precursors, naphthoquinones, naphthalenes, naphthols and derivatives thereof having planar molecular conformations, porphorinporphyrins, dyes and phenothiazine derivatives, coumarins, quinolones, quinones, and anthroquinones.

20. The system of claim 17, wherein the at least one activatable pharmaceutical agent is a psoralen, a coumarin, a porphyrin or a derivative thereof.

21. The system of claim 17, wherein the at least one activatable pharmaceutical agent is 8-MOP, TMP, or AMT.

22. The system of claim 17, wherein the at least one activatable pharmaceutical agent is one selected from 7,8-dimethyl-10-ribityl, isoalloxazine, 7,8,10-trimethylisoalloxazine, 7,8-dimethylalloxazine, isoalloxazine-adenine dinucleotide, alloxazine mononucleotide, aluminum (III) phthalocyanine tetrasulonate, hematophorphyrin, and phthadocyanine.

23. The system of claim 17, wherein the predetermined cellular change is apoptosis in a target cell.

24. The system of claim 17, wherein the at least one activatable pharmaceutical agent causes an auto-vaccine effect in the subject that reacts with a target cell.

25. The system of claim 17, wherein the at least one activatable pharmaceutical agent is a DNA intercalator or a halogenated derivative thereof.

26. The system of claim 17, wherein the at least one activatable pharmaceutical agent upon activation binds to DNA associated with the cell proliferation related disorder.

27. The system of claim 17, wherein the at least one activatable pharmaceutical agent intercalates DNA associated with the cell proliferation related disorder and upon activation binds to the DNA.

28. A method for treating a condition, disorder, or disease, comprising:
generating an energy in-situ in a subject in need thereof, by way of the system of claim 1,
whereby the energy generated in-situ either (a) directly effects a change in the subject thus treating the condition, disorder, or disease, or (b) activates an activatable pharmaceutical agent which has been administered prior to or simultaneously with generating the energy in-situ, whereby upon activation the activated activatable pharmaceutical agent effects a change thereby treating the condition, disorder, or disease.

\* \* \* \* \*

UNITED STATES PATENT AND TRADEMARK OFFICE
CERTIFICATE OF CORRECTION

Page 1 of 3

PATENT NO. : 11,077,316 B2
APPLICATION NO. : 16/096174
DATED : August 3, 2021
INVENTOR(S) : Bourke, Jr. et al.

It is certified that error appears in the above-identified patent and that said Letters Patent is hereby corrected as shown below:

In the Specification

In Column 9, Lines 33-34, delete "cytomegaloviris" and insert -- cytomegalovirus --, therefor.

In Column 18, Line 67, delete "mitochondriat" and insert -- mitochondria --, therefor.

In Column 21, Line 65, delete "0<x≤1, and 0<y≤1)." and insert -- 0<x≦1, and 0<y≦1). --, therefor.

In Column 22, Line 2, delete "0<x≤1, 0<y≤1, 0<z≤1)." and insert -- 0<x≦1, 0<y≦1, 0<z≦1). --, therefor.

In Column 22, Line 15, delete "0<z≤1, o<q≤1)." and insert -- 0<z≦1, o<q≦1). --, therefor.

In Column 24, Line 39, delete "1270" and insert -- ~1270 --, therefor.

In Column 24, Line 52, delete "T," and insert -- T., --, therefor.

In Column 27, Lines 5-6, delete "mitochondriat" and insert -- mitochondria --, therefor.

In Column 28, Line 8, delete "anthroquinones," and insert -- anthraquinones, --, therefor.

In Column 31, under "Table", Line 18, delete "dinucelotide" and insert -- dinucleotide --, therefor.

In Column 31, under "Table", Line 19, delete "dinucelotide" and insert -- dinucleotide --, therefor.

In Column 34, Line 53, delete "bacteriand" and insert -- bacteria and --, therefor.

In Column 37, Line 8, delete "ablasion" and insert -- ablation --, therefor.

Signed and Sealed this
Fifteenth Day of March, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,077,316 B2

In Column 37, Line 10, delete "restinosis)," and insert -- restenosis), --, therefor.

In Column 37, Line 13, delete "arthrisis," and insert -- arthritis, --, therefor.

In Column 37, Line 44, delete "ablasion" and insert -- ablation --, therefor.

In Column 37, Line 46, delete "restinosis)," and insert -- restenosis), --, therefor.

In Column 39, Lines 57-58, delete "electrophysipologically" and insert -- electrophysiologically --, therefor.

In Column 43, Line 43, delete "phychiatric" and insert -- psychiatric --, therefor.

In Column 44, Line 18, delete "cardiomyocites)" and insert -- cardiomyocytes) --, therefor.

In Column 46, Line 54, delete "uncageing" and insert -- uncaging --, therefor.

In Column 47, Line 19, delete "photostimulaiton" and insert -- photostimulation --, therefor.

In Column 47, Lines 29-30, delete "photostimulaiton" and insert -- photostimulation --, therefor.

In Column 50, Lines 29-30, delete "boron-dipyrromethere" and insert -- boron-dipyrromethene --, therefor.

In Column 50, Line 30, delete "flourescein" and insert -- fluorescein --, therefor.

In Column 50, Line 31, delete "rhodamin" and insert -- rhodamine --, therefor.

In Column 55, Line 13, delete "aluminand" and insert -- alumina and --, therefor.

In Column 60, Lines 41-42, delete "picoerythrin" and insert -- phycoerythrin --, therefor.

In Column 62, Line 15, delete "orthmyxoviruses," and insert -- orthomyxoviruses, --, therefor.

In Column 62, Line 16, delete "phieboviruses," and insert -- phleboviruses, --, therefor.

In Column 63, Line 36, insert -- fluvialis), -- after "Vibrio".

In Column 63, Line 50, delete "bascillary" and insert -- bacillary --, therefor.

In Column 63, Line 51, delete "(Psuedomonas aerugenosa" and insert -- (Pseudomonas aeruginosa --, therefor.

In Column 64, Line 7, delete "Tricosporon" and insert -- Trichosporon --, therefor.

In Column 65, Lines 58-59, delete "anthroquinones." and insert -- anthraquinones. --, therefor.

CERTIFICATE OF CORRECTION (continued)
U.S. Pat. No. 11,077,316 B2

In Column 66, Line 2, delete "tetrasulonate," and insert -- tetrasulfonate, --, therefor.

In Column 66, Line 2, delete "hematophorphyrin," and insert -- hematoporphyrin, --, therefor.

In Column 66, Line 3, delete "phthadocyanine." and insert -- phthalocyanine. --, therefor.

In Column 66, Line 64, delete "orinactivation" and insert -- or inactivation --, therefor.

In Column 71, Line 40, delete "hasflexible" and insert -- has flexible --, therefor.

In Column 85, Line 53, delete "atreatment" and insert -- a treatment --, therefor.

In Column 87, Line 31, delete "diplacement" and insert -- displacement --, therefor.

In Column 89, Line 28, delete "psoarelen" and insert -- psoralen --, therefor.

In Column 91, Lines 52-53, delete "anthroquinones." and insert -- anthraquinones. --, therefor.

In Column 91, Line 66, delete "tetrasulonate," and insert -- tetrasulfonate, --, therefor.

In Column 91, Lines 66-67, delete "hematophorphyrin," and insert -- hematoporphyrin, --, therefor.

In Column 93, Line 20, delete "BOO" and insert -- BGO --, therefor.

In Column 93, Line 22, delete "LaCl$_3$(Ce)," and insert -- LaCl$_3$(Ce), --, therefor.

In Column 94, Line 52, delete "Er3$^+$;" and insert -- Er$^{3+}$; --, therefor.

In Column 95, Lines 14-15, delete "anthroquinones." and insert -- anthraquinones. --, therefor.

In Column 95, Lines 27-28, delete "hematophorphyrin," and insert -- hematoporphyrin, --, therefor.

In Column 95, Line 29, delete "phthadocyanine." and insert -- phthalocyanine. --, therefor.

In Column 98, Lines 23-24, delete "pharmacutical" and insert -- pharmaceutical --, therefor.

In the Claims

In Column 100, Claim 19, Line 14, delete "anthroquinones." and insert -- anthraquinones. --, therefor.

In Column 100, Claim 22, Line 25, delete "tetrasulonate," and insert -- tetrasulfonate, --, therefor.

In Column 100, Claim 22, Line 25, delete "hematophorphyrin," and insert -- hematoporphyrin, --, therefor.

In Column 100, Claim 22, Line 26, delete "phthadocyanine." and insert -- phthalocyanine. --, therefor.